United States Patent
Yoo et al.

(10) Patent No.: US 9,783,551 B2
(45) Date of Patent: Oct. 10, 2017

(54) PYRANOCHROMENYL PHENOL DERIVATIVE, AND PHARMACEUTICAL COMPOSITION FOR TREATING METABOLIC SYNDROME OR INFLAMMATORY DISEASE

(71) Applicant: GLACEUM, INC., Suwon-si (KR)

(72) Inventors: Sang Ku Yoo, Yongin-si (KR); Jin Wook Chung, Seoul (KR); In Geun Jo, Cheonan-si (KR); Jeong Ho Im, Gwangju-si (KR); Ku Suk Kang, Yongin-si (KR); Jin Young Kim, Suwon-si (KR)

(73) Assignee: Glaceum Inc., Suwon-si (KR)

( * ) Notice: Subject to any disclaimer, the term of this patent is extended or adjusted under 35 U.S.C. 154(b) by 0 days.

(21) Appl. No.: 15/037,230

(22) PCT Filed: Dec. 23, 2014

(86) PCT No.: PCT/KR2014/012688
§ 371 (c)(1),
(2) Date: May 17, 2016

(87) PCT Pub. No.: WO2015/099392
PCT Pub. Date: Jul. 2, 2015

(65) Prior Publication Data
US 2016/0272650 A1    Sep. 22, 2016

(30) Foreign Application Priority Data

Dec. 24, 2013 (KR) .......... 10-2013-0162909
Dec. 17, 2014 (KR) .......... 10-2014-0181951

(51) Int. Cl.
C07D 493/00   (2006.01)
C07D 497/04   (2006.01)
C07D 493/04   (2006.01)

(52) U.S. Cl.
CPC ......... *C07D 497/04* (2013.01); *C07D 493/04* (2013.01)

(58) Field of Classification Search
CPC ..................... C07D 497/04; C07D 493/04
USPC ........................................ 549/387
See application file for complete search history.

(56) References Cited

FOREIGN PATENT DOCUMENTS

| EP | 1440688 A1 | 7/2004 |
|---|---|---|
| JP | 2006-8604 A | 1/2006 |
| KR | 10-2007-0052211 A | 5/2007 |

(Continued)

OTHER PUBLICATIONS

Van Heerden et al, Synthesis of Glabridin Derivatives as Tyrosinase Inhibitors, Journal of the Chemical Society, Perkin Transactions 1: Organic and Bio-Organic Chemistry(1972-1999)(1978), (2),p. 137-145.*

(Continued)

*Primary Examiner* — T. Victor Oh
(74) *Attorney, Agent, or Firm* — NSIP Law

(57) ABSTRACT

Provided are a pyranochromenyl phenol derivative, a pharmaceutically acceptable salt thereof, or a solvate thereof. Also provided is a pharmaceutical composition for preventing or treating metabolic syndrome or inflammatory disease comprising same.
The present invention is efficacious in preventing or treating metabolic syndrome or inflammatory disease and is chemically stable.

19 Claims, 12 Drawing Sheets

(56) References Cited

FOREIGN PATENT DOCUMENTS

| | | |
|---|---|---|
| WO | WO 03/037316 A1 | 5/2003 |
| WO | WO2007/058480 * | 5/2007 |

OTHER PUBLICATIONS

Johnson, Theodore O., et al., "Protein Tyrosine Phosphatase 1B Inhibitors for Diabetes." Nature Reviews Drug Discovery 1.9, 2002, (696-709).

Nerya, Ohad, et al., "Glabrene and Isoliquiritigenin as Tyrosinase Inhibitors from Licorice Roots." Journal of Agricultural and Food Chemistry 51.5, 2003, (8 pages).

Jirawattanapong, Warunee, et al., "Synthesis of Glabridin Derivatives as Tyrosinase Inhibitors." Archives of Pharmacal Research 32.5, 2009, (9 pages).

Combs, Andrew P., "Recent Advances in the Discovery of Competitive Protein Tyrosine Phosphatase 1B Inhibitors for the Treatment of Diabetes, Obesity, and Cancer." Journal of Medicinal Chemistry 53.6, 2009, (2333-2344).

Ao, Mingzhang, et al., "Factors Influencing Glabridin Stability." Natural Product Communications 5.12, 2010, (1907-1912).

Popov, Doina, "Novel protein tyrosine phosphatase 1B inhibitors: interaction requirements for improved intracellular efficacy in type 2 diabetes mellitus and obesity control." Biochemical and Biophysical Research Communications 410.3, 2011, (377-381).

Wu, Feihua, et al., "Hypoglycemic effects of glabridin, a polyphenolic flavonoid from licorice, in an animal model of diabetes mellitus." Molecular Medicine Reports 7.4, 2013, (6 pages).

Feldhammer, Matthew, et al., "PTP1B: A simple enzyme for a complex world." Critical Reviews in Biochemistry and Molecular Biology 48.5, 2013, (430-445).

Database Registry [Online]: Chemical Abstracts Service, Columbus, and Ohio, USA. Retrieved from STN,Registry No. 77808-97-0 (Entered STN: Nov. 16, 1984) (1 page, in English).

Japanese Notice of Allowance dated Apr. 18, 2017 in counterpart Japanese Patent Application No. 2016-540481 (8 pages, with English translation).

van Heerden, Fanie R., et al. "Structure and Synthesis of Some Complex Pyranoisoflavonoids From The Bark Of Dalbergia nitidula Welw. ex Bak." *Journal of the Chemical Society, Perkin Transactions* 1 2 (1978): 137-145. (8 pages, in English).

* cited by examiner

PYRANOCHROMENYL PHENOL DERIVATIVE, AND PHARMACEUTICAL COMPOSITION FOR TREATING METABOLIC SYNDROME OR INFLAMMATORY DISEASE

CROSS-REFERENCE TO RELATED APPLICATIONS

This application is a National Phase entry of PCT Application No. PCT/KR2014/012688, filed on Dec. 23, 2014, which claims priority under 35 U.S. C. §119(e), 120 and 365(c) to Korean Patent Application No. 10-2013-0162909, filed on Dec. 24, 2013 and Korean Patent Application No. 10-2014-0181951, filed on Dec. 17, 2014.

TECHNICAL FIELD

One or more exemplary embodiments relate to a novel pyranochromenylphenol derivative which is effective for preventing or treating a metabolic syndrome or an inflammatory disease, and the use thereof for preventing or treating a metabolic syndrome or an inflammatory disease.

BACKGROUND ART

A human body has approximately 20 billion or more adipocytes, and if supplies of energy are extremely excessive to demands thereon, triglycerides are stored in the adipocytes in the human body, which are degraded into free fatty acids and glucose, which will be used as an energy source upon the exhaustion of energy.

Obesity, which about 30 to about 40% of people of today have, occurs when excessive energy is accumulated due to imbalance of the above process, and shows the increased size and number of adipocytes. The hygienic environment has been improved due to improvement in the standard of living resulting from the recent economic development, frequent consumption of instant food products and changes in dietary habits toward the consumption of more meat induce the accumulation of excessive amounts of caloric energy in the body. These changes in dietary habits of people of today show a tendency of a rapid increase in the obese population in addition to a decrease in consumption of calories due to the lack of exercise. This obesity is so closely associated with a metabolic syndrome that obesity may be used for the diagnosis of a metabolic syndrome.

The metabolic syndrome is a term used to conceptualize a cluster of risk factors of various cardiovascular diseases and type 2 diabetes mellitus as one disease group. This is a useful concept which may comprehensively explain all of the insulin resistance and complex and various metabolic disorders and clinical aspects associated with the same, and refers to a syndrome in which risk factors such as obesity, diabetes, fatty liver and hypertriglyceridemia are together increased. Accordingly, when a person gets a metabolic syndrome, the risk of developing a cardiovascular disease or type 2 diabetes mellitus is increased. According to the ATPIII of US National Cholesterol Education Program published in 2001, when a patient develops three or more of five risk factors such as an abdomen-obesity of 40 inch (102 cm) for a man and 35 inch (88 cm) for a woman in terms of waist circumference, a triglyceride level of 150 mg/dL or more, a HDL cholesterol level of 40 mg/dL or less for a man and 50 mg/dL or less for a woman, a blood pressure of 130/85 mmHg or more, and a fasting glucose of 110 mg/dL or more, the patient is diagnosed with a metabolic syndrome.

Insulin resistance refers to a phenomenon in which even though insulin is normally secreted in vivo, insulin does not induce sufficient supply of glucose to cells. Therefore, glucose in the blood cannot enter cells, thus causing hyperglycemia, and thereby cells cannot perform normal functions due to a shortage of glucose, leading to the manifestation of a metabolic syndrome. The diabetic symptoms thus developed are classified into type 2 diabetes mellitus (T2DM, noninsulin-dependent diabetes mellitus: NIDDM), which is different from type 1 diabetes mellitus (insulin-dependent diabetes mellitus). For this reason, the most preferred method of treating type 2 diabetes mellitus is to induce insulin so as to perform normal functions by improving insulin resistance. Nevertheless, an agent for improving insulin resistance has been scarcely developed so far. Most of the agents for treating type 2 diabetes mellitus currently in use or developed are targeted to further increase the amount of insulin secreted in order to compensate for the lost function of insulin caused by insulin resistance. However, when the amount of insulin secreted in our body is increased, obesity and inflammation are definitely caused, thereby resulting in various side effects such as an increase in cancer incidence, so that unless the problem of insulin resistance is fundamentally alleviated, a temporary normalization of blood sugar may be expected, but a result that health gradually deteriorates is only obtained. For this reason, there is more urgent need in society for a therapeutic agent for type 2 diabetes mellitus, which may normalize blood sugar by alleviating insulin resistance.

Meanwhile, Patent Document 1 discloses the use of glabridin for preventing or treating a metabolic syndrome including hyperlipidemia, fatty liver, glucose metabolism disorder, diabetes and obesity:

Glabridin is known to be effective not only for a metabolic syndrome including hyperlipidemia, fatty liver, glucose metabolism disorder, diabetes and obesity, but also for prevention and treatment such as anti-inflammatory action and anticancer action, but is easily broken down by sunlight, moisture, acidity, basicity, oxygen, heat and the like due to low chemical stability, so that it is very difficult to develop a product utilizing glabridin (Non-Patent Document 1).

According to various studies hitherto published, leptin resistance and insulin resistance are each considered to be an important cause for obesity and type 2 diabetes mellitus (T2DM), and the most representative and inventive mechanism causing these resistances is due to a problem caused during the signaling process in a leptin receptor and an insulin receptor (IR), and both the receptors are commonly closely associated with protein tyrosine phosphatase 1B (PTP1B) (Non-Patent Document 2).

Only from the fact that the signaling process of both leptin (a signaling material which promotes food intake and energy consumption) and insulin (a signaling material which promotes carbohydrate uptake and lipid synthesis) which are the most important hormones associated with the accumulation of energy in our body, it is enough for PTP1B to draw people's attention as the most important therapeutic target for obesity and diabetes. In addition, since the year 2000 in which the action mechanism on PTP1B was clearly identified, PTP1B has actually drawn most attention as an important pharmacological mechanism for treating obesity, type 2 diabetes mellitus, and cancer. That is, a PTP1B inhibitor, which may arbitrarily control the activity of PTP1B, is highly likely to be developed as a therapeutic agent for obesity and type 2 diabetes mellitus, which normalizes the activity of leptin and insulin by alleviating leptin and insulin resistance (Non-Patent Documents 3 and 4).

According to research results revealed by various studies recently conducted, it has been found that PTP1B is closely associated with not only obesity and diabetes, but also various inflammatory diseases, heart diseases, endoplasmic reticulum stress diseases, breast cancer, prostate cancer and the like. As described above, while it has been found that various chronic diseases referred to as adult diseases in a typical sense are directly and indirectly associated with PTP1B, PTP1B has been highlighted as an important and fundamental therapeutic target for treating these adult diseases. In this sense, it is not too much to say that PTP1B is the most basic and fundamental cause of disease, which forms the bottom of many adult diseases (Non-Patent Document 5).

CITATION LIST

Patent Document (Patent Document 1) 1. International Patent Publication WO 07/058480

Non-Patent Document (Non-Patent Document 1) M. Ao, Natural Product Communication 5 (2010), 1907~1912.

(Non-Patent Document 2) D. Popov; Biochem Biophys Res Commun. 410 (2011), 377~381.

(Non-Patent Document 3) A. P. Combs; J. Med. Chem. 53 (2010), 2333~2344.

(Non-Patent Document 4) T. O. Johnson, J. Ermolieff, M. Jirousek; Nature Reviews 1 (2002), 696~709.

(Non-Patent Document 5) M. Feldhammer, N. Uetani, D. Miranda-Saavedra, M. L. Tremblay; Crit. Rev. Biochem. Mol. Biol. 48 (2013) 430~445.

DETAILED DESCRIPTION OF THE INVENTION

Technical Problem

One or more exemplary embodiments include a new pyranochromenylphenol derivative which is excellent in anti-obesity efficacy, antidiabetic efficacy, and anti-inflammatory efficacy, and is not only effective for treatment of hyperlipidemia and the like, but also chemically stable even under acidic or basic conditions as well as general atmospheric conditions which include oxygen.

One or more exemplary embodiments include a pharmaceutical composition for preventing or treating a metabolic syndrome or an inflammatory disease.

Technical Solution

According to one aspect of the present invention, provided are a compound of the following Formula (I), a pharmaceutically acceptable salt thereof, or a solvate thereof:

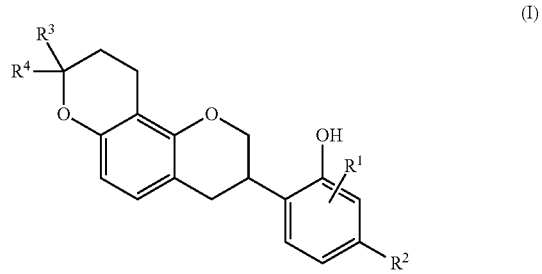

in the formula, $R^1$ is a hydrogen atom, methyl, methoxy, or a halogen atom;

$R^2$ is a hydrogen atom; a substituted or unsubstituted straight or branched $C_1$-$C_6$ alkyl group; a halogen atom; a substituted or unsubstituted straight or branched $C_1$-$C_6$ alkoxy group; or a substituted or unsubstituted straight or branched $C_1$-$C_4$ thioalkyl group;

$R^3$ and $R^4$ are each independently a hydrogen atom, or a $C_1$-$C_2$ alkyl group; and in the case of the substituted alkyl, the substituted alkoxy, and the substituted thioalkyl, the substituent is a halogen atom, a straight or branched $C_1$-$C_5$ alkyl group, a straight or branched $C_1$-$C_5$ alkoxy group, or a straight or branched $C_1$-$C_3$ thioalkyl group.

According to another aspect of the present invention, a pharmaceutical composition for preventing or treating a metabolic syndrome or an inflammatory disease includes a compound of the following Formula (I'), a pharmaceutically acceptable salt thereof, or a solvate thereof:

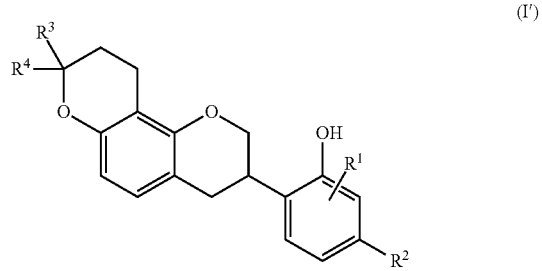

in the formula, $R^1$ is a hydrogen atom, methyl, methoxy, or a halogen atom;

$R^2$ is a hydrogen atom; a hydroxy group; a substituted or unsubstituted straight or branched $C_1$-$C_6$ alkyl group; a halogen atom; a substituted or unsubstituted straight or branched $C_1$-$C_6$ alkoxy group; or a substituted or unsubstituted straight or branched $C_1$-$C_4$ thioalkyl group;

$R^3$ and $R^4$ are each independently a hydrogen atom, or a $C_1$-$C_2$ alkyl group;

in the case of the substituted alkyl, the substituted alkoxy, and the substituted thioalkyl, the substituent is a straight or branched $C_1$-$C_5$ alkyl group, a halogen atom, a straight or branched $C_1$-$C_5$ alkoxy group, or a straight or branched $C_1$-$C_3$ thioalkyl group.

Advantageous Effects

A pharmaceutical composition including the pyranochromenylphenol according to one exemplary embodiment of the present invention is effective for treating or preventing a metabolic syndrome or an inflammatory disease, and is chemically stable.

DETAILED DESCRIPTION

Figure 1:
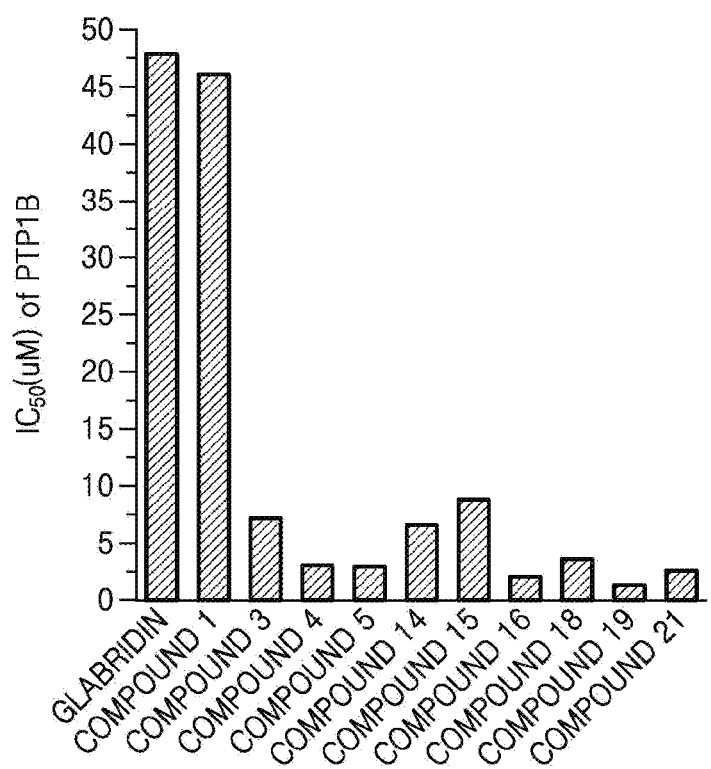
FIG. 1 is a graph showing the results of an experiment of inhibiting PTP1B by the pyranochromenylphenol derivative of the present invention.

Hereinafter, the present invention will be described in more detail.

Unless otherwise defined, all technical terms used in the present invention are used as the same meaning as commonly understood by one with ordinary skill in the art to which the present invention belongs. Further, preferred methods or samples are described herein, but methods or samples which are similar or equivalent to the same are also included in the scope of the present invention. The contents of all the publications described herein as the reference document are incorporated herein in their entirety by reference.

A pyranochromenylphenol derivative according to an aspect of the present invention may be represented by the following Formula (I):

[Formula 1]

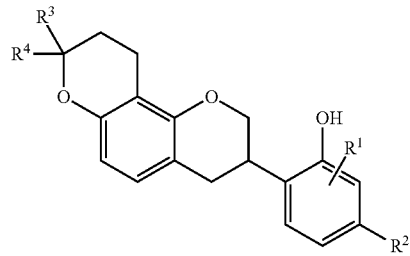

(I)

in the formula, $R^1$ is a hydrogen atom, methyl, methoxy, or a halogen atom;

$R^2$ is a hydrogen atom; a substituted or unsubstituted straight or branched $C_1$-$C_6$ alkyl group; a halogen atom; a substituted or unsubstituted straight or branched $C_1$-$C_6$ alkoxy group; or a substituted or unsubstituted straight or branched $C_1$-$C_4$ thioalkyl group;

$R^3$ and $R^4$ are each independently a hydrogen atom, or a $C_1$-$C_2$ alkyl group; and in the case of the substituted alkyl, the substituted alkoxy, and the substituted thioalkyl, the substituent is a halogen atom, a straight or branched $C_1$-$C_5$ alkyl group, a straight or branched $C_1$-$C_5$ alkoxy group, or a straight or branched $C_1$-$C_3$ thioalkyl group.

The pyranochromenyl phenol derivative according to an exemplary embodiment of the present invention has an excellent effect in preventing or treating a metabolic syndrome such as obesity, diabetes, hyperlipidemia, and fatty liver, or an inflammatory disease, and simultaneously has an excellent effect even in terms of chemical stability.

According to an exemplary embodiment of the present invention, in Formula (I), $R^1$ is a hydrogen atom, and $R^2$ may be methyl, ethyl, n-propyl, isopropyl, n-butyl, n-pentyl, 2-methoxyethyl, trifluoromethyl, fluoro, chloro, bromo, methoxy, ethoxy, n-propoxy, isopropoxy, n-butoxy, n-pentoxy, methoxymethoxy, and the like.

According to another exemplary embodiment of the present invention, when $R^1$ in Formula (I) is a halogen atom, the halogen atom may be fluoro, chloro, or bromo.

According to still another exemplary embodiment of the present invention, the compound of Formula (I) may be one or more of the following compounds.

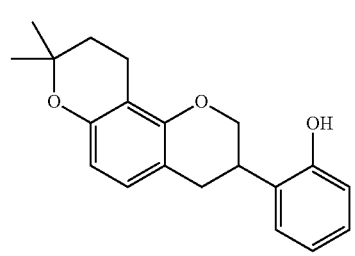

Compound 2

-continued
Compound 3
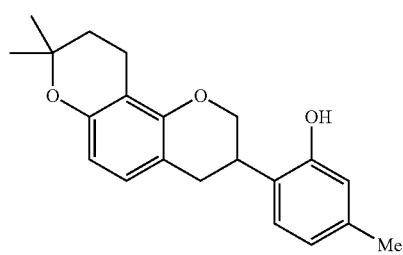
Compound 4
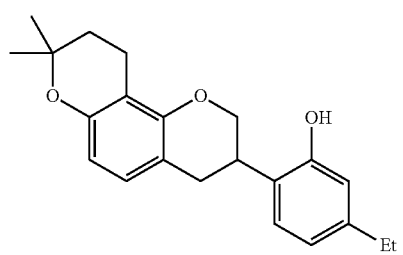
Compound 5
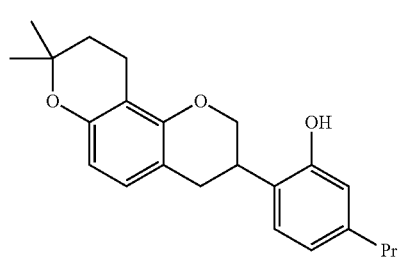
Compound 6
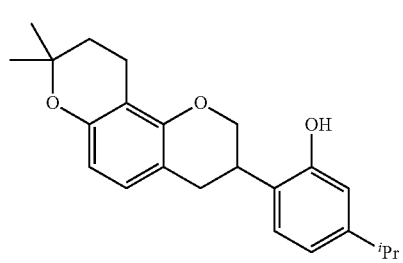
Compound 7
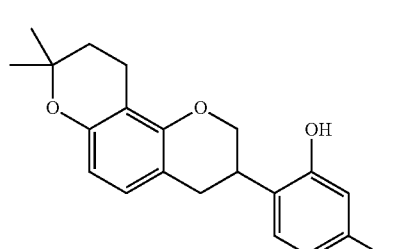
Compound 8
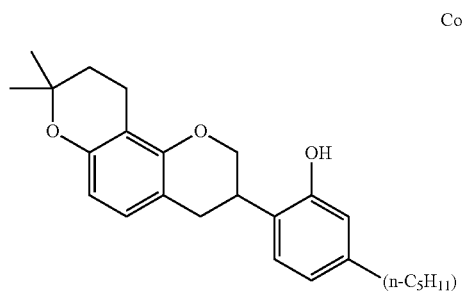
-continued
Compound 9
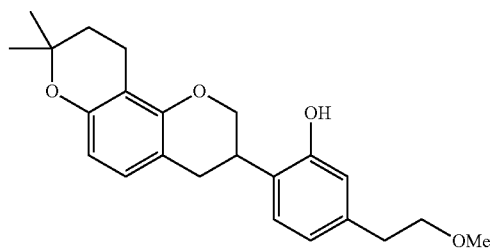
Compound 10
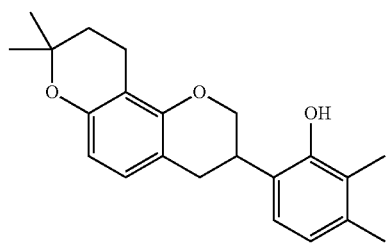
Compound 11
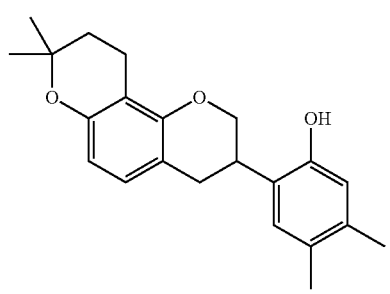
Compound 12
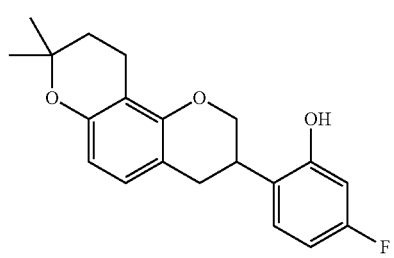
Compound 13
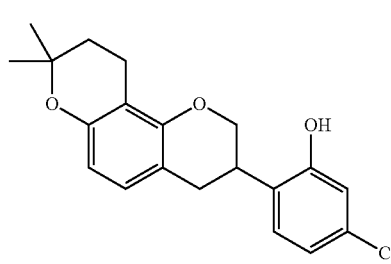
Compound 14
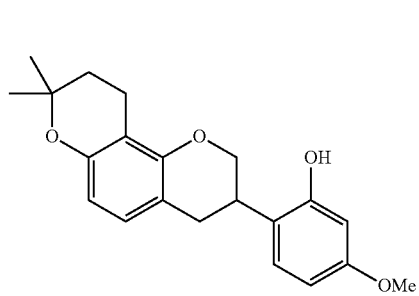

Compound 15

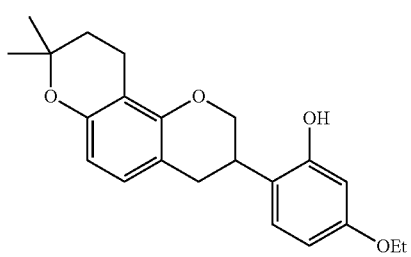

Compound 16

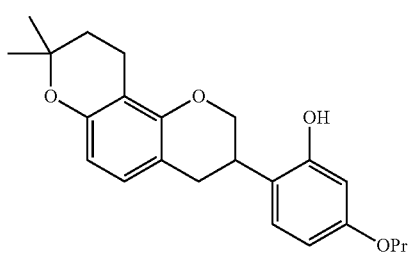

Compound 17

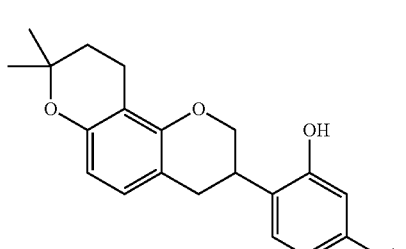

Compound 18

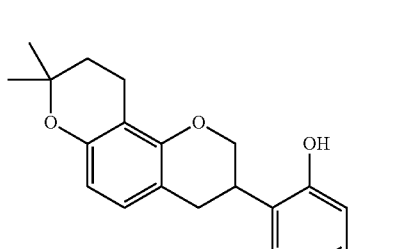

Compound 19

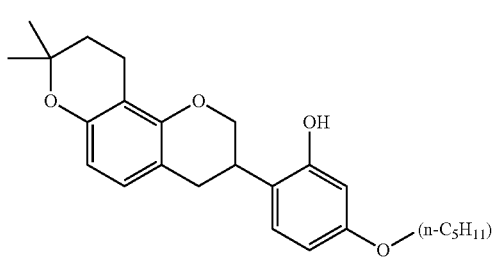

Compound 20

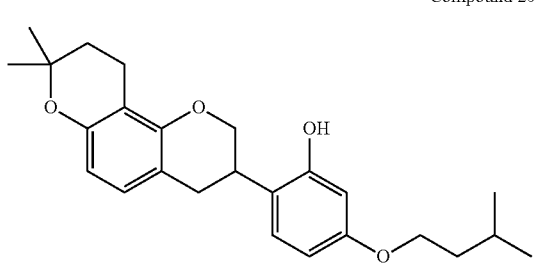

Compound 21

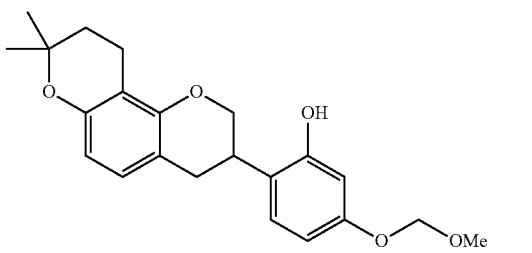

Compound 22

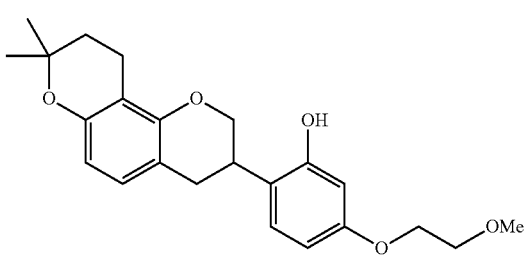

Compound 23

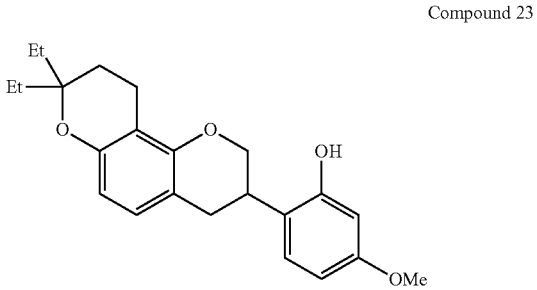

The pharmaceutically acceptable salt may be present as an acid addition salt formed by the compound of Formula (I) and a free acid. The compound of Formula (I) may form a pharmaceutically acceptable acid addition salt by a typical method publicly known in the art. As the free acid, an organic acid or an inorganic acid may be used, and as the inorganic acid, hydrochloric acid, bromic acid, sulfuric acid, phosphoric acid, and the like may be used, and as the organic acid, it is possible to use citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluene sulfonic acid, galacturonic acid, embonic acid, glutamic acid, aspartic acid, and the like.

The pharmaceutically acceptable salt may be present as an inorganic salt of the compound of Formula (I). The compound of Formula (I) may form a pharmaceutically acceptable inorganic salt by a typical method publicly known in the art. Examples of the inorganic salt include salts with aluminum, ammonium, calcium, copper, iron, lithium, magnesium, manganese, potassium, sodium, or zinc, but the present invention is not limited to, and ammonium, calcium, magnesium, potassium or sodium salt is preferred.

Furthermore, the compound of Formula (I) according to the present invention may include not only pharmaceutically acceptable salts, but also all the salts which may be prepared by typical methods, and solvates including hydrates.

A method of preparing the compound of Formula (I) is not particularly limited, but the compound may be prepared based on a synthesis method of (±)-glabridin developed by the present inventor(s) (*Bull. Korean Chem. Soc.* 2007 (28) 481~484).

[Reaction Formula 1]

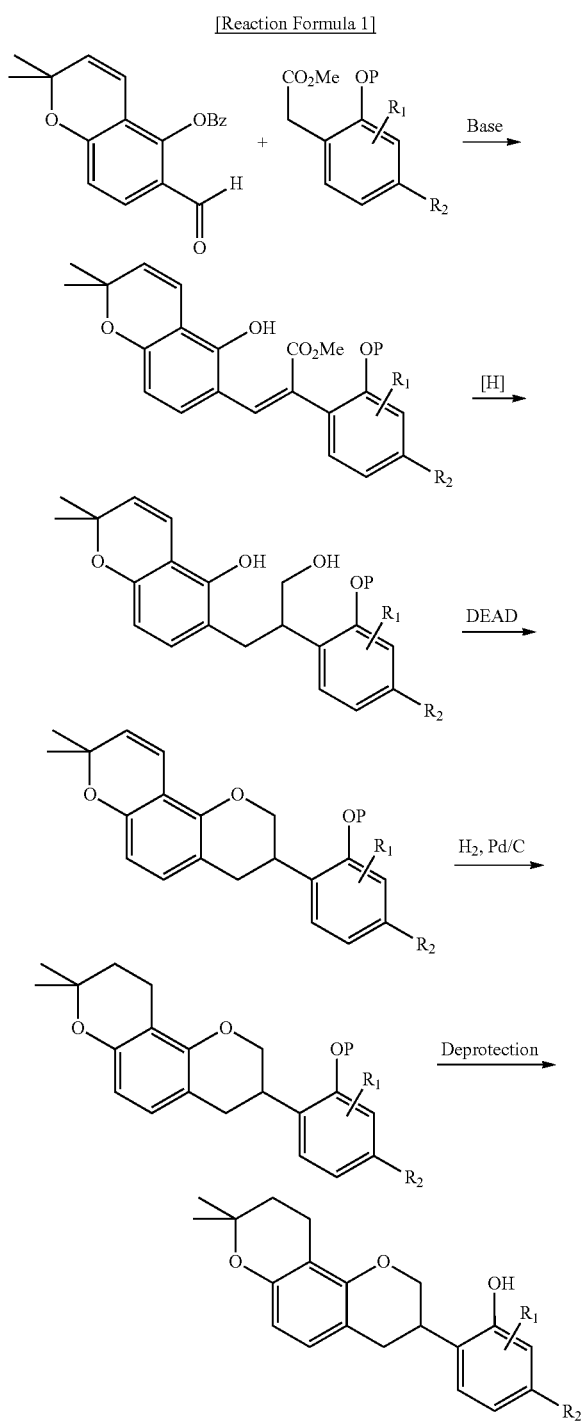

In the reaction formula, OBz is a benzoyloxy group, Me is a methyl group, $R^1$ and $R^2$ are the same as those defined above, P means a protecting group such as a benzyl group, a methoxymethyl group, and a trialkylsilyl group, and DEAD represents diethyl azodicarboxylate. Here, when P is a benzyl group, a deprotection group process simultaneously proceeds during the hydrogenation reaction without a separate deprotection process.

It is obvious that a person skilled in the organic chemistry field may prepare the compound of Formula (I) by modifying the substituents based on Reaction Formula 1 and the preparation methods in the following Examples. In the present specification, the preparation method of the compound of Formula (I) will be described with reference to an Example, but one with ordinary skill in the organic chemistry art may also prepare the compound of Formula (I) by a method different from the method described in the present specification by appropriately modifying the starting material, the reaction route, and the reaction conditions.

A pharmaceutical composition for preventing or treating a metabolic syndrome or inflammatory disease according to another aspect of the present invention includes a compound of the following Formula (I'), pharmaceutically acceptable salts thereof, or solvates thereof.

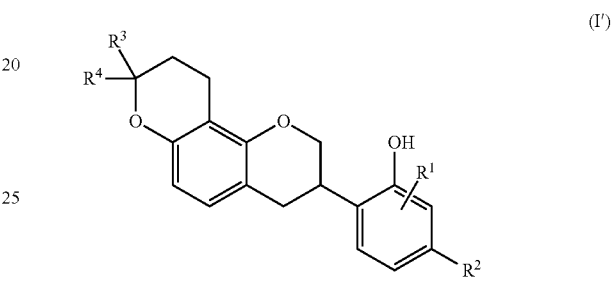

(I')

in the formula, $R^1$ is a hydrogen atom, methyl, methoxy, or a halogen atom;

$R^2$ is a hydrogen atom; a hydroxyl group; a substituted or unsubstituted straight or branched $C_1$-$C_6$ alkyl group; a halogen atom; a substituted or unsubstituted straight or branched $C_1$-$C_6$ alkoxy group; or a substituted or unsubstituted straight or branched $C_1$-$C_4$ thioalkyl group;

$R^3$ and $R^4$ are each independently a hydrogen atom, or a $C_1$-$C_2$ alkyl group; and in the case of the substituted alkyl, the substituted alkoxy, and the substituted thioalkyl, the substituent is a straight or branched $C_1$-$C_5$ alkyl group, a halogen atom, a straight or branched $C_1$-$C_5$ alkoxy group, or a straight or branched $C_1$-$C_3$ thioalkyl group.

According to an exemplary embodiment of the present invention, in Formula (I'), R1 is a hydrogen atom, and $R^2$ may be a hydrogen atom; a hydroxy group; a substituted or unsubstituted straight or branched $C_1$-$C_5$ alkyl group; a straight or branched $C_1$-$C_5$ alkoxy group; or a straight or branched $C_1$-$C_4$ thioalkyl group.

According to another exemplary embodiment of the present invention, in Formula (I'), $R^1$ is a hydrogen atom, and $R^2$ may be methyl, ethyl, n-propyl, isopropyl, n-butyl, n-pentyl, 2-methoxyethyl, trifluoromethyl, fluoro, chloro, bromo, methoxy, ethoxy, n-propoxy, isopropoxy, n-butoxy, n-pentoxy, methoxymethoxy, and the like.

According to still another exemplary embodiment of the present invention, when $R^1$ in Formula (I') is a halogen atom, the halogen atom may be fluoro, chloro, or bromo.

According to yet another exemplary embodiment of the present invention, the compound of Formula (I') may be one or more of the following compounds.

Compound 1
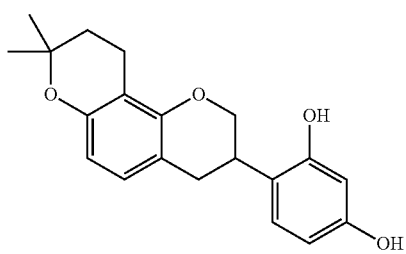
Compound 2
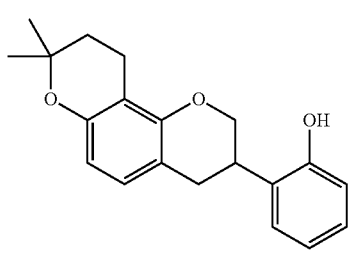
Compound 3
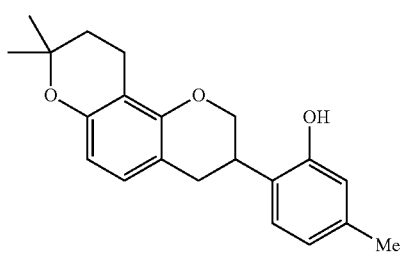
Compound 4
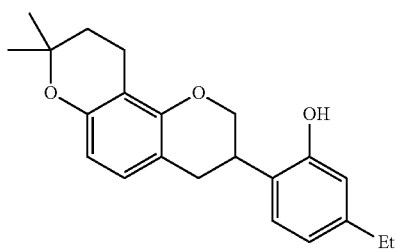
Compound 5
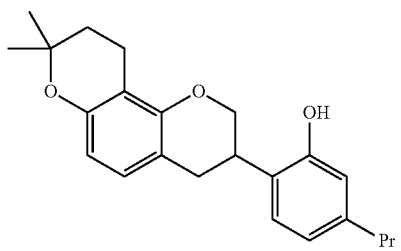
Compound 6
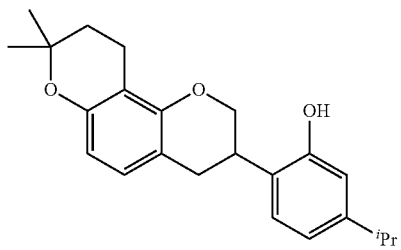
Compound 7
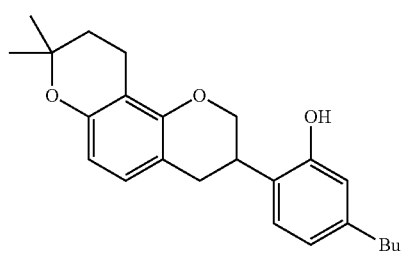
Compound 8
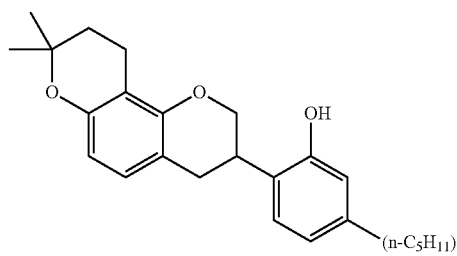
Compound 9
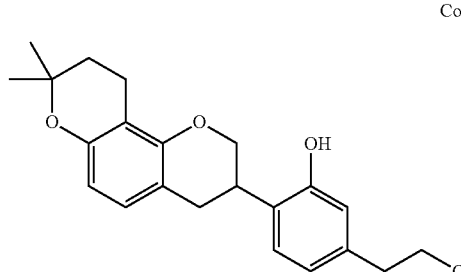
Compound 10
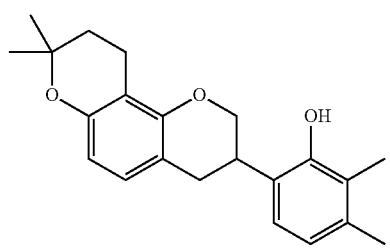
Compound 11
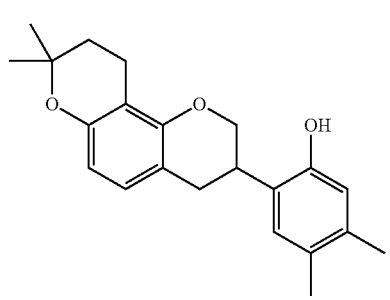
Compound 12
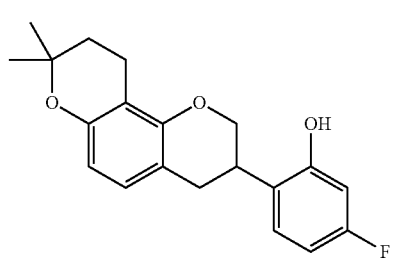

Compound 13

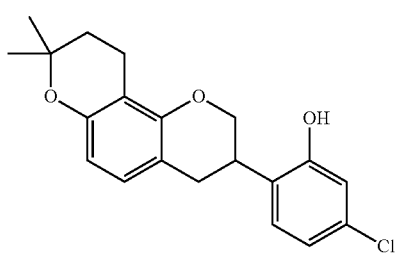

Compound 14

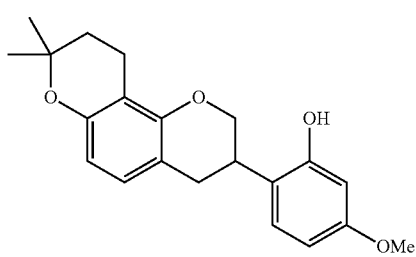

Compound 15

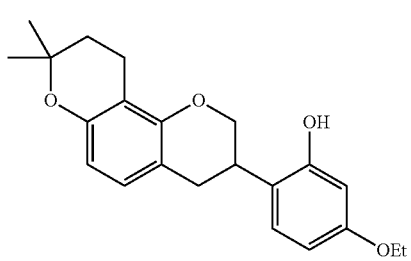

Compound 16

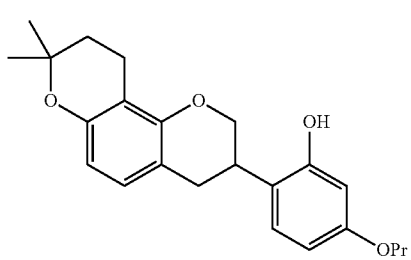

Compound 17

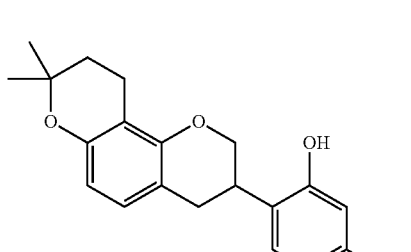

Compound 18

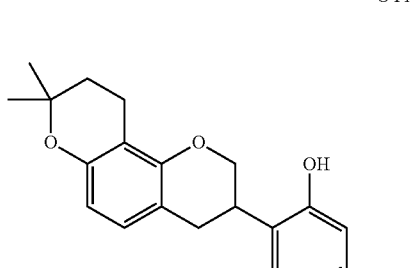

Compound 19

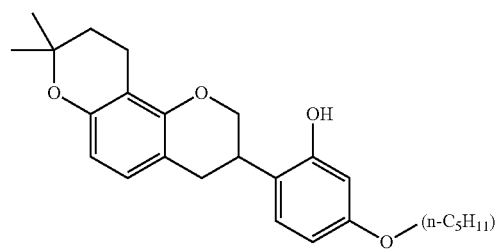

Compound 20

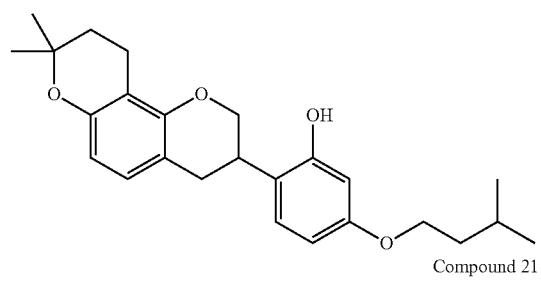

Compound 21

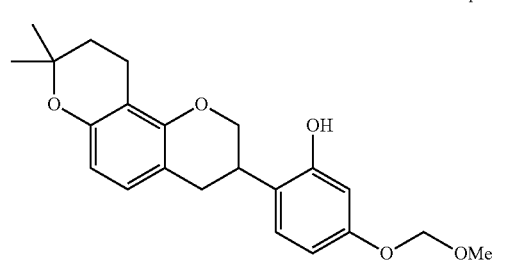

Compound 22

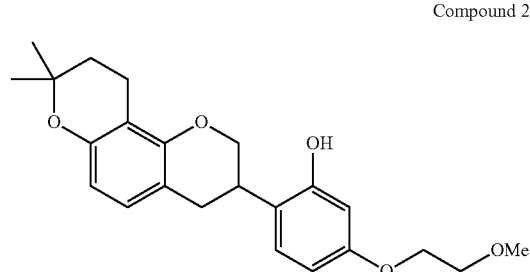

Compound 23

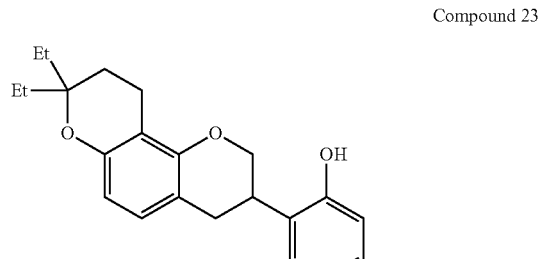

The metabolic syndrome may be one or more of obesity, diabetes, hyperlipidemia, and fatty liver. Further, the diabetes may be type 2 diabetes mellitus (T2DM).

In addition, the metabolic syndrome may be a complex disease of type 2 diabetes mellitus and obesity.

As used herein, the term 'metabolic syndrome' refers to a disease of which the risk increases at the time of getting the metabolic syndrome, and refers to a disease of which the risk factor such as, for example, hypertriglyceridemia, fatty liver, diabetes, and obesity increases, but the present invention is not limited thereto.

The pharmaceutical composition according to an exemplary embodiment of the present invention may prevent or treat the complex disease of type 2 diabetes mellitus and obesity, and thus is very ideal.

Furthermore, the inflammatory disease may be one or more of rheumatoid arthritis; degenerative arthritis; and inflammatory diseases occurring from asthma, atopy, diabetes, or myocardial infarction.

The pharmaceutical composition may be formulated into a typical pharmaceutical dosage form. The dosage form includes orally administered preparations, injection preparations, suppositories, transdermally administered preparations, and nasally administered preparations, but may also be formulated into any dosage form which is not limited thereto. However, the dosage form may be preferably formulated into a preparation for oral administration and an injection preparation.

During formulation into each of the dosage forms, the dosage form may be prepared by adding a pharmaceutically acceptable carrier which is necessary for preparation of each dosage form. As used herein, the term "pharmaceutically acceptable carrier" is used to refer to any constituent ingredient except for pharmaceutically active ingredients. The term "pharmaceutically acceptable" refers to the properties not to cause any pharmaceutically undesirable change via interaction between other constituent ingredients present in the composition (for example, via interaction between carriers or via interaction between the pharmaceutically active ingredient and a carrier). Selection of the pharmaceutically acceptable carrier may be dependent on factors such as the properties and the administration method of a particular dosage form and the effects of the carrier on solubility and stability.

In one exemplary embodiment, the pharmaceutically acceptable carrier included in the oral pharmaceutical composition may be one or more selected from a diluent, a binder, a glidant (or a lubricant), a disintegrant, a stabilizer, a solubilizing agent, a sweetener, a coloring agent, and a flavoring agent, but is not limited thereto.

The diluent refers to any excipient added to increase the volume of the composition to formulate the composition into a target dosage form with an appropriate size. As the diluent, it is possible to use starch (for example, potato starch, corn starch, wheat starch, and pregelatinized starch), microcrystalline cellulose (for example, low-hydrated microcrystalline cellulose), lactose (for example, lactose monohydrate, anhydrous lactose, and spray lactose), glucose, sorbitol, mannitol, sucrose, alginate, alkaline earth metal salts, clay, polyethylene glycol, dicalcium phosphate, anhydrous calcium hydrogenphosphate, silicon dioxide, and the like either alone or as a mixture thereof, but the diluent is not limited thereto. In the present invention, the excipient may be used in a range of about 5 wt % to about 50 wt % based on a total weight of the pharmaceutical composition, and may be used in an amount of, for example, about 10 wt % to about 35 wt % based on the total weight of the pharmaceutical composition for tabletting and quality maintenance.

The binder refers to a material used to impart adhesiveness to materials in powder form to facilitate compression of the materials, and improve fluidity. The binder may be one or more selected from starch, microcrystalline cellulose, highly dispersible silica, mannitol, lactose, polyethylene glycol, polyvinylpyrrolidone, cellulose derivatives (for example, hydroxypropyl methylcellulose, hydroxypropyl cellulose, or low-substituted hydroxypropyl cellulose), natural gum, synthetic gum, povidone, co-povidone, and gelatin, but is not limited thereto. In the present invention, the binder may be used in an amount of about 2 wt % to about 15 wt % based on a total weight of the pharmaceutical composition, and may be used in an amount of, for example, about 1 wt % to about 3 wt % based on the total weight of the pharmaceutical composition for tabletting and quality maintenance.

The disintegrant refers to a material added to facilitate collapse or disintegration of a solid dosage form after administrated into the body. As the disintegrant, it is possible to use starch, such as sodium starch glycolate, corn starch, potato starch, or pregelatinized starch or modified starch; clay, such as bentonite, montmorillonite, or veegum; cellulose, such as microcrystalline cellulose, hydroxypropyl cellulose, or carboxymethyl cellulose; algins, such as sodium alginate or alginic acid; a cross-linked cellulose, such as croscarmellose sodium; gum such as guar gum or xanthan gum; a cross-linked polymer such as cross-linked polyvinylpyrrolidone (crospovidone); or an effervescent ingredient such as sodium bicarbonate or citric acid, either alone or as a mixture thereof, but the disintegrant is not limited thereto. In the present invention, the disintegrant may be used in an amount of about 2 wt % to about 15 wt % based on a total weight of the pharmaceutical composition, and may be used in an amount of, for example, about 4 wt % to about 10 wt % based on the total weight of the pharmaceutical composition for tabletting and quality maintenance.

The glidant or lubricant refers to a material that prevents cohesion of powders to a compressing system and improves flowability of granules. As the glidant, it is possible to use hard anhydrous silicic acid, talc, stearic acid, a metal salt (magnesium salt, calcium salt, or the like) of stearic acid, sodium lauryl sulfate, hydrogenated vegetable oil, sodium benzoate, sodium stearyl fumarate, glycerylbehenate, glycerylmonostearate, or polyethylene glycol, either alone or as a mixture thereof, but the glidant is not limited thereto. In the present invention, the glidant may be used in an amount of about 0.1 wt % to about 5 wt % based on a total weight of the pharmaceutical composition, and may be used in an amount of, for example, about 1 wt % to about 3 wt % based on the total weight of the pharmaceutical composition for tabletting and quality maintenance.

As the adsorbent, it is possible to use hydrated silicon dioxide, hard anhydrous silicic acid, colloidal silicon dioxide, magnesium aluminometasilicate, microcrystalline cellulose, lactose, or a cross-linked polyvinylpyrrolidone, either alone or as a mixture thereof, but the adsorbent is not limited thereto.

The stabilizer may be one or more selected from antioxidants, such as butylhydroxyanisol, butylhydroxytoluene, carotene, retinol, ascorbic acid, tocopherol, tocopherolpolyethylene glycol succinic acid, or propyl gallate; cyclic sugar compounds such as cyclodextrin, carboxyethyl cyclodextrin, hydroxypropyl cyclodextrin, sulfobutylether, or cyclodextrin; and organic acids such as phosphoric acid, lactic acid, acetic acid, citric acid, tartaric acid, succinic acid, maleic acid, fumaric acid, glycolic acid, propionic acid, gluconic acid, or glucuronic acid, but is not limited thereto.

Optionally, an additive publicly known to improve the taste as well as mask the off-taste of the active ingredient may be included. For example, a sweetener such as sucralose, sucrose, fructose, erythritol, acesulfame potassium, sugar alcohol, honey, sorbitol, or aspartame may be added to more effectively mask bitterness and maintain the stability and quality of the preparation. Further, an acidifier such as citric acid or sodium citrate; a natural flavoring such as Japanese apricot flavor, lemon flavor, pineapple flavor, or herbal flavor; or a natural dye such as natural fruit juice, chlorophyllin, or flavonoid may be used.

The oral pharmaceutical composition may be a solid preparation, a semi-solid preparation or a liquid preparation for oral administration. Examples of the solid preparation for oral administration include a tablet, a pill, a hard or soft capsule, a powder, a fine granule, a granule, a powder for reconstitution of solution or suspension, a lozenge, a wafer, an oral strip, a dragee, a chewable gum and the like for oral administration, but are not limited thereto. The liquid preparation for oral administration includes solution, suspension, emulsion, syrup, elixir, spirit, aromatic waters, lemonade, extract, precipitant, tincture, and oily medicine. The semi-solid preparation includes aerosol, cream, gel and the like, but is not limited thereto.

The pharmaceutical composition according to the present invention may be formulated into an injection preparation, and when the composition may be formulated into an injection preparation, the pharmaceutical composition according to the present invention may include a non-toxic buffer solution which is isotonic to a non-toxic buffer solution as a diluent, and examples thereof include a phosphoric acid buffer solution with a pH of 7.4, and the like. The pharmaceutical composition may include other diluents or additives in addition to the buffer solution.

A method of preparing a carrier used in the aforementioned preparation and the preparation may be selected and performed as widely known in the art, and the carrier and the preparation may be prepared according to the methods described in Remington's Pharmaceutical Science latest edition.

The dosage and administration time may be dependent on age, sex, type of disease, status of disease, body weight, administration route, administration frequency, and type of drug. The daily dosage is about 0.1 mg/kg to about 1,000 mg/kg, preferably about 1 mg/kg to about 100 mg/kg. The dosage may be appropriately increased and decreased according to type of disease, progress of disease, administration route, sex, age, body weight and the like.

In order to obtain a preventive or therapeutic effect of a metabolic syndrome or a complex disease of diabetes and obesity, the pharmaceutical composition according to the present invention as an effective ingredient may be arbitrarily administered several times such the total daily dosage is about 0.1 mg/kg to about 1,000 mg/kg as a compound based on an adult. The dosage may be appropriately increased and decreased according to type of disease, progress of disease, administration route, sex, age, body weight, health status, and the like.

The pharmaceutical composition according to the present invention may contain the compound of Formula (I') in an amount of about 0.0001 wt % to about 10 wt %, preferably about 0.001 wt % to about 1 wt % based on a total weight of the entire composition.

Hereinafter, the present invention will be described in more detail with reference to the following Examples and Experimental Examples. However, these Examples and Experimental Examples are provided only for better understanding of the present invention, and the scope of the present invention is not limited by these Examples and Experimental Examples.

The reagents used in the following Preparation Examples and Examples are reagent-graded from Sigma-Aldrich Co., Ltd., unless otherwise indicated.

Preparation Example 1: Preparation of Glabridin

A commercially available glabridin product which had been extracted from licorice and purified in a content level of 40% was purchased and purified by silica gel column chromatography to obtain pure glabridin.

Preparation Example 2: Preparation of Compound 1

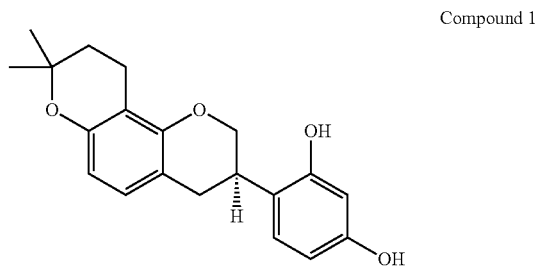 [SMILES: CC1(C)CCc2c(ccc3c2OC[C@@H](c2ccc(O)cc2O)C3)O1]

Compound 1

The glabridin obtained in Preparation Example 1 was subjected to hydrogenation reaction in accordance with the document (Archives of Pharmacal Research 32 (2009) 647~654) to obtain 3",4"-dihydroglabridin (Compound 1).

Preparation Example 3: Synthesis of 6-formyl-2,2-dimethyl-2H-chromen-5-yl benzoate 5-hydroxy-2,2-dimethyl-2H-chromen-6-carbaldehyde was prepared in accordance with the method of [Tetrahedron, 57 (2001), 5335~5338], and then 2.04 g (10.0 mmol) of the compound was dissolved in 20 ml of $CH_2Cl_2$, and the resulting solution was stirred at room temperature for 5 hours while 1 ml of TEA and 1.54 g (11.0 mmol) of benzoyl chloride were added thereto. 10 ml of a $NaHCO_3$ saturated aqueous solution was added thereto, the resulting solution was stirred for another 10 min, and an aqueous layer and an organic layer were separated. The separated aqueous layer was further extracted using 10 ml of $CH_2Cl_2$, the extract was combined with the organic layer, the resulting mixture was combined with the organic layer and treated with $MgSO_4$ and filtered, and the filtrate was concentrated. The solid thus concentrated was recrystallized using isopropyl alcohol (IPA) to obtain 2.51 g (8.1 mmol) of pure 6-formyl-2,2-dimethyl-2H-chromen-5-yl benzoate.

$^1$H-NMR ($CDCl_3$): 9.92 (s, 1H), 8.25 (m, 2H), 7.71 (d, 1H), 7.68 (m, 1H), 7.55 (t, 2H), 6.83 (d, 1H), 6.38 (d, 1H), 5.69 (d, 1H), 1.49 (s, 6H).

Preparation Example 4: Synthesis of (methyl 2-methoxymethoxy phenyl) acetate 3.04 g (20.0 mmol) of 2-hydroxyphenyl acetic acid was dissolved in 20 ml of methanol, and 1.0 ml of concentrated sulfuric acid was added thereto. The reaction solution was refluxed for 10 hours, and then distilled under reduced pressure for concentration. The concentrate was subjected to column chromatography to obtain 2.78 g (16.7 mmol) of (methyl 2-hydroxyphenyl) acetate. 2.8 g (20.0 mmol) of $K_2CO_3$ was again added to a solution obtained by dissolving the aforementioned compound in 20 ml of acetone, 2.40 g (30.0 mmol) of chloromethyl methyl ether was slowly added thereto for 30 minutes while the resulting solution was vigorously stirred at room temperature, and the mixture was vigorously stirred overnight. Then, the reaction solution was filtered to remove solid ingredients, the filtrate was distilled under reduced pressure for concentration, and then the concentrate was purified by silica gel column chromatography to obtain 2.56 g (12.3 mmol) of (2-methoxymethoxy phenyl) acetic methyl ester.

$^1$H-NMR (CDCl$_3$): 7.239 (t, 1H, J=8.0 Hz), 7.201 (d, 1H, J=8.0 Hz), 7.099 (d, 1H, J=8.0 Hz), 6.973 (t, 1H, J=8.0 Hz), 5.191 (s, 2H), 3.687 (s, 3H), 3.666 (s, 2H), 3.459 (s, 3H).

Preparation Example 5: Synthesis of (methyl 2-benzyloxy-4-methylphenyl) acetate 3.01 g (20.0 mmol) of 2'-hydroxy-4'-methylacetophenone was dissolved in 30 ml of CH$_2$Cl$_2$, and 5 ml of a 15% NaOH aqueous solution and 1.0 g of tetrabutylammonium bromide were added thereto. 3.42 g (20.0 mmol) of benzyl bromide was added thereto while the reaction solution was vigorously stirred, and the resulting solution was refluxed overnight under vigorous stirring. The reaction solution was separated into each layer, the aqueous layer was further extracted using 20 ml of CH$_2$Cl$_2$, the CH$_2$Cl$_2$ layer was collected into one mixture, and then the resulting mixture was distilled under reduced pressure for concentration. The concentrate was subjected to chromatography to obtain 3.89 g (16.2 mmol) of 2'-benzyloxy-4'-methylacetophenone. 3 ml of HClO$_4$ was added to a solution obtained by well dissolving the obtained product in 20 ml of methanol, and the ingredients were well mixed with each other at room temperature. 7.33 g (16.5 mmol) of thallium nitrate (Tl(NO$_3$)$_3$.3H$_2$O) was added dropwise thereto for 30 minutes while the reaction solution thus prepared was vigorously stirred at room temperature, and then the resulting mixture was further stirred at room temperature for 1 hour. Then, 30 ml of a NaHCO$_3$ saturated aqueous solution was added to the reaction solution for neutralization, and the resulting solution was distilled under vacuum to remove MeOH. 20 ml of CH$_2$Cl$_2$ was added to the reaction solution to extract the organic layer, the organic layer was concentrated, and then the concentrate was subjected to chromatography to obtain 3.70 g (13.7 mmol) of (methyl 2-benzyloxy-4-methylphenyl) acetate.

$^1$H-NMR (CDCl$_3$): 7.28~7.45 (m, 5H), 7.088 (d, 1H, J=8.0 Hz), 6.767 (s, 1H) 6.761 (d, 1H, J=8.0 Hz), 5.065 (s, 2H), 3.644 (s, 2H), 3.625 (s, 3H), 2.334 (s, 3H).

Preparation Example 6: Synthesis of (methyl 2-benzyloxy-4-ethylphenyl) acetate 12.2 g (100.0 mmol) of 3-ethylphenol was dissolved in 150 ml of CH$_2$Cl$_2$, and 15 ml of triethylamine was slowly added thereto for 1 hour under stirring. 11.2 g (220.0 mmol) of acetic anhydride was slowly added thereto for 1 hour under ice bath, and the resulting solution was vigorously stirred for 2 hours. 200 ml of a saturated brine was slowly added to the reaction solution, the resulting solution was vigorously stirred for 10 minutes, and then an organic layer was separated and concentrated under reduced pressure. 16.7 g (110.0 mmol) of anhydrous AlCl$_3$ was added to a separately prepared flask, and the concentrate previously prepared was slowly dropped to the flask under vigorous stirring using a mechanical stirrer, and subsequently, the flask was heated to 165° C. under vigorously stirring, and maintained at the state for 1 hour. The reaction mixture was cooled to room temperature, and then 500 ml of a saturated brine was slowly added thereto, and the solution was left to stand such that the reaction mixture was dissolved in water for complete dissolution. When the solid was dissolved in water and completely disappeared, extraction was performed using 500 ml of CH$_2$Cl$_2$. The organic layer was separated and concentrated, and again dissolved in 150 ml of CH$_2$Cl$_2$, and 25 ml of a 15% aqueous NaOH solution and 3.0 g of tetrabutylammonium bromide were added thereto. 18.82 g (110.0 mmol) of benzyl bromide was added thereto while the reaction solution was vigorously stirred, and the resulting solution was refluxed overnight under vigorous stirring. The reaction solution was separated into each layer and the aqueous layer was once extracted using 50 ml of CH$_2$Cl$_2$, and then the CH$_2$Cl$_2$ layer was collected into one mixture, and the mixture was primarily distilled under reduced pressure for concentration. The concentrate was distilled under high vacuum (about 155° C./0.01 mmHg to about 160° C./0.01 mmHg) to obtain 18.70 g (73.6 mmol) of 2'-benzyloxy-4'-ethylacetophenone. 15 ml of HClO$_4$ was added to a solution obtained by well dissolving the obtained product in 10 ml of methanol, and the ingredients were well mixed with each other at room temperature. 33.33 g (75.0 mmol) of Tl(NO$_3$)$_3$.3H$_2$O was slowly added dropwise thereto for 60 minutes while the reaction solution thus prepared was vigorously stirred at room temperature, and then the resulting mixture was further stirred at room temperature for 5 hours. Then, 30 ml of a NaHCO$_3$ saturated aqueous solution was added to the reaction solution for neutralization, and the resulting solution was distilled under vacuum to remove MeOH. 80 ml of CH$_2$Cl$_2$ was added to the reaction solution to extract the organic layer, the organic layer was concentrated, and then the concentrate was subjected to silica gel column chromatography to obtain 17.86 g (62.8 mmol) of (methyl 2-benzyloxy-4-ethylphenyl) acetate.

$^1$H-NMR (CDCl$_3$): 7.28~7.45 (m, 5H), 7.116 (d, 1H, J=8.0 Hz), 6.787 (m, 2H), 5.078 (s, 2H), 3.649 (s, 2H), 3.627 (s, 3H), 2.630 (q, 2H, J=8.0 Hz), 1.228 (t, 3H, J=8.0 Hz).

Preparation Example 7: Synthesis of (methyl 2-benzyloxy-4-propylphenyl) acetate (Methyl 2-benzyloxy-4-propylphenyl) acetate was obtained in the same manner as in Preparation Example 6, except that 15.22 g (100 mmol) of 3-propylphenol was used instead of 3-ethylphenol.

$^1$H-NMR (CDCl$_3$): 7.28~7.45 (m, 5H), 7.109 (d, 1H, J=8.0 Hz), 6.764 (d, 1H, J=8.0 Hz) 6.763 (s, 1H), 5.073 (s, 2H), 3.650 (s, 2H), 3.627 (s, 3H), 2.561 (t, 2H, J=4.0 Hz), 1.628 (m, 2H), 0.936 (t, 3H, J=7.6 Hz).

Preparation Example 8: Synthesis of (methyl 2-benzyloxy-4-butylphenyl) acetate (Methyl 2-benzyloxy-4-butylphenyl) acetate was obtained in the same manner as in Preparation Example 6, except that 3-butylphenol was used instead of 3-ethylphenol.

$^1$H-NMR (CDCl$_3$): 7.30~7.43 (m, 5H), 7.110 (d, 1H, J=8.0 Hz), 6.768 (d, 1H, J=8.0 Hz), 6.766 (s, 1H), 5.079 (s, 2H), 3.653 (s, 2H), 3.632 (s, 3H), 2.589 (t, 2H, J=8.0 Hz), 1.588 (m, 2H), 1.348 (m, 2H), 0.925 (t, 3H, J=7.4 Hz).

Preparation Example 9: Synthesis of (methyl 2-benzyloxy-4,5-dimethylphenyl) acetate (Methyl 2-benzyloxy-4,5-dimethylphenyl) acetate was obtained in the same manner as in Preparation Example 6, except that 3,4-dimethylphenol was used instead of 3,4-ethylphenol.

$^1$H-NMR (CDCl$_3$): 7.28~7.46 (m, 5H), 7.007 (s, 1H), 6.785 (s, 1H) 5.083 (s, 2H), 3.670 (s, 3H), 2.272 (s, 3H), 2.228 (s, 3H).

Preparation Example 10: Synthesis of (methyl 2-benzyloxy-4-methoxyphenyl) acetate 4.9 g (21.7 mmol) of 2'-hydroxy-4'-methylacetophenone was dissolved in 30 ml of $CH_2Cl_2$, and 5 ml of a 15% NaOH aqueous solution and 1.0 g of tetrabutylammonium bromide were added thereto. 3.42 g (20.0 mmol) of benzyl bromide was added thereto while the reaction solution was vigorously stirred, and the resulting solution was refluxed overnight under vigorous stirring. The reaction solution was separated into each layer, the aqueous layer was further extracted using 20 ml of $CH_2Cl_2$, the $CH_2Cl_2$ layer was collected into one mixture, and then the resulting mixture was distilled under reduced pressure for concentration. The concentrate was subjected to column chromatography to obtain 4.27 g (15.8 mmol) of 2'-benzyloxy-4'-methylacetophenone. A mixture of the aforementioned product, 1.76 g (20.0 mmol) of morpholine, and 1.5 g of sulfur was again vigorously stirred at 160° C. overnight. The reaction solution was cooled to room temperature, and then subjected to silica gel column chromatography as it is to obtain 4.24 g (11.4 mmol) of 2-(2-benzyloxy)-4-methoxyphenyl)-1-morpholinoethanethione. The aforementioned product was added to 30 ml of a saturated ethanol solution, the resulting solution was refluxed for 8 hours, and then concentrated hydrochloric acid was slowly added while the resulting mixture was cooled to 0° C. to adjust the pH to 1 or less. A solid product obtained by distilling the mixture under reduced pressure for concentration was dissolved using 30 ml of $CH_2Cl_2$ and 20 ml of water, and then the resulting mixture was separated into each other. The aqueous layer was further extracted using 30 ml of $CH_2C_{12}$, collected into one mixture, and concentrated. 20 ml of methanol was added to dissolve the concentrated solid product, and the resulting solution was refluxed for 10 hours while 1 ml of concentrated sulfuric acid was added thereto. The reaction solution was dissolved in 30 ml of $CH_2C_{12}$, washed with brine, concentrated, and then purified using silica gel chromatography to obtain (methyl 2-benzyloxy-4-methoxyphenyl) acetate.

$^1$H-NMR ($CDCl_3$): 7.27~7.43 (m, 5H), 7.100 (d, 1H, J=8.0 Hz), 6.511 (d, 1H, J=2.0 Hz), 6.461 (dd, 1H, J=8.0, 2.0 Hz), 5.040 (s, 2H), 3.763 (s, 3H), 3.619 (s, 3H), 3.605 (s, 2H).

Preparation Example 11: Synthesis of (methyl 2-benzyloxy-4-ethoxyphenyl) acetate (Methyl 2-benzyloxy-4-ethoxyphenyl) acetate was obtained in the same manner as in Preparation Example 10, except that 2'-hydroxy-4'-ethoxyacetophenone was used instead of 2'-hydroxy-4'-methoxyacetophenone.

$^1$H-NMR ($CDCl_3$): 7.28~7.45 (m, 5H), 7.117 (d, 1H, J=8.0 Hz), 6.546 (d, 1H, J=2.4 Hz) 6.483 (dd, 1H, J=8.0, 2.4 Hz), 5.073 (s, 2H), 4.028 (q, 2H, J=6.8 Hz), 3.653 (s, 3H), 3.635 (s, 2H), 1.421 (t, 3H, J=7.8 Hz).

Preparation Example 12: Synthesis of (methyl 2-benzyloxy-4-propoxyphenyl) acetate (Methyl 2-benzyloxy-4-propoxyphenyl) acetate was obtained in the same manner as in Preparation Example 11, except that 2'-hydroxy-4'-propoxyacetophenone was used instead of 2'-hydroxy-4'-methoxyacetophenone.

$^1$H-NMR ($CDCl_3$): 7.28~7.45 (m, 5H), 7.098 (d, 1H, J=8.0 Hz), 6.538 (d, 1H, J=2.4 Hz) 6.469 (dd, 1H, J=8.0, 2.4 Hz), 5.055 (s, 2H), 3.898 (t, 2H, J=6.4 Hz), 3.632 (s, 3H), 3.616 (s, 2H), 1.795 (m, 2H), 1.033 (t, 3H, J=6.8 Hz).

Preparation Example 13: Synthesis of (methyl 2-benzyloxy-4-butoxyphenyl) acetate (Methyl 2-benzyloxy-4-butoxyphenyl) acetate was obtained in the same manner as in Preparation Example 11, except that 2'-hydroxy-4'-butoxyacetophenone was used instead of 2'-hydroxy-4'-methoxyacetophenone.

$^1$H-NMR ($CDCl_3$): 7.28~7.45 (m, 5H), 7.083 (d, 1H, J=8.0 Hz), 6.518 (d, 1H, J=2.0 Hz) 6.456 (dd, 1H, J=8.0, 2.0 Hz), 5.040 (s, 2H), 3.925 (t, 2H, J=6.4 Hz), 3.618 (s, 3H), 3.602 (s, 2H), 1.746 (m, 2H), 1.475 (m, 2H), 0.975 (t, 3H, J=7.2 Hz).

Preparation Example 14: Synthesis of 6-formyl-2,2-diethyl-2H-chromen-5-yl benzoate 6-formyl-2,2-diethyl-2H-chromen-5-yl benzoate was obtained in the same manner as in Preparation Example 3, except that 3-ethylpent-2-enal was used instead of 3-methylcrotonaldehyde in the process of synthesizing 5-hydroxy-2,2-dimethyl-2H-chromen-6-carbaldehyde in accordance with the method of Document [Tetrahedron, 57 (2001), 5335~5338] referenced in Preparation Example 3.

$^1$H-NMR ($CDCl_3$): 9.893 (s, 1H), 8.251 (m, 2H), 7.688 (d, 1H, J=8.4 Hz), 7.686 (m, 1H), 7.551 (t, 2H, J=7.2 Hz), 6.813 (d, 1H, J=8.4 Hz), 6.496 (d, 1H, J=10.2 Hz), 5.544 (d, 1H, J=10.2 Hz), 1.804 (m, 2H), 1.657 (m, 2H), 0.949 (t, 6H).

Compounds 2 to 23 were prepared according to the following reaction formulae.

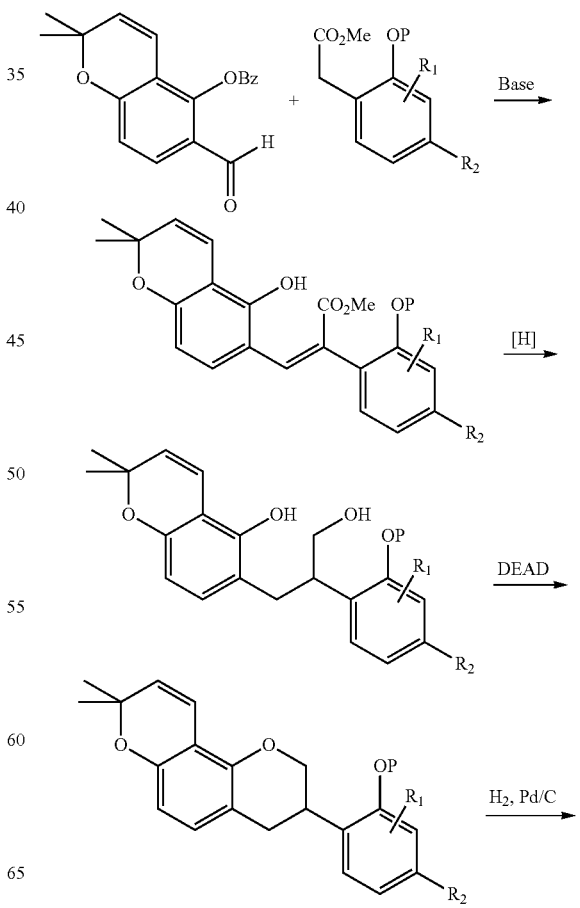

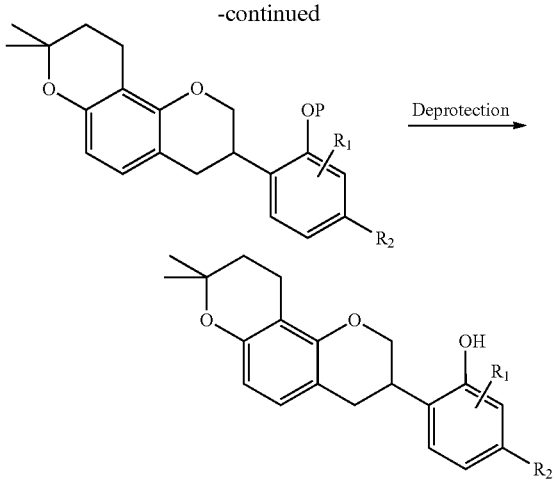

Here, in the final hydrogenation reaction and the deprotecting process, the sequence may be changed if necessary. In addition, when the protecting group is benzyl or substituted benzyl, it is not necessary to distinguish a separate process from the process because the hydrogen reaction and the deprotecting process are simultaneously carried out.

Example 1: Synthesis of 3-(2-hydroxyphenyl)-8,8-dimethyl-2,3,4,8,9,10-hexahydropyrano [2,3-f] chromene (Compound 2)

(1) Preparation of methyl 2-(2-(methoxymethoxy) phenyl)-3-(2,2-dimethyl-5-hydroxy-2H-1-benzopyran-6-yl) acrylate A 3-necked round flask was cooled to −78° C. under nitrogen atmosphere in a dry ice-acetone bath. Here, 45 ml of a 1.0 M lithium diisopropylamide (LDA) in THF solution was added thereto, and then a solution obtained by dissolving 6.30 g (30.0 mmol) of (methyl 2-methoxymethoxy phenyl) acetate prepared in Preparation Example 4 in 100 ml of THF was slowly added thereto for 30 minutes, and further stirred for 30 minutes.

A solution obtained by dissolving 9.24 g (30.0 mmol) of 5-benzoyloxy-2,2-dimethyl-6-formyl-2H-1-benzopyran in 20 ml of THF was slowly added to the above reaction solution for 30 minutes, and then further stirred for 30 minutes. The 3-necked round flask was removed from the dry ice-acetone bath, and then was heated such that the temperature of the reaction solution was slowly increased to 0° C. At this state, 100 ml of brine was added to the reaction solution, and the resulting solution was vigorously stirred at room temperature for 30 minutes. The organic layer was separated, and then the aqueous layer was further extracted using 100 ml of ethyl acetate. The organic layer thus extracted with ethyl acetate was combined with the organic layer previously separated, and the resulting mixture was dried over anhydrous sodium sulfate, and then distilled under reduced pressure for concentration. The concentrate was purified by silica gel column chromatography to obtain 5.16 g (13.02 mmol) of methyl 2-(2-(methoxymethoxy) phenyl)-3-(2,2-dimethyl-5-hydroxy-2H-1-benzopyran-6-yl) acrylate. (Yield: 43%)

$^1$H-NMR (CDCl$_3$): 8.007 (s, 1H), 7.293 (td, 1H, J=8.0, 1.6 Hz), 7.170 (d, 1H, J=8.0 Hz), 7.035 (dd, 1H, J=7.6, 1.6 Hz), 6.940 (t, 1H, J=7.6 Hz), 6.605 (d, 1H, J=10.0 Hz), 6.603 (d, 1H, J=8.8 Hz), 6.147 (d, 1H, J=8.8 Hz), 6.136 (s, 1H), 5.536 (d, 1H, J=10.0 Hz), 5.113 (s, 2H), 3.757 (s, 3H), 3.377 (s, 3H), 1.376 (s, 6H).

$^{13}$C-NMR (CDCl$_3$): 168.902, 155.066, 154.906, 150.589, 135.977, 131.065, 130.067, 129.723, 128.882, 128.364, 125.824, 122.271, 116.345, 114.951, 114.730, 109.460, 109.101, 94.793, 76.144, 55.986, 52.340, 27.834.

(2) Preparation of 2-(2-(methoxymethoxy)phenyl)-3-(2,2-dimethyl-5-hydroxy-2H-1-benzopyran-6-yl) propan-1-ol 3.96 g (10.0 mmol) of methyl 2-(2-(methoxymethoxy) phenyl)-3-(2,2-dimethyl-5-hydroxy-2H-1-benzopyran-6-yl) acrylate obtained in (1) was dissolved in 20 ml of THF, 60 ml of a 1.0 M LiBH$_4$ in THF solution was added thereto, and the resulting solution was refluxed for 5 hours. After the reaction solution was cooled in an ice bath, 50 ml of 1N HCl was slowly added thereto, and then extraction was performed using 100 ml of CH$_2$Cl$_2$. The organic layer was dried using anhydrous magnesium sulfate, and then distilled under reduced pressure for concentration. The concentrate was purified by silica gel column chromatography to obtain 2.42 g (6.53 mmol) of 2-(2-(methoxymethoxy)phenyl)-3-(2,2-dimethyl-5-hydroxy-2H-1-benzopyran-6-yl) propan-1-ol. (Yield: 65%)

$^1$H-NMR (CDCl$_3$): 7.621 (b, 1H), 7.366 (td, 1H, J=8.0, 1.6 Hz), 7.228 (d, 1H, J=8.0 Hz), 7.160 (dd, 1H, J=7.6, 1.6 Hz), 7.036 (t, 1H, J=7.6 Hz), 6.773 (d, 1H, J=10.0 Hz), 6.739 (d, 1H, J=8.0 Hz), 6.333 (d, 1H, J=8.0 Hz), 5.583 (d, 1H, J=10.0 Hz), 5.245 (s, 2H), 3.866 (dd, 1H, J=10.8, 4.0 Hz), 3.810 (dd, 1H, J=10.8, 2.8 Hz), 3.494 (s, 3H), 3.398 (m, 1H), 3.070 (dd, 1H, J=14.4, 10.4 Hz), 2.741 (dd, 1H, J=14.4, 4.0 Hz), 1.433 (s, 3H), 1.420 (s, 3H).

$^{13}$C-NMR (CDCl$_3$): 154.418, 152.473, 150.851, 131.444, 130.606, 128.825, 128.015, 127.881, 122.053, 117.835, 117.451, 114.135, 110.286, 108.500, 94.599, 75.540, 63.321, 56.333, 41.798, 30.759, 27.802, 27.585.

(3) Preparation of 3-(2-(methoxymethoxy)phenyl)-8,8-dimethyl-2,3,4,8-tetrahydropyrano [2,3-f] chromen {2'-(methoxymethoxy)-4'-deoxyglabridin}

0.995 g (3.80 mmol) of triphenylphosphine (Ph$_3$P) was added to a solution obtained by dissolving 1.31 g (3.53 mmol) of 2-(2-(methoxymethoxy)phenyl)-3-(2,2-dimethyl-5-hydroxy-2H-1-benzopyran-6-yl) propan-1-ol obtained in (2) in 10 ml of THF, and the resulting solution was heated to slowly reflux THF. 3.8 ml of a 1.0 M toluene solution of diethyl azodicarboxylate (DEAD) was slowly added thereto while this reflux condition, and the resulting solution was vigorously stirred for 1 hour. The reaction solution was cooled to room temperature, distilled under reduced pressure for concentration, and then purified by silica gel column chromatography to obtain 1.14 g (3.24 mmol) of 3-(2-(methoxymethoxy)phenyl)-8,8-dimethyl-2,3,4,8-tetrahydropyrano [2,3-f] chromene. (Yield: 92%)

$^1$H-NMR (CDCl$_3$): 7.231 (td, 1H, J=7.2, 1.6 Hz), 7.13~7.17 (m, 2H), 7.010 (td, 1H, J=7.2, 0.8 Hz), 6.847 (d, 1H, J=8.0 Hz), 6.677 (d, 1H, J=10.0 Hz), 6.396 (d, 1H, J=8.0 Hz), 5.578 (d, 1H, J=10.0 Hz), 5.235 (s, 2H), 4.408 (ddd, 1H, J=10.4, 2.4, 1.2 Hz), 4.058 (t, 1H, J=10.4 Hz), 3.702 (m, 1H), 3.491 (s, 3H), 3.015 (dd, 1H, J=15.2, 11.2 Hz), 2.881 (ddd, 1H, J=15.2, 3.6, 1.6 Hz), 1.447 (s, 3H), 1.426 (s, 3H).

$^{13}$C-NMR (CDCl$_3$): 155.027, 151.925, 149.737, 130.100, 129.161, 128.933, 127.885, 127.229, 121.987, 116.912, 114.337, 114.066, 109.896, 108.692, 94.419, 75.557, 70.069, 56.135, 32.114, 30.721, 27.798, 27.511.

(4) Preparation of 3-(2-(hydroxy)phenyl)-8,8-dimethyl-2,3,4,8-tetrahydropyrano [2,3-f] chromene 7.05 g (20.0 mmol) of 3-(2-(methoxymethoxy)phenyl)-8,8-dimethyl-2,3,4,8-tetrahydropyrano [2,3-f] chromene obtained in (3) was dissolved in 80 ml of isopropanol, 0.3 ml of concentrated hydrochloric acid was added thereto, and the resulting solution was stirred for 5 hours. The reaction solution was distilled under reduced pressure for concentration, and then purified by silica gel column chromatography to obtain 2.82 g (9.16 mol) of 3-(2-(hydroxy)phenyl)-8,8-dimethyl-2,3,4,8-tetrahydropyrano [2,3-f] chromene. (Yield: 46%)

$^1$H-NMR (CDCl$_3$): 7.11~7.16 (m, 2H), 6.933 (dt, 1H, J=7.6, 1.2 Hz), 6.848 (d, 1H, J=8.4 Hz), 6.759 (dd, 1H, J=8.0, 0.8 Hz), 6.676 (d, 1H, J=10.0 Hz), 6.398 (d, 1H, J=8.4 Hz), 5.578 (d, 1H, J=10.0 Hz), 5.059 (s, 1H), 4.434 (ddd, 1H, J=10.4, 3.2, 2.0 Hz), 4.087 (t, 1H, J=10.4 Hz), 3.607 (m, 1H), 3.037 (dd, 1H, J=15.2, 10.8 Hz), 2.904 (ddd, 1H, J=15.2, 5.2, 1.6 Hz), 1.449 (s, 3H), 1.431 (s, 3H).

$^{13}$C-NMR (CDCl$_3$): 153.405, 151.802, 149.721, 129.190, 128.943, 127.792, 127.617, 127.557, 121.128, 116.934, 115.417, 114.335, 109.935, 108.720, 75.659, 69.781, 32.202, 30.388, 27.732, 27.490.

(5) Preparation of 3-(2-hydroxyphenyl)-8,8-dimethyl-2,3,4,8,9,10-hexahydropyrano [2,3-f] chromene 2.82 g (9.16 mol) of 3-(2-(hydroxy)phenyl)-8,8-dimethyl-2,3,4,8-tetrahydropyrano [2,3-f] chromene obtained in (4) was put into 100 ml of a pressure vessel, and was well dissolved by adding 20 ml of ethanol, and then the solution was vigorously stirred under hydrogen at 2 atm for 15 hours while 100 mg of 10% Pd/C was mixed. The reaction solution was filtered to remove the catalyst, distilled under reduced pressure for concentration, and then purified by silica gel column chromatography to obtain 2.78 g (8.97 mmol) of 3-(2-hydroxyphenyl)-8,8-dimethyl-2,3,4,8,9,10-hexahydropyrano [2,3-f] chromene (Compound 2). (Yield=98%)

$^1$H-NMR (CDCl$_3$): 7.218 (t, 1H, J=7.6 Hz), 6.842 (d, 1H, 8.4 Hz), 6.813 (d, 1H, 7.6 Hz), 6.751 (dd, 1H, J=7.6, 2.0 Hz), 6.652 (d, 1H, J=2.0 Hz), 6.419 (d, 1H, J=8.4 Hz), 5.330 (s, 1H), 4.366 (ddd, 1H, J=10.4, 3.6, 0.4 Hz), 3.936 (t, 1H, J=10.4 Hz), 3.128 (m, 1H), 2.903 (d, 2H, J=8.4 Hz), 2.667 (m, 2H), 1.794 (t, 2H, J=7.2 Hz), 1.361 (s, 3H), 1.338 (s, 3H).

$^{13}$C-NMR (CDCl$_3$): 155.875, 152.714, 151.978, 143.459, 129.903, 127.478, 119.797, 114.227, 113.953, 112.644, 109.480, 109.428, 74.053, 70.774, 38.666, 32.296, 32.034, 26.880, 26.222, 17.116.

Example 2: Synthesis of 3-(2-hydroxy-4-methylphenyl)-8,8-dimethyl-2,3,4,8,9,10-hexahydropyrano [2,3-f] chromene (Compound 3)

(1) Preparation of Methyl 2-(2-benzyloxy-4-methylphenyl)-3-(2,2-dimethyl-5-hydroxy-2H-1-benzopyran-6-yl) acrylate 45 ml of a 1.0 M LDA in THF solution was added to a 3-necked round flask while being maintained under nitrogen atmosphere, and the flask was cooled in a dry ice-acetone bath at −78° C. 8.10 g (30.0 mmol) of (methyl 2-benzyloxy-4-methylphenyl) acetate prepared in Preparation Example 5 was dissolved in 150 ml of THF, and the resulting solution was slowly added to the 1.0 M LDA in THF solution previously prepared for 30 minutes, and further stirred for 30 minutes. A solution obtained by dissolving 9.24 g (30.0 mmol) of 5-benzoyloxy-2,2-dimethyl-6-formyl-2H-1-benzopyran prepared in Preparation Example 3 in 20 ml of THF was slowly added to the reaction solution previously prepared over 30 minutes, and then further stirred for 30 minutes. The round flask was separated from the dry ice acetone bath and left to stand to slowly heat the reaction solution to 0° C. At this state, 100 ml of brine was added thereto, and the resulting solution was vigorously stirred at room temperature for 30 minutes. The organic layer was separated, and then the aqueous layer was further extracted using 200 ml of ethyl acetate. The organic layer thus extracted with ethyl acetate was combined with the organic layer previously separated, and the resulting mixture was dried over anhydrous magnesium sulfate, and then distilled under reduced pressure for concentration. The concentrate was purified by silica gel column chromatography to obtain 5.79 g (12.70 mmol) of methyl 2-(2-benzyloxy-4-methylphenyl)-3-(2,2-dimethyl-5-hydroxy-2H-1-benzopyran-6-yl) acrylate. (Yield: 42.3%)

$^1$H-NMR (CDCl$_3$): 7.879 (s, 1H), 7.26~7.36 (m, 5H), 6.932 (d, 1H, J=7.6 Hz), 6.806 (s, 1H), 6.712 (d, 1H, J=7.6 Hz), 6.680 (d, 1H, J=8.4 Hz), 6.585 (d, 1H, J=10.0 Hz), 6.183 (d, 1H, J=8.4 Hz), 5.701 (s, 1H), 5.533 (d, 1H, J=10.0 Hz), 5.037 (s, 2H), 3.696 (s, 3H), 2.345 (s, 3H), 1.392 (s, 6H).

$^{13}$C-NMR (CDCl$_3$): 168.893, 156.193, 154.704, 150.259, 139.893, 136.992, 135.674, 130.963, 130.160, 128.842, 128.721, 127.668, 126.965, 122.024, 121.948, 116.543, 114.971, 113.332, 109.470, 109.040, 76.115, 70.023, 52.253, 27.872, 21.790.

(2) Preparation of 2-(2-benzyloxy-4-methylphenyl)-3-(2,2-dimethyl-5-hydroxy-2H-1-benzopyran-6-yl) propan-1-ol 4.56 g (10.0 mmol) of methyl 2-(2-benzyloxy-4-methylphenyl)-3-(2,2-dimethyl-5-hydroxy-2H-1-benzopyran-6-yl) acrylate was dissolved in 20 ml of THF, 60 ml of a 1.0 M LiBH$_4$ in THF solution was added thereto, and the resulting solution was refluxed for 5 hours. After the reaction solution was cooled in an ice bath, 50 ml of 1N HCl was slowly added thereto, and then extraction was performed using 100 ml of CH$_2$Cl$_2$. The organic layer was dried using anhydrous magnesium sulfate, distilled under reduced pressure for concentration, and purified by silica gel column chromatography to obtain 2.35 g (5.47 mmol) of 2-(2-benzyloxy-4-methylphenyl)-3-(2,2-dimethyl-5-hydroxy-2H-1-benzopyran-6-yl) propan-1-ol. (Yield: 54.7%)

$^1$H-NMR (CDCl$_3$): 7.687 (b, 1H), 7.33~7.43 (m, 5H), 7.158 (d, 1H, J=7.6 Hz), 6.845 (s, 1H), 6.807 (d, 1H, J=7.6 Hz), 6.737 (d, 1H, J=10.0 Hz), 6.707 (d, 1H, J=8.0 Hz), 6.309 (d, 1H, J=8.0 Hz), 5.562 (d, 1H, J=10.0 Hz), 5.105 (s, 2H), 3.845 (dd, 1H, J=10.8, 3.6 Hz), 3.737 (dd, 1H, J=10.8, 2.8 Hz), 3.323 (m, 1H), 3.118 (dd, 1H, J=14.0, 10.4 Hz), 2.702 (dd, 1H, J=14.0, 4.0 Hz), 2.360 (s, 3H), 1.431 (s, 3H), 1.410 (s, 3H).

$^{13}$C-NMR (CDCl$_3$): 155.793, 152.415, 150.979, 137.841, 136.457, 130.688, 128.734, 128.596, 128.429, 128.333, 128.231, 127.633, 121.824, 118.070, 117.591, 113.116, 110.289, 108.436, 75.478, 70.517, 63.463, 42.569, 30.581, 27.910, 27.575, 21.394.

(3) Preparation of 3-(2-benzyloxy-4-methylphenyl)-8,8-dimethyl-2,3,4,8-tetrahydropyrano [2,3-f] chromene 0.995 g (3.80 mmol) of triphenylphosphine ($Ph_3P$) was added to a solution obtained by dissolving 1.57 g (3.65 mmol) of 2-(2-benzyloxy-4-methylphenyl)-3-(2,2-dimethyl-5-hydroxy-2H-1-benzopyran-6-yl) propan-1-ol obtained in (2) in 10 ml of THF, and the resulting solution was heated to slowly reflux THF. 3.9 ml of a 1.0 M diethyl azodicarboxylate (DEAD) in toluene solution was slowly added thereto while the state was maintained, and the resulting solution was vigorously stirred for 1 hour. The reaction solution was cooled to room temperature, distilled under reduced pressure for concentration, and then purified by silica gel column chromatography to obtain 1.31 g (3.17 mmol) of 3-(2-benzyloxy-4-methylphenyl)-8,8-dimethyl-2,3,4,8-tetrahydropyrano [2,3-f] chromene. (Yield: 86.8%)

$^1$H-NMR ($CDCl_3$): 7.32~7.45 (m, 5H), 7.052 (d, 1H, J=7.2 Hz), 6.838 (d, 1H, J=8.0 Hz), 6.811 (s, 1H), 6.796 (d, 1H, J=7.2 Hz), 6.666 (d, 1H, J=10.0 Hz), 6.384 (d, 1H, J=8.0 Hz), 5.567 (d, 1H, J=10.0 Hz), 5.116 (s, 2H), 4.394 (ddd, 1H, J=10.0, 3.2, 2.0 Hz), 4.059 (t, 1H, J=10.0 Hz), 3.717 (m, 1H), 2.991 (dd, 1H, J=14.0, 6.8 Hz), 2.894 (dd, 1H, J=14.0, 5.2 Hz), 2.348 (s, 3H), 1.446 (s, 3H), 1.432 (s, 3H).

$^{13}$C-NMR ($CDCl_3$): 156.291, 151.838, 149.853, 137.757, 137.128, 129.167, 128.775, 128.592, 127.814, 127.112, 126.958, 121.666, 116.989, 114.446, 112.924, 109.849, 108.577, 75.527, 70.115, 70.065, 31.587, 30.704, 27.784, 27.594, 21.426.

(4) Preparation of 3-(2-hydroxy-4-methylphenyl)-8,8-dimethyl-2,3,4,8,9,10-hexahydropyrano [2,3-f] chromene 4.12 g (10.0 mol) of 3-(2-benzyloxy-4-methylphenyl)-8,8-dimethyl-2,3,4,8-tetrahydropyrano [2,3-f] chromene obtained in (3) was put into 100 ml of a pressure vessel, and was well dissolved by adding 50 ml of ethanol, and then the solution was vigorously stirred under hydrogen at 5 atm and room temperature for 25 hours while 150 mg of 5% Pd/C was mixed. The reaction solution was filtered to remove the catalyst, distilled under reduced pressure for concentration, and then purified by silica gel column chromatography to obtain 2.67 g (8.23 mmol) of 3-(2-hydroxy-4-methylphenyl)-8,8-dimethyl-2,3,4,8,9,10-hexahydropyrano [2,3-f] chromene (Compound 3). (Yield=82%)

$^1$H-NMR ($CDCl_3$): 7.017 (d, 1H, J=8.0 Hz), 6.850 (d, 1H, J=7.6 Hz), 6.755 (dd, 1H, J=7.6, 0.4 Hz), 6.593 (d, 1H, J=0.4 Hz), 6.407 (d, 1H, J=8.0 Hz), 4.931 (s, 1H), 4.422 (ddd, 1H, J=10.4, 3.6, 2.0 Hz), 4.058 (t, 1H, J=10.4 Hz), 3.556 (m, 1H), 3.044 (dd, 1H, J=15.6, 11.2 Hz), 2.890 (ddd, 1H, J=15.6, 5.2, 2.0 Hz), 2.657 (m, 2H, J=6.8, 2.4 Hz), 2.294 (s, 3H), 1.809 (t, 2H, J=6.8 Hz), 1.351 (s, 3H), 1.337 (s, 3H).

$^{13}$C-NMR ($CDCl_3$): 153.271, 152.801, 152.130, 137.818, 127.458, 127.414, 124.618, 121.826, 116.214, 112.830, 109.315, 109.274, 73.743, 69.904, 32.337, 32.050, 30.577, 26.807, 26.408, 20.920, 17.132.

Example 3: Synthesis of 3-(2-hydroxy-4-ethylphenyl)-8,8-dimethyl-2,3,4,8,9,10-hexahydropyrano [2,3-f] chromene (Compound 4)

(1) Preparation of methyl 2-(2-benzyloxy-4-ethylphenyl)-3-(2,2-dimethyl-5-hydroxy-2H-1-benzopyran-6-yl) acrylate Methyl 2-(2-benzyloxy-4-ethylphenyl)-3-(2,2-dimethyl-5-hydroxy-2H-1-benzopyran-6-yl) acrylate was obtained in the same manner as in Example 2(1), except that (methyl 2-benzyloxy-4-ethylphenyl) acetate prepared in Preparation Example 6 was used instead of (methyl 2-benzyloxy-4-methylphenyl) acetate.

$^1$H-NMR ($CDCl_3$): 7.889 (s, 1H), 7.26~7.36 (m, 5H), 6.957 (d, 1H, J=7.6 Hz), 6.882 (s, 1H), 6.740 (d, 1H, J=7.6 Hz), 6.657 (d, 1H, J=8.4 Hz), 6.589 (d, 1H, J=10.0 Hz), 6.170 (d, 1H, J=8.4 Hz), 5.789 (s, 1H), 5.534 (d, 1H, J=10.0 Hz), 5.045 (s, 2H), 3.696 (s, 3H), 2.645 (q, 2H, J=7.6 Hz), 1.391 (s, 6H), 1.233 (t, 3H, J=7.6 Hz).

$^{13}$C-NMR ($CDCl_3$): 168.965, 156.246, 154.681, 150.298, 146.182, 137.036, 135.651, 131.006, 130.842, 130.202, 128.874, 128.272, 127.674, 126.938, 122.123, 120.702, 116.555, 115.022, 112.147, 109.477, 109.025, 76.132, 70.033, 52.294, 28.988, 27.880, 15.164.

(2) Preparation of 2-(2-benzyloxy-4-ethylphenyl)-3-(2,2-dimethyl-5-hydroxy-2H-1-benzopyran-6-yl) propan-1-ol 2-(2-benzyloxy-4-ethylphenyl)-3-(2,2-dimethyl-5-hydroxy-2H-1-benzopyran-6-yl) propan-1-ol was obtained in the same manner as in Example 2(2), except that methyl 2-(2-benzyloxy-4-ethylphenyl)-3-(2,2-dimethyl-5-hydroxy-2H-1-benzopyran-6-yl) acrylate obtained in (1) was used instead of methyl 2-(2-benzyloxy-4-methyl phenyl)-3-(2,2-dimethyl-5-hydroxy-2H-1-benzopyran-6-yl) acrylate.

$^1$H-NMR ($CDCl_3$): 7.33~7.45 (m, 5H), 7.198 (d, 1H, J=7.6 Hz), 6.875 (s, 1H), 6.841 (d, 1H, J=7.6 Hz), 6.749 (d, 1H, J=10.0 Hz), 6.717 (d, 1H, J=8.0 Hz), 6.321 (d, 1H, J=8.0 Hz), 5.568 (d, 1H, J=10.0 Hz), 5.125 (s, 2H), 3.852 (dd, 1H, J=10.8, 3.6 Hz), 3.733 (dd, 1H, J=10.8, 2.8 Hz), 3.328 (m, 1H), 3.132 (dd, 1H, J=14.0, 10.4 Hz), 2.712 (dd, 1H, J=14.0, 4.0 Hz), 2.662 (q, 2H, J=4.4 Hz), 1.441 (s, 3H), 1.417 (s, 3H), 1.263 (t, 3H, J=4.4 Hz)

$^{13}$C-NMR ($CDCl_3$): 155.799, 152.370, 150.984, 144.227, 136.439, 130.670, 128.711, 128.653, 128.578, 128.355, 128.217, 127.661, 120.499, 118.115, 117.587, 111.897, 110.281, 108.412, 75.465, 70.476, 63.352, 42.565, 30.497, 28.755, 27.899, 27.538, 15.477.

(3) Preparation of 3-(2-benzyloxy-4-ethylphenyl)-8,8-dimethyl-2,3,4,8-tetrahydropyrano [2,3-f] chromene 3-(2-benzyloxy-4-ethylphenyl)-8,8-dimethyl-2,3,4,8-tetrahydropyrano [2,3-f] chromene was obtained in the same manner as in Example 2(3), except that 2-(2-benzyloxy-4-ethylphenyl)-3-(2,2-dimethyl-5-hydroxy-2H-1-benzopyran-6-yl) propan-1-ol obtained in (2) was used instead of 2-(2-benzyloxy-4-methylphenyl)-3-(2,2-dimethyl-5-hydroxy-2H-1-benzopyran-6-yl) propan-1-ol.

$^1$H-NMR ($CDCl_3$): 7.32~7.45 (m, 5H), 7.081 (d, 1H, J=8.0 Hz), 6.82~6.86 (m, 3H), 6.663 (d, 1H, J=10.0 Hz), 6.384 (d, 1H, J=8.0 Hz), 5.568 (d, 1H, J=10.0 Hz), 5.128 (s, 2H), 4.402 (m, 1H), 4.062 (t, 1H, J=10.4 Hz), 3.724 (m, 1H), 2.997 (dd, 1H, J=15.6, 10.2 Hz), 2.890 (dd, 1H, J=15.6, 3.2 Hz), 2.642 (q, 2H, J=6.8 Hz), 1.446 (s, 3H), 1.431 (s, 3H), 1.246 (t, 3H, J=6.8 Hz).

$^{13}$C-NMR ($CDCl_3$): 156.322, 151.802, 149.827, 144.159, 137.124, 129.167, 128.791, 128.578, 127.807, 127.150, 127.069, 120.340, 116.970, 114.463, 111.727, 109.835, 108.551, 75.526, 70.103, 70.036, 31.571, 30.686, 28.799, 27.772, 27.566, 15.474.

(4) Preparation of 3-(2-hydroxy-4-ethylphenyl)-8,8-dimethyl-2,3,4,8,9,10-hexahydropyrano [2,3-f] chromene 3-(2-hydroxy-4-ethylphenyl)-8,8-dimethyl-2,3,4,8,9,10-hexahydropyrano [2,3-f] chromene (Compound 4) was obtained in the same manner as in Example 2(4), except that 3-(2-benzyloxy-4-ethylphenyl)-8,8-dimethyl-2,3,4,8-tetrahydropyrano [2,3-f] chromene obtained in (3) was used instead of 3-(2-benzyloxy-4-methylphenyl)-8,8-dimethyl-2,3,4,8-tetrahydropyrano [2,3-f] chromene.

$^1$H-NMR (CDCl$_3$): 7.054 (d, 1H, J=8.0 Hz), 6.860 (d, 1H, J=8.0 Hz), 6.789 (d, 1H, J=8.0 Hz), 6.616 (s, 1H), 6.421 (d, 1H, J=8.0 Hz), 5.097 (s, 1H), 4.443 (m, 1H), 4.069 (t, 1H, J=10.4 Hz), 3.567 (m, 1H), 3.059 (dd, 1H, J=15.6, 11.2 Hz), 2.901 (m, 1H), 2.596 (q, 2H, J=6.8 Hz), 1.802 (t, 2H, J=6.8 Hz), 1.809 (t, 2H, J=6.8 Hz), 1.362 (s, 3H), 1.347 (s, 3H), 1.231 (t, 3H, J=6.8 Hz).

$^{13}$C-NMR (CDCl$_3$): 153.373, 152.716, 152.102, 144.205, 127.472, 127.415, 124.773, 120.499, 114.963, 112.898, 109.310, 109.248, 73.795, 69.897, 32.308, 32.054, 30.532, 28.276, 26.784, 26.374, 17.120, 15.308.

Example 4: Synthesis of 3-(2-hydroxy-4-propylphenyl)-8,8-dimethyl-2,3,4,8,9,10-hexahydropyrano [2,3-f] chromene (Compound 5)

(1) Preparation of methyl 2-(2-benzyloxy-4-propylphenyl)-3-(2,2-dimethyl-5-hydroxy-2H-1-benzopyran-6-yl) acrylate Methyl 2-(2-benzyloxy-4-propylphenyl)-3-(2,2-dimethyl-5-hydroxy-2H-1-benzopyran-6-yl) acrylate was obtained in the same manner as in Example 2(1), except that (methyl 2-benzyloxy-4-propylphenyl) acetate prepared in Preparation Example 7 was used instead of (methyl 2-benzyloxy-4-methylphenyl) acetate.

$^1$H-NMR (CDCl$_3$): 7.902 (s, 1H), 7.26~7.36 (m, 5H), 6.952 (d, 1H, J=7.6 Hz), 6.803 (s, 1H), 6.719 (d, 1H, J=7.6 Hz), 6.636 (d, 1H, J=8.8 Hz), 6.589 (d, 1H, J=10.0 Hz), 6.156 (d, 1H, J=8.8 Hz), 5.835 (s, 1H), 5.531 (d, 1H, J=10.0 Hz), 5.041 (s, 2H), 3.699 (s, 3H), 2.578 (t, 2H, J=7.2 Hz), 1.641 (m, 2H, J=7.2 Hz), 1.392 (s, 6H), 0.920 (t, 3H, J=7.2 Hz).

$^{13}$C-NMR (CDCl$_3$): 169.056, 156.132, 154.677, 150.477, 144.567, 137.010, 135.689, 130.894, 130.144, 128.652, 128.542, 128.368, 127.617, 126.983, 122.191, 121.353, 116.536, 115.058, 112.732, 109.488, 108.916, 76.091, 69.985, 52.257, 38.120, 27.833, 24.166, 13.678.

(2) Preparation of 2-(2-benzyloxy-4-propylphenyl)-3-(2,2-dimethyl-5-hydroxy-2H-1-benzopyran-6-yl) propan-1-ol 2-(2-benzyloxy-4-propylphenyl)-3-(2,2-dimethyl-5-hydroxy-2H-1-benzopyran-6-yl) propan-1-ol was obtained in the same manner as in Example 2(2), except that methyl 2-(2-benzyloxy-4-propylphenyl)-3-(2,2-dimethyl-5-hydroxy-2H-1-benzopyran-6-yl) acrylate obtained in (1) was used instead of methyl 2-(2-benzyloxy-4-methyl phenyl)-3-(2,2-dimethyl-5-hydroxy-2H-1-benzopyran-6-yl) acrylate.

$^1$H-NMR (CDCl$_3$): 7.721 (s, 1H), 7.33~7.45 (m, 5H), 7.189 (d, 1H, J=8.0 Hz), 6.859 (s, 1H), 6.824 (d, 1H, J=8.0 Hz), 6.761 (d, 1H, J=10.0 Hz), 6.715 (d, 1H, J=8.4 Hz), 6.329 (d, 1H, J=8.4 Hz), 5.575 (d, 1H, J=10.0 Hz), 5.126 (s, 2H), 3.858 (m, 1H), 3.743 (m, 1H), 3.339 (m, 1H), 3.132 (dd, 1H, J=14.0, 10.4 Hz), 2.728 (dd, 1H, J=14.0, 4.4 Hz), 2.605 (t, 2H, J=7.6 Hz), 1.676 (m, 2H, J=7.6 Hz), 1.450 (s, 3H), 1.429 (s, 3H), 0.982 (t, 3H, J=7.2 Hz)

$^{13}$C-NMR (CDCl$_3$): 155.670, 152.304, 150.940, 142.630, 136.425, 130.674, 128.675, 128.583, 128.564, 128.192, 128.173, 127.629, 121.125, 118.119, 117.563, 112.389, 110.255, 108.386, 75.452, 70.407, 63.289, 42.432, 37.925, 30.462, 27.859, 27.512, 24.455, 13.840.

(3) Preparation of 3-(2-benzyloxy-4-propylphenyl)-8,8-dimethyl-2,3,4,8-tetrahydropyrano [2,3-f] chromene 3-(2-benzyloxy-4-propylphenyl)-8,8-dimethyl-2,3,4,8-tetrahydropyrano [2,3-f] chromene was obtained in the same manner as in Example 2(3), except that 2-(2-benzyloxy-4-propylphenyl)-3-(2,2-dimethyl-5-hydroxy-2H-1-benzopyran-6-yl) propan-1-ol obtained in (2) was used instead of 2-(2-benzyloxy-4-methylphenyl)-3-(2,2-dimethyl-5-hydroxy-2H-1-benzopyran-6-yl) propan-1-ol.

$^1$H-NMR (CDCl$_3$): 7.32~7.47 (m, 5H), 7.088 (d, 1H, J=8.0 Hz), 6.869 (d, 1H, J=8.0 Hz), 8.833 (s, 1H), 6.820 (d, 1H, J=8.0 Hz), 6.695 (d, 1H, J=10.4 Hz), 6.409 (d, 1H, J=8.0 Hz), 5.589 (d, 1H, J=10.4 Hz), 5.142 (s, 2H), 4.421 (m, 1H), 4.079 (t, 1H, J=10.4 Hz), 3.743 (m, 1H), 3.008 (dd, 1H, J=15.6, 11.2 Hz), 2.914 (m, 1H, J=15.6, 3.2 Hz), 2.595 (t, 2H, J=7.2 Hz), 1.668 (m, 2H, J=7.2 Hz), 1.469 (s, 3H), 1.454 (s, 3H), 0.980 (t, 3H, J=7.2 Hz).

$^{13}$C-NMR (CDCl$_3$): 156.250, 151.832, 149.850, 142.593, 137.148, 129.164, 128.756, 128.563, 127.790, 127.144, 127.031, 127.031, 121.034, 116.993, 114.471, 112.342, 109.836, 108.556, 75.509, 70.122, 70.070, 38.008, 31.627, 30.718, 27.785, 27.583, 24.437, 13.858.

(4) Preparation of 3-(2-hydroxy-4-propylphenyl)-8,8-dimethyl-2,3,4,8,9,10-hexahydropyrano [2,3-f] chromene 3-(2-hydroxy-4-propylphenyl)-8,8-dimethyl-2,3,4,8,9,10-hexahydropyrano [2,3-f] chromene (Compound 5) was obtained in the same manner as in Example 2(4), except that 3-(2-benzyloxy-4-propylphenyl)-8,8-dimethyl-2,3,4,8-tetrahydropyrano [2,3-f] chromene obtained in (3) was used instead of 3-(2-benzyloxy-4-methylphenyl)-8,8-dimethyl-2,3,4,8-tetrahydropyrano [2,3-f] chromene.

$^1$H-NMR (CDCl$_3$): 7.029 (d, 1H, J=8.0 Hz), 6.842 (d, 1H, J=8.0 Hz), 6.755 (d, 1H, J=8.0 Hz), 6.597 (s, 1H), 6.390 (d, 1H, J=8.4 Hz), 4.804 (s, 1H), 4.423 (m, 1H, J=10.4, 2.4 Hz), 4.046 (t, 1H, J=10.4 Hz), 3.537 (m, 1H), 3.042 (dd, 1H, J=15.6, 11.2 Hz), 2.886 (m, 1H), 2.652 (m, 2H), 2.518 (t, 2H, J=7.6 Hz), 1.781 (t, 2H, J=6.8 Hz), 1.612 (m, 2H, J=7.2 Hz), 1.338 (s, 3H), 1.323 (s, 3H), 0.947 (t, 3H, J=7.2 Hz).

$^{13}$C-NMR (CDCl$_3$): 153.296, 152.802, 152.143, 142.679, 127.463, 127.331, 124.838, 121.188, 115.572, 112.888, 109.322, 109.286, 73.749, 69.933, 37.502, 32.366, 32.149, 30.605, 26.809, 26.411, 24.276, 17.141, 13.846.

Example 5: Synthesis of 3-(2-hydroxy-4-isopropylphenyl)-8,8-dimethyl-2,3,4,8,9,10-hexahydropyrano [2,3-f] chromene (Compound 6)

3-(2-hydroxy-4-isopropylphenyl)-8,8-dimethyl-2,3,4,8,9,10-hexahydropyrano [2,3-f] chromene (Compound 6) was obtained in the same manner as in Example 2, except that (methyl 2-benzyloxy-4-isopropyl-phenyl) acetate was used instead of (methyl 2-benzyloxy-4-methylphenyl) acetate.

$^1$H-NMR (CDCl$_3$): 7.058 (d, 1H, J=8.0 Hz), 6.853 (d, 1H, J=8.0 Hz), 6.812 (dd, 1H, J=8.0, 1.2 Hz), 6.641 (d, 1H, J=1.2

Hz), 6.408 (d, 1H, J=8.0 Hz), 4.973 (s, 1H), 4.444 (m, 1H, J=10.4, 3.2, 2.0 Hz), 4.060 (t, 1H, J=10.4 Hz), 3.552 (m, 1H), 3.056 (dd, 1H, J=15.6, 11.2 Hz), 2.892 (m, 1H, J=15.6, 5.2, 1.6 Hz), 2.859 (m, 1H, J=6.8 Hz), 2.668 (m, 2H), 1.794 (t, 2H, J=6.8 Hz), 1.352 (s, 3H), 1.337 (s, 3H), 1.235 (d, 6H, J=6.8 Hz).
$^{13}$C-NMR (CDCl$_3$): 153.331, 152.780, 152.123, 148.947, 127.471, 127.408, 124.870, 119.166, 113.559, 112.857, 109.310, 109.268, 73.751, 69.902, 33.597, 32.334, 32.124, 30.566, 26.813, 26.395, 23.853, 17.139.

Example 6: Synthesis of 3-(2-hydroxy-4-butyl)phenyl)-8,8-dimethyl-2,3,4,8,9,10-hexahydropyrano [2,3-f] chromene (Compound 7)

(1) Preparation of methyl 2-(2-benzyloxy-4-butylphenyl)-3-(2,2-dimethyl-5-hydroxy-2H-1-benzopyran-6-yl) acrylate Methyl 2-(2-benzyloxy-4-butylphenyl)-3-(2,2-dimethyl-5-hydroxy-2H-1-benzopyran-6-yl) acrylate was obtained in the same manner as in Example 2(1), except that (methyl 2-benzyloxy-4-butylphenyl) acetate prepared in Preparation Example 8 was used instead of (methyl 2-benzyloxy-4-methylphenyl) acetate.
$^1$H-NMR (CDCl$_3$): 7.879 (s, 1H), 7.26~7.36 (m, 5H), 6.934 (d, 1H, J=7.6 Hz), 6.791 (s, 1H), 6.711 (d, 1H, J=7.6 Hz), 6.631 (d, 1H, J=8.8 Hz), 6.572 (d, 1H, J=10.0 Hz), 6.151 (d, 1H, J=8.8 Hz), 5.835 (s, 1H), 5.525 (d, 1H, J=10.0 Hz), 5.026 (s, 2H), 3.692 (s, 3H), 2.585 (t, 2H, J=7.2 Hz), 1.579 (m, 2H), 1.381 (s, 6H), 1.325 (m, 2H), 0.909 (t, 3H, J=7.2 Hz).
13C-NMR (CDCl$_3$): 169.031, 156.107, 154.715, 150.380, 144.868, 136.989, 135.667, 130.929, 130.174, 128.689, 128.451, 128.387, 127.656, 127.037, 122.061, 121.309, 116.561, 114.980, 112.704, 109.546, 108.977, 76.146, 70.034, 52.285, 35.796, 33.226, 27.857, 22.300, 14.054.

(2) Preparation of 2-(2-benzyloxy-4-butylphenyl)-3-(2,2-dimethyl-5-hydroxy-2H-1-benzopyran-6-yl) propan-1-ol 2-(2-benzyloxy-4-butylphenyl)-3-(2,2-dimethyl-5-hydroxy-2H-1-benzopyran-6-yl) propan-1-ol was obtained in the same manner as in Example 2(2), except that methyl 2-(2-benzyloxy-4-butylphenyl)-3-(2,2-dimethyl-5-hydroxy-2H-1-benzopyran-6-yl) acrylate obtained in (1) was used instead of methyl 2-(2-benzyloxy-4-methyl phenyl)-3-(2,2-dimethyl-5-hydroxy-2H-1-benzopyran-6-yl) acrylate.
$^1$H-NMR (CDCl$_3$): 7.422 (b, 1H), 7.33~7.45 (m, 5H), 7.161 (d, 1H, J=8.0 Hz), 6.827 (s, 1H), 6.797 (d, 1H, J=8.0 Hz), 6.723 (d, 1H, J=10.0 Hz), 6.697 (d, 1H, J=8.4 Hz), 6.296 (d, 1H, J=8.4 Hz), 5.547 (d, 1H, J=10.0 Hz), 5.101 (s, 2H), 3.837 (m, 1H), 3.718 (m, 1H), 3.295 (m, 1H), 3.107 (dd, 1H, J=14.0, 10.4 Hz), 2.689 (dd, 1H, J=14.0, 4.4 Hz), 2.591 (t, 2H, J=7.6 Hz), 1.588 (m, 2H, J=7.6 Hz), 1.417 (s, 3H), 1.394 (s, 3H), 1.350 (m, 2H), 0.930 (t, 3H, J=7.2 Hz)
$^{13}$C-NMR (CDCl$_3$): 155.716, 152.389, 151.010, 142.936, 136.424, 130.671, 128.723, 128.581, 128.275, 128.231, 127.680, 121.140, 118.095, 117.604, 112.428, 110.294, 108.422, 75.476, 70.476, 63.366, 42.697, 35.576, 33.545, 30.468, 27.915, 27.551, 22.360, 13.952.

(3) Preparation of 3-(2-benzyloxy-4-butylphenyl)-8,8-dimethyl-2,3,4,8-tetrahydropyrano [2,3-f] chromene 3-(2-benzyloxy-4-butylphenyl)-8,8-dimethyl-2,3,4,8-tetrahydropyrano [2,3-f] chromene was obtained in the same manner as in Example 2(3), except that 2-(2-benzyloxy-4-butylphenyl)-3-(2,2-dimethyl-5-hydroxy-2H-1-benzopyran-6-yl) propan-1-ol obtained in (2) was used instead of 2-(2-benzyloxy-4-methylphenyl)-3-(2,2-dimethyl-5-hydroxy-2H-1-benzopyran-6-yl) propan-1-ol.
$^1$H-NMR (CDCl$_3$): 7.32~7.45 (m, 5H), 7.064 (d, 1H, J=8.0 Hz), 6.837 (d, 1H, J=8.0 Hz), 8.808 (s, 1H), 6.798 (d, 1H, J=8.0 Hz), 6.667 (d, 1H, J=10.4 Hz), 6.381 (d, 1H, J=8.0 Hz), 5.567 (d, 1H, J=10.4 Hz), 5.124 (s, 2H), 4.402 (m, 1H), 4.057 (t, 1H, J=10.4 Hz), 3.728 (m, 1H), 2.996 (dd, 1H, J=15.6, 11.2 Hz), 2.885 (m, 1H, J=15.6, 3.2 Hz), 2.595 (t, 2H, J=7.2 Hz), 1.599 (m, 2H, J=7.2 Hz), 1.446 (s, 3H), 1.431 (s, 3H), 1.380 (m, 2H), 0.941 (t, 3H, J=7.2 Hz).
$^{13}$C-NMR (CDCl$_3$): 156.222, 151.797, 149.827, 142.813, 137.127, 129.165, 128.773, 128.563, 127.787, 127.146, 127.060, 127.028, 120.952, 116.973, 114.480, 112.247, 109.829, 108.540, 75.517, 70.112, 70.017, 35.609, 33.538, 31.573, 30.693, 27.772, 27.561, 22.368, 13.948.

(4) Preparation of 3-(2-hydroxy-4-butylphenyl)-8,8-dimethyl-2,3,4,8,9,10-hexahydropyrano [2,3-f] chromene 3-(2-hydroxy-4-butylphenyl)-8,8-dimethyl-2,3,4,8,9,10-hexahydropyrano [2,3-f] chromene (Compound 7) was obtained in the same manner as in Example 2(4), except that 3-(2-benzyloxy-4-butylphenyl)-8,8-dimethyl-2,3,4,8-tetrahydropyrano [2,3-f] chromene obtained in (3) was used instead of 3-(2-benzyloxy-4-methylphenyl)-8,8-dimethyl-2, 3,4,8-tetrahydropyrano [2,3-f] chromene.
$^1$H-NMR (CDCl$_3$): 7.033 (d, 1H, J=8.0 Hz), 6.851 (d, 1H, J=8.0 Hz), 6.761 (d, 1H, J=8.0 Hz), 6.596 (s, 1H), 6.407 (d, 1H, J=8.4 Hz), 4.904 (s, 1H), 4.434 (m, 1H, J=10.4, 2.4 Hz), 4.056 (t, 1H, J=10.4 Hz), 3.538 (m, 1H), 3.051 (dd, 1H, J=15.6, 11.2 Hz), 2.892 (m, 1H), 2.667 (m, 2H), 2.546 (t, 2H, J=7.6 Hz), 1.792 (t, 2H, J=6.8 Hz), 1.599 (m, 2H, J=7.2 Hz), 1.375 (m, 2H), 1.351 (s, 3H), 1.336 (s, 3H), 0.939 (t, 3H, J=7.2 Hz).
$^{13}$C-NMR (CDCl$_3$): 153.256, 152.765, 152.114, 142.906, 127.463, 127.331, 124.724, 121.142, 115.492, 112.866, 109.302, 109.253, 73.751, 69.910, 35.084, 33.380, 32.321, 32.085, 30.565, 26.805, 26.387, 22.351, 17.131, 13.932.

Example 7: Synthesis of 3-(2-hydroxy-4-n-pentylphenyl)-8,8-dimethyl-2,3,4,8,9,10-hexahydropyrano [2,3-f] chromene (Compound 8)

3-(2-hydroxy-4-n-pentylphenyl)-8,8-dimethyl-2,3,4,8,9, 10-hexahydropyrano [2,3-f] chromene (Compound 8) was obtained in the same manner as in Example 2, except that (methyl 2-benzyloxy-4-n-pentylphenyl) acetate was used instead of (methyl 2-benzyloxy-4-methylphenyl) acetate.
$^1$H-NMR (CDCl$_3$): 7.033 (d, 1H, J=8.0 Hz), 6.850 (d, 1H, J=8.0 Hz), 6.761 (dd, 1H, J=8.0, 1.2 Hz), 6.598 (d, 1H, J=1.2 Hz), 6.404 (d, 1H, J=8.0 Hz), 4.898 (s, 1H), 4.436 (m, 1H, J=10.4, 3.2, 2.0 Hz), 4.054 (t, 1H, J=10.4 Hz), 3.551 (m, 1H), 3.048 (dd, 1H, J=15.6, 11.2 Hz), 2.906 (m, 1H, J=15.6, 5.2, 1.6 Hz), 2.664 (m, 2H), 2.536 (t, 2H, J=4.4H), 1.790 (t, 2H, J=6.8 Hz), 1.599 (m, 2H), 1.35 (m, 4H), 1.348 (s, 3H), 1.333 (s, 3H), 0.908 (t, 3H, J=7.4 Hz).
$^{13}$C-NMR (CDCl$_3$): 153.255, 152.794, 152.125, 142.957, 127.457, 127.344, 124.740, 121.145, 115.485, 115.485, 112.842, 109.258, 73.726, 69.913, 35.383, 32.934, 32.483, 32.333, 32.103, 30.935, 30.581, 26.811, 26.399, 22.519, 17.134, 14.010.

Example 8: Synthesis of 3-(2-hydroxy-4-(2-methoxyethyl)phenyl)-8,8-dimethyl-2,3,4,8,9,10-hexahydropyrano [2,3-f] chromene (Compound 9)

3-(2-hydroxy-4-(2-methoxyethyl)phenyl)-8,8-dimethyl-2,3,4,8,9,10-hexahydropyrano [2,3-f] chromene (Compound 9) was obtained in the same manner as in Example 2, except that (methyl 2-benzyloxy-4-(2-methoxyethyl)phenyl) acetate was used instead of (methyl 2-benzyloxy-4-methylphenyl) acetate.

$^1$H-NMR (CDCl$_3$): 7.043 (d, 1H, J=8.0 Hz), 6.843 (d, 1H, J=8.0 Hz), 6.773 (dd, 1H, J=8.0, 2.0 Hz), 6.636 (d, 1H, J=2.0 Hz), 6.398 (d, 1H, J=8.0 Hz), 5.762 (s, 1H), 4.416 (m, 1H, J=10.4, 2.4 Hz), 4.035 (t, 1H, J=10.4 Hz), 3.647 (t, 2H, J=6.8 Hz) 3.549 (m, 1H), 3.391 (s, 3H), 3.033 (dd, 1H, J=15.6, 11.2 Hz), 2.864 (m, 1H, J=15.6, 5.2, 1.6 Hz), 2.831 (t, 2H, J=6.8 Hz) 2.654 (m, 2H), 1.783 (t, 2H, J=6.8H), 1.343 (s, 3H), 1.328 (s, 3H).

$^{13}$C-NMR (CDCl$_3$): 153.701, 152.748, 152.100, 138.669, 127.490, 127.449, 125.554, 121.052, 115.967, 112.828, 109.283, 109.227, 73.716, 73.396, 69.838, 58.624, 35.501, 32.294, 32.062, 30.413, 26.787, 26.381, 17.111.

Example 9: Synthesis of 3-(2-hydroxy-3,4-dimethylphenyl)-8,8-dimethyl-2,3,4,8,9,10-hexahydropyrano [2,3-f] chromene (Compound 10)

3-(2-hydroxy-3,4-dimethylphenyl)-8,8-dimethyl-2,3,4,8,9,10-hexahydropyrano [2,3-f] chromene (Compound 10) was obtained in the same manner as in Example 2, except that (methyl 2-benzyloxy-3,4-dimethylphenyl) acetate was used instead of (methyl 2-benzyloxy-4-methylphenyl) acetate.

$^1$H-NMR (CDCl$_3$): 6.901 (d, 1H, J=8.0 Hz), 6.857 (d, 1H, J=8.4 Hz), 6.790 (d, 1H, J=8.0 Hz), 6.411 (d, 1H, J=8.4 Hz), 4.834 (s, 1H), 4.430 (m, 1H, J=10.0, 3.2, 2.0 Hz), 4.051 (t, 1H, J=10.0 Hz), 3.543 (m, 1H), 3.036 (dd, 1H, J=15.6, 11.2 Hz), 2.896 (m, 1H, J=15.6, 5.2, 2.0 Hz), 2.672 (m, 2H), 2.297 (s, 3H), 2.199 (s, 3H), 1.798 (t, 2H, J=6.8 Hz), 1.357 (s, 3H), 1.344 (s, 3H).

$^{13}$C-NMR (CDCl$_3$): 152.849, 152.105, 151.536, 136.143, 127.431, 124.846, 124.061, 122.329, 121.519, 112.767, 109.275, 73.652, 69.998, 32.353, 32.311, 30.781, 26.811, 26.404, 20.154, 17.124, 11.743.

Example 10: Synthesis of 3-(2-hydroxy-4,5-dimethylphenyl)-8,8-dimethyl-2,3,4,8,9,10-hexahydropyrano [2,3-f] chromene (Compound 11)

(1) Preparation of methyl 2-(2-benzyloxy-4,5-dimethylphenyl)-3-(2,2-dimethyl-5-hydroxy-2H-1-benzopyran-6-yl) acrylate Methyl 2-(2-benzyloxy-4,5-dimethylphenyl)-3-(2,2-dimethyl-5-hydroxy-2H-1-benzopyran-6-yl) acrylate was obtained in the same manner as in Example 2(1), except that methyl 2-benzyloxy-4,5-dimethylphenyl acetate prepared in Preparation Example 9 was used instead of (methyl 2-benzyloxy-4-methylphenyl) acetate.

$^1$H-NMR (CDCl$_3$): 7.894 (s, 1H), 7.26~7.36 (m, 5H), 6.795 (s, 1H), 6.766 (s, 1H), 6.677 (d, 1H, J=8.4 Hz), 6.591 (d, 1H, J=10.0 Hz), 6.161 (d, 1H, J=8.4 Hz), 5.512 (d, 1H, J=10.0 Hz), 4.994 (s, 2H), 3.680 (s, 3H), 2.223 (s, 3H), 2.072 (s, 3H), 1.375 (s, 6H).

$^{13}$C-NMR (CDCl$_3$): 169.257, 154.688, 154.284, 150.592, 137.994, 137.204, 135.640, 131.947, 130.210, 129.084, 128.604, 128.387, 128.339, 127.573, 126.895, 122.056, 116.624, 115.140, 114.154, 109.504, 108.956, 76.039, 70.161, 52.294, 27.830, 27.781, 20.240, 18.763.

(2) Preparation of 2-(2-benzyloxy-4,5-dimethylphenyl)-3-(2,2-dimethyl-5-hydroxy-2H-1-benzopyran-6-yl) propan-1-ol 2-(2-benzyloxy-4,5-dimethylphenyl)-3-(2,2-dimethyl-5-hydroxy-2H-1-benzopyran-6-yl) propan-1-ol was obtained in the same manner as in Example 2(2), except that methyl 2-(2-benzyloxy-4,5-dimethylphenyl)-3-(2,2-dimethyl-5-hydroxy-2H-1-benzopyran-6-yl) acrylate obtained in (1) was used instead of methyl 2-(2-benzyloxy-4-methylphenyl)-3-(2,2-dimethyl-5-hydroxy-2H-1-benzopyran-6-yl) acrylate.

$^1$H-NMR (CDCl$_3$): 7.30~7.43 (m, 5H), 6.999 (s, 1H), 6.792 (s, 1H), 6.721 (d, 1H, J=10.0 Hz), 6.699 (d, 1H, J=8.0 Hz), 6.293 (d, 1H, J=8.0 Hz), 5.528 (d, 1H, J=10.0 Hz), 5.054 (s, 2H), 3.800 (dd, 1H, J=11.2, 3.6 Hz), 3.691 (dd, 1H, J=11.2, 2.8 Hz), 3.249 (m, 1H), 3.090 (dd, 1H, J=14.0, 10.4 Hz), 2.668 (dd, 1H, J=14.0, 4.0 Hz), 2.232 (s, 3H), 2.188 (s, 3H), 1.406 (s, 3H), 1.385 (s, 3H).

$^{13}$C-NMR (CDCl$_3$): 153.764, 152.283, 150.928, 136.498, 135.796, 130.637, 129.835, 128.952, 128.661, 128.528, 128.448, 128.142, 127.587, 118.246, 117.584, 113.911, 110.276, 108.349, 75.432, 70.689, 63.407, 42.833, 30.722, 27.840, 27.480, 19.817, 18.873.

(3) Preparation of 3-(2-benzyloxy-4,5-dimethylphenyl)-8,8-dimethyl-2,3,4,8-tetrahydropyrano [2,3-f] chromene 3-(2-benzyloxy-4,5-dimethylphenyl)-8,8-dimethyl-2,3,4,8-tetrahydropyrano [2,3-f] chromene was obtained in the same manner as in Example 2(3), except that 2-(2-benzyloxy-4,5-dimethylphenyl)-3-(2,2-dimethyl-5-hydroxy-2H-1-benzopyran-6-yl) propan-1-ol obtained in (2) was used instead of 2-(2-benzyloxy-4-methyl phenyl)-3-(2,2-dimethyl-5-hydroxy-2H-1-benzopyran-6-yl) propan-1-ol.

$^1$H-NMR (CDCl$_3$): 7.32~7.45 (m, 5H), 6.935 (s, 1H), 6.857 (d, 1H, J=8.0 Hz), 6.810 (s, 1H), 6.697 (d, 1H, J=10.0 Hz), 6.407 (d, 1H, J=8.0 Hz), 5.591 (d, 1H, J=10.0 Hz), 5.115 (s, 2H), 4.414 (m, 1H, J=10.0, 3.2, 2.0 Hz), 4.060 (t, 1H, J=10.0 Hz), 3.721 (m, 1H), 3.028 (dd, 1H, J=14.0, 6.8 Hz), 2.877 (dd, 1H, J=14.0, 5.2 Hz), 2.272 (s, 3H), 2.229 (s, 3H), 1.470 (s, 3H), 1.455 (s, 3H).

$^{13}$C-NMR (CDCl$_3$): 154.383, 151.764, 149.792, 137.275, 135.831, 129.162, 128.772, 128.742, 128.544, 128.519, 127.727, 127.064, 126.960, 116.982, 114.536, 113.786, 109.823, 108.514, 75.504, 70.246, 70.192, 31.530, 30.793, 27.746, 27.536, 19.883, 18.973.

(4) Preparation of 3-(2-hydroxy-4,5-dimethylphenyl)-8,8-dimethyl-2,3,4,8,9,10-hexahydropyrano [2,3-f] chromene 3-(2-hydroxy-4,5-dimethylphenyl)-8,8-dimethyl-2,3,4,8,9,10-hexahydropyrano [2,3-f] chromene (Compound 11) was obtained in the same manner as in Example 2(4), except that 3-(2-benzyloxy-4,5-dimethylphenyl)-8,8-dimethyl-2,3,4,8-tetrahydropyrano [2,3-f] chromene obtained in (3) was used instead of 3-(2-benzyloxy-4-methylphenyl)-8,8-dimethyl-2,3,4,8-tetrahydropyrano [2,3-f] chromene.

$^1$H-NMR (CDCl$_3$): 6.886 (s, 1H), 6.857 (d, 1H, J=4.8 Hz), 6.579 (s, 1H), 6.418 (d, 1H, J=4.8 Hz), 4.965 (s, 1H), 4.433 (dd, 1H, J=6.0 Hz), 4.053 (t, 1H, J=6.0 Hz), 3.534 (m, 1H), 3.067 (dd, 1H, J=8.8, 6.8 Hz), 2.873 (ddd, 1H, J=8.8, 2.4, 0.8 Hz), 2.680 (m, 2H), 2.203 (s, 6H), 1.803 (t, 2H, J=4.0 Hz), 1.364 (s, 3H), 1.348 (s, 3H).

$^{13}$C-NMR (CDCl$_3$): 152.711, 152.083, 151.311, 135.979, 128.741, 128.608, 127.462, 124.557, 116.894, 112.952, 109.284, 109.207, 73.761, 69.985, 32.239, 32.018, 30.643, 26.781, 26.368, 19.374, 18.905, 17.122.

Example 11: Synthesis of 3-(2-hydroxy-4-fluorophenyl)-8,8-dimethyl-2,3,4,8,9,10-hexahydropyrano [2,3-f] chromene (Compound 12)

3-(2-hydroxy-4-fluorophenyl)-8,8-dimethyl-2,3,4,8,9,10-hexahydropyrano [2,3-f] chromene (Compound 12) was obtained in the same manner as in Example 2, except that (methyl 2-benzyloxy-4-fluorophenyl) acetate was used instead of (methyl 2-benzyloxy-4-methylphenyl) acetate.

$^1$H-NMR (CDCl$_3$): 7.045 (dd, 1H, J=8.8, 6.6 Hz), 6.834 (d, 1H, J=8.4 Hz), 6.620 (m, 1H, J=8.4, 2.4 Hz), 6.501 (dd, 1H, J=9.6, 2.4 Hz), 6.396 (d, 1H, J=8.4 Hz), 5.400 (s, 1H), 4.379 (m, 1H, J=10.0, 3.2, 2.0 Hz), 4.039 (t, 1H, J=10.0 Hz), 3.523 (m, 1H), 2.997 (dd, 1H, J=15.6, 11.2 Hz), 2.892 (m, 1H, J=15.6, 5.2, 2.0 Hz), 2.642 (m, 2H), 1.777 (t, 2H, J=6.8 Hz), 1.335 (s, 3H), 1.321 (s, 3H).

$^{13}$C-NMR (CDCl$_3$): 163.144, 160.705, 154.402, 152.812, 152.061, 128.471, 127.447, 123.663, 112.574, 109.401, 107.644, 103.157, 73.880, 69.704, 32.297, 31.821, 30.520, 26.784, 26.390, 17.103.

Example 12: Synthesis of 3-(2-hydroxy-4-chlorophenyl)-8,8-dimethyl-2,3,4,8,9,10-hexahydropyrano [2,3-f] chromene (Compound 13)

3-(2-hydroxy-4-chlorophenyl)-8,8-dimethyl-2,3,4,8,9,10-hexahydropyrano [2,3-f] chromene (Compound 13) was obtained in the same manner as in Example 2, except that (methyl 2-benzyloxy-4-chlorophenyl) acetate was used instead of (methyl 2-benzyloxy-4-methylphenyl) acetate.

$^1$H-NMR (CDCl$_3$): 7.026 (d, 1H, J=8.4 Hz), 6.888 (dd, 1H, J=8.4, 2.0 Hz), 6.832 (d, 1H, J=8.4 Hz), 6.759 (d, 1H, J=2.0 Hz), 6.397 (d, 1H, J=8.4 Hz), 5.256 (s, 1H), 4.375 (m, 1H, J=10.0, 3.2, 2.0 Hz), 4.047 (t, 1H, J=10.0 Hz), 3.532 (m, 1H), 2.988 (dd, 1H, J=15.6, 11.2 Hz), 2.848 (m, 1H, J=15.6, 5.2, 2.0 Hz), 2.637 (m, 2H), 1.775 (t, 2H, J=6.8 Hz), 1.333 (s, 3H), 1.320 (s, 3H).

$^{13}$C-NMR (CDCl$_3$): 154.027, 152.821, 152.035, 132.695, 128.594, 127.445, 126.551, 121.205, 115.699, 112.435, 109.442, 109.408, 73.892, 69.487, 32.274, 31.905, 30.318, 26.776, 26.393, 17.093.

Example 13: Synthesis of 3-(2-hydroxy-4-methoxyphenyl)-8,8-dimethyl-2,3,4,8,9,10-hexahydropyrano [2,3-f] chromene (Compound 14)

(1) Preparation of methyl 2-(2-benzyloxy-4-methoxyphenyl)-3-(2,2-dimethyl-5-hydroxy-2H-1-benzopyran-6-yl) acrylate Methyl 2-(2-benzyloxy-4-methoxyphenyl)-3-(2,2-dimethyl-5-hydroxy-2H-1-benzopyran-6-yl) acrylate was obtained in the same manner as in Example 2(1), except that methyl (2-benzyloxy-4-methoxyphenyl) acetate prepared in Preparation Example 10 was used instead of (methyl 2-benzyloxy-4-methylphenyl) acetate.

$^1$H-NMR (CDCl$_3$): 7.875 (s, 1H), 7.24~7.36 (m, 5H), 6.958 (d, 1H, J=8.4 Hz), 6.697 (d, 1H, J=8.4 Hz), 6.598 (d, 1H, J=10.0 Hz), 6.551 (d, 1H, J=2.4 Hz), 6.426 (dd, 1H, J=8.4, 2.4 Hz), 6.195 (d, 1H, J=8.4 Hz), 5.783 (s, H), 5.536 (d, 1H, J=10.0 Hz), 5.030 (s, 2H), 3.777 (s, 3H), 3.700 (s, 3H), 1.395 (s, 6H).

$^{13}$C-NMR (CDCl$_3$): 169.002, 160.933, 157.315, 154.665, 150.202, 136.701, 135.651, 131.736, 130.213, 128.726, 128.489, 128.440, 127.733, 126.958, 117.352, 116.537, 114.996, 109.468, 109.063, 105.279, 100.143, 76.114, 70.097, 55.259, 52.262, 27.855.

(2) Preparation of 2-(2-benzyloxy-4-methoxyphenyl)-3-(2,2-dimethyl-5-hydroxy-2H-1-benzopyran-6-yl) propan-1-ol 2-(2-benzyloxy-4-methoxyphenyl)-3-(2,2-dimethyl-5-hydroxy-2H-1-benzopyran-6-yl) propan-1-ol was obtained in the same manner as in Example 2(2), except that methyl 2-(2-benzyloxy-4-methoxyphenyl)-3-(2,2-dimethyl-5-hydroxy-2H-1-benzopyran-6-yl) acrylate obtained in (1) was used instead of methyl 2-(2-benzyloxy-4-methylphenyl)-3-(2,2-dimethyl-5-hydroxy-2H-1-benzopyran-6-yl) acrylate.

$^1$H-NMR (CDCl$_3$): 7.617 (s, 1H), 7.33~7.42 (m, 5H), 7.150 (d, 1H, J=8.0 Hz), 6.725 (d, 1H, J=10.0 Hz), 6.680 (d, 1H, J=8.4 Hz), 6.582 (d, 1H, J=2.4 hz), 6.488 (dd, 1H, J=8.0, 2.4 Hz), 6.294 (d, 1H, J=8.4 Hz), 5.550 (d, 1H, J=10.0 Hz), 5.075 (s, 2H), 3.820 (m, 1H), 3.787 (s, 3H), 3.719 (m, 1H), 3.292 (m, 1H), 3.085 (dd, 1H, J=14.0, 10.4 Hz), 2.692 (dd, 1H, J=14.0, 4.0 Hz), 2.407 (m, 1H), 1.416 (s, 3H), 1.398 (s, 3H).

$^{13}$C-NMR (CDCl$_3$): 159.512, 156.744, 152.398, 150.989, 136.245, 130.750, 128.848, 128.768, 128.648, 128.291, 127.616, 123.685, 118.015, 117.588, 110.284, 108.446, 104.573 100.232, 75.508, 70.493, 63.479, 55.380, 42.052, 30.536, 27.905, 27.593.

(3) Preparation of 3-(2-benzyloxy-4-methoxyphenyl)-8,8-dimethyl-2,3,4,8-tetrahydropyrano [2,3-f] chromene 3-(2-benzyloxy-4-methoxyphenyl)-8,8-dimethyl-2,3,4,8-tetrahydropyrano [2,3-f] chromene was obtained in the same manner as in Example 2(3), except that 2-(2-benzyloxy-4-methoxyphenyl)-3-(2,2-dimethyl-5-hydroxy-2H-1-benzopyran-6-yl) propan-1-ol obtained in (2) was used instead of 2-(2-benzyloxy-4-methylphenyl)-3-(2,2-dimethyl-5-hydroxy-2H-1-benzopyran-6-yl) propan-1-ol.

$^1$H-NMR (CDCl$_3$): 7.30~7.45 (m, 5H), 7.047 (d, 1H, J=8.0 Hz), 6.821 (d, 1H, J=8.4 Hz), 6.642 (d, 1H, J=10.0 Hz), 6.544 (d, 1H, J=2.0 Hz), 6.476 (dd, 1H, J=8.4, 2.0 Hz), 6.361 (d, 1H, J=8.0 Hz), 5.550 (d, 1H, J=10.0 Hz), 5.295 (s, 1H), 5.087 (s, 2H), 4.369 (m, 1H), 4.023 (t, 1H, J=10.0 Hz), 3.773 (s, 3H), 3.650 (m, 1H), 2.963 (dd, 1H, J=15.6, 10.8 Hz), 2.883 (dd, 1H, J=15.6, 4.4 Hz), 1.425 (s, 3H), 1.410 (s, 3H).

$^{13}$C-NMR (CDCl$_3$): 159.505, 157.258, 151.862 149.841, 136.860, 129.178, 128.834, 128.647, 127.913, 127.725, 127.152, 122.328, 116.978, 114.469, 109.857, 108.582, 104.588, 100.013, 75.558, 70.196, 70.088, 55.347, 31.315, 30.733, 27.795, 27.579.

(4) Preparation of 3-(2-hydroxy-4-methoxyphenyl)-8,8-dimethyl-2,3,4,8,9,10-hexahydropyrano [2,3-f] chromene 3-(2-hydroxy-4-methoxyphenyl)-8,8-dimethyl-2,3,4,8,9,10-hexahydropyrano [2,3-f] chromene (Compound 14) was obtained in the same manner as in Example 2(4), except that 3-(2-benzyloxy-4-methoxyphenyl)-8,8-dimethyl-2,3,4,8- tetrahydropyrano [2,3-f] chromene obtained in (3) was used instead of 3-(2-benzyloxy-4-methylphenyl)-8,8-dimethyl-2,3,4,8-tetrahydropyrano [2,3-f] chromene.

$^1$H-NMR (CDCl$_3$): 7.022 (d, 1H, J=8.4 Hz), 6.837 (d, 1H, J=8.0 Hz), 6.488 (dd, 1H, J=8.0, 2.4 Hz), 6.388 (d, 1H, J=8.4 Hz), 6.364 (d, 1H, J=2.4 Hz), 5.059 (s, 1H), 4.392 (m, 1H, J=10.0, 2.0 Hz), 4.024 (t, 1H, J=10.0 Hz), 3.768 (s, 3H), 3.488 (m, 1H), 3.017 (dd, 1H, J=15.6, 11.2 Hz), 2.875 (m, 1H, J=15.6, 6.8, 2.0 Hz), 2.645 (m, 2H), 1.778 (t, 2H, J=6.8 Hz), 1.335 (s, 3H), 1.321 (s, 3H).

$^{13}$C-NMR (CDCl$_3$): 159.257, 154.516, 152.772, 152.160, 128.184, 127.546, 120.182, 112.994, 109.394, 109.340, 105.957, 102.118, 73.917, 70.069, 55.340, 32.391, 31.811, 30.671, 26.833, 26.459, 17.187.

Example 14: Synthesis of 3-(2-hydroxy-4-ethoxyphenyl)-8,8-dimethyl-2,3,4,8,9,10-hexahydropyrano [2,3-f] chromene (Compound 15)

(1) Preparation of methyl 2-(2-benzyl oxy-4-ethoxyphenyl)-3-(2,2-dimethyl-5-hydroxy-2H-1-benzopyran-6-yl) acrylate Methyl 2-(2-benzyloxy-4-ethoxyphenyl)-3-(2,2-dimethyl-5-hydroxy-2H-1-benzopyran-6-yl) acrylate was obtained in the same manner as in Example 2(1), except that methyl (2-benzyloxy-4-ethoxyphenyl) acetate prepared in Preparation Example 11 was used instead of (methyl 2-benzyloxy-4-methylphenyl) acetate.

$^1$H-NMR (CDCl$_3$): 7.842 (s, 1H), 7.24~7.36 (m, 5H), 6.937 (d, 1H, J=8.4 Hz), 6.699 (d, 1H, J=8.4 Hz), 6.578 (d, 1H, J=10.0 Hz), 6.548 (s, 1H), 6.411 (d, 1H, J=8.4 Hz), 6.193 (d, 1H, J=8.4 Hz), 5.719 (s, H), 5.532 (d, 1H, J=10.0 Hz), 5.016 (s, 2H), 3.994 (q, 2H, J=6.8 Hz), 3.693 (s, 3H), 1.389 (s, 6H), 1.389 (t, 3H).

$^{13}$C-NMR (CDCl$_3$): 168.924, 160.391, 157.312, 154.649, 150.070, 136.734, 135.557, 131.731, 130.243, 128.734, 128.692, 128.438, 127.728, 126.969, 117.117, 116.553, 114.983, 109.481, 109.084, 105.879, 100.527, 76.126, 70.096, 63.462, 52.237, 27.863, 14.767.

(2) Preparation of 2-(2-benzyloxy-4-ethoxyphenyl)-3-(2,2-dimethyl-5-hydroxy-2H-1-benzopyran-6-yl) propan-1-ol 2-(2-benzyloxy-4-ethoxyphenyl)-3-(2, 2-di methyl-5-hydroxy-2H-1-benzopyran-6-yl) propan-1-ol was obtained in the same manner as in Example 2(2), except that methyl 2-(2-benzyloxy-4-ethoxyphenyl)-3-(2,2-dimethyl-5-hydroxy-2H-1-benzopyran-6-yl) acrylate obtained in (1) was used instead of methyl 2-(2-benzyloxy-4-methyl phenyl)-3-(2,2-dimethyl-5-hydroxy-2H-1-benzopyran-6-yl) acrylate.

$^1$H-NMR (CDCl$_3$): 7.676 (s, 1H), 7.33~7.42 (m, 5H), 7.139 (d, 1H, J=8.0 Hz), 6.734 (d, 1H, J=10.0 Hz), 6.692 (d, 1H, J=8.4 Hz), 6.594 (d, 1H, J=2.4 hz), 6.484 (dd, 1H, J=8.0, 2.4 Hz), 6.303 (d, 1H, J=8.4 Hz), 5.559 (d, 1H, J=10.0 Hz), 5.077 (s, 2H), 4.019 (q, 2H, J=7.2 Hz), 3.826 (m, 1H), 3.729 (m, 1H), 3.291 (m, 1H), 3.096 (dd, 1H, J=14.0, 10.4 Hz), 2.696 (dd, 1H, J=14.0, 4.0 Hz), 2.457 (b, 1H), 1.425 (s, 3H), 1.416 (t, 3H), 1.406 (s, 3H).

$^{13}$C-NMR (CDCl$_3$): 158.871, 156.742, 152.390, 150.988, 136.262, 130.727, 128.823, 128.744, 128.609, 128.261, 127.598, 123.504, 118.006, 117.584, 110.268, 108.422, 105.250, 100.663, 75.481, 70.479, 63.550, 63.495, 42.148, 30.525, 27.897, 27.584, 14.812.

(3) Preparation of 3-(2-benzyloxy-4-ethoxyphenyl)-8,8-dimethyl-2,3,4,8-tetrahydropyrano [2,3-f] chromene 3-(2-benzyloxy-4-ethoxyphenyl)-8,8-di methyl-2,3,4,8-tetrahydropyrano [2,3-f] chromene was obtained in the same manner as in Example 2(3), except that 2-(2-benzyloxy-4-ethoxyphenyl)-3-(2, 2-di methyl-5-hydroxy-2H-1-benzopyran-6-yl) propan-1-ol obtained in (2) was used instead of 2-(2-benzyloxy-4-methylphenyl)-3-(2,2-dimethyl-5-hydroxy-2H-1-benzopyran-6-yl) propan-1-ol.

$^1$H-NMR (CDCl$_3$): 7.30~7.45 (m, 5H), 7.047 (d, 1H, J=8.0 Hz), 6.841 (d, 1H, J=8.4 Hz), 6.665 (d, 1H, J=10.0 Hz), 6.566 (d, 1H, J=2.0 Hz), 6.482 (dd, 1H, J=8.4, 2.0 Hz), 6.385 (d, 1H, J=8.0 Hz), 5.571 (d, 1H, J=10.0 Hz), 5.096 (s, 2H), 4.384 (m, 1H), 4.026 (q, 2H, J=6.8 Hz), 4.009 (t, 1H, J=10.0 Hz), 3.661 (m, 1H), 2.980 (dd, 1H, J=15.6, 10.8 Hz), 2.878 (dd, 1H, J=15.6, 4.4 Hz), 1.446 (s, 3H), 1.430 (s, 3H), 1.411 (t, 3H, J=6.8 Hz).

$^{13}$C-NMR (CDCl$_3$): 158.825, 157.218, 151.784, 149.811, 136.871, 129.153, 128.783, 128.598, 127.850, 127.652, 127.097, 122.093, 116.957, 114.469, 109.814, 108.531, 105.203, 100.385, 75.515, 70.183, 70.013, 63.462, 31.277, 30.706, 27.767, 27.549, 14.809.

(4) Preparation of 3-(2-hydroxy-4-ethoxyphenyl)-8,8-dimethyl-2,3,4,8,9,10-hexahydropyrano [2,3-f] chromene 3-(2-hydroxy-4-ethoxyphenyl)-8,8-dimethyl-2,3,4,8,9,10-hexahydropyrano [2,3-f] chromene (Compound 15) was obtained in the same manner as in Example 2(4), except that 3-(2-benzyloxy-4-ethoxyphenyl)-8,8-dimethyl-2,3,4,8-tetrahydropyrano [2,3-f] chromene obtained in (3) was used instead of 3-(2-benzyloxy-4-methylphenyl)-8,8-dimethyl-2,3,4,8-tetrahydropyrano [2,3-f] chromene.

$^1$H-NMR (CDCl$_3$): 6.989 (d, 1H, J=8.4 Hz), 6.825 (d, 1H, J=8.0 Hz), 6.458 (dd, 1H, J=8.0, 2.4 Hz), 6.387 (d, 1H, J=8.4 Hz), 6.324 (d, 1H, J=2.4 Hz), 5.355 (s, 1H), 4.386 (m, 1H, J=10.4, 3.2, 2.0 Hz), 4.007 (t, 1H, J=10.4 Hz), 3.954 (q, 2H, J=7.2 Hz), 3.484 (m, 1H), 3.006 (dd, 1H, J=15.6, 11.2 Hz), 2.852 (m, 1H, J=15.6, 4.8, 1.6 Hz), 2.641 (m, 2H), 1.770 (t, 2H, J=6.8 Hz), 1.378 (t, 2H, J=6.8 Hz), 1.331 (s, 3H), 1.316 (s, 3H).

$^{13}$C-NMR (CDCl$_3$): 158.552, 154.340, 152.719, 152.091, 128.075, 127.465, 119.882, 112.909, 109.305, 109.248, 106.572, 102.504, 73.798, 70.018, 63.450, 32.311, 31.749, 30.614, 26.776, 26.390, 17.116, 14.781.

Example 15: Synthesis of 3-(2-hydroxy-4-propoxyphenyl)-8,8-dimethyl-2,3,4,8,9,10-hexahydropyrano [2,3-f] chromene (Compound 16)

(1) Preparation of methyl 2-(2-benzyloxy-4-propoxyphenyl)-3-(2,2-dimethyl-5-hydroxy-2H-1-benzopyran-6-yl) acrylate Methyl 2-(2-benzyloxy-4-propoxyphenyl)-3-(2,2-dimethyl-5-hydroxy-2H-1-benzopyran-6-yl) acrylate was obtained in the same manner as in Example 2(1), except that methyl (2-benzyloxy-4-propoxyphenyl) acetate prepared in Preparation Example 12 was used instead of (methyl 2-benzyloxy-4-methylphenyl) acetate.

$^1$H-NMR (CDCl$_3$): 7.816 (s, 1H), 7.24~7.36 (m, 5H), 6.928 (d, 1H, J=8.4 Hz), 6.705 (d, 1H, J=8.4 Hz), 6.562 (d, 1H, J=10.0 Hz), 6.552 (d, 1H, J=2.0 Hz), 6.408 (dd, 1H, J=8.4, 2.0 Hz), 6.195 (d, 1H, J=8.4 Hz), 5.599 (b, H), 5.526

(d, 1H, J=10.0 Hz), 5.012 (s, 2H), 3.880 (t, 2H, J=6.4 Hz), 3.687 (s, 3H), 1.785 (m, 2H), 1.385 (s, 6H), 1.024 (t, 3H, J=7.2 Hz).

$^{13}$C-NMR (CDCl$_3$): 169.032, 160.423, 157.356, 154.638, 150.111, 136.730, 135.529, 131.711, 130.229, 128.714, 128.632, 128.426, 127.724, 126.989, 117.177, 116.564, 114.994, 109.488, 109.066, 105.932, 100.492, 76.117, 70.086, 69.489, 52.236, 27.857, 22.534, 10.495.

(2) Preparation of 2-(2-benzyloxy-4-propoxyphenyl)-3-(2,2-dimethyl-5-hydroxy-2H-1-benzopyran-6-yl) propan-1-ol 2-(2-benzyloxy-4-propoxyphenyl)-3-(2,2-dimethyl-5-hydroxy-2H-1-benzopyran-6-yl) propan-1-ol was obtained in the same manner as in Example 2(2), except that methyl 2-(2-benzyloxy-4-propoxyphenyl)-3-(2,2-dimethyl-5-hydroxy-2H-1-benzopyran-6-yl) acrylate obtained in (1) was used instead of methyl 2-(2-benzyloxy-4-methyl phenyl)-3-(2,2-dimethyl-5-hydroxy-2H-1-benzopyran-6-yl) acrylate.

$^1$H-NMR (CDCl$_3$): 7.401 (b, 1H), 7.33~7.42 (m, 5H), 7.128 (d, 1H, J=8.0 Hz), 6.722 (d, 1H, J=10.0 Hz), 6.682 (d, 1H, J=8.4 Hz), 6.595 (d, 1H, J=2.4 hz), 6.480 (dd, 1H, J=8.0, 2.4 Hz), 6.291 (d, 1H, J=8.4 Hz), 5.548 (d, 1H, J=10.0 Hz), 5.070 (s, 2H), 3.899 (t, 2H, J=6.8 Hz), 3.816 (m, 1H), 3.706 (m, 1H), 3.282 (m, 1H), 3.085 (dd, 1H, J=14.0, 10.4 Hz), 2.687 (dd, 1H, J=14.0, 4.0 Hz), 2.432 (b, 1H), 1.798 (2H, m), 1.415 (s, 3H), 1.396 (s, 3H), 1.035 (t, 3H).

$^{13}$C-NMR (CDCl$_3$): 159.071, 156.734, 152.376, 150.986, 136.252, 130.727, 128.818, 128.740, 128.600, 128.264, 127.621, 123.437, 118.025, 117.586, 110.267, 108.415, 105.290, 100.625, 75.480, 70.480, 69.615, 63.494, 42.178, 30.515, 27.895, 27.571, 22.555, 10.529.

(3) Preparation of 3-(2-benzyloxy-4-propoxyphenyl)-8,8-dimethyl-2,3,4,8-tetrahydropyrano [2,3-f] chromene 3-(2-benzyloxy-4-propoxyphenyl)-8,8-dimethyl-2,3,4,8-tetrahydropyrano [2,3-f] chromene was obtained in the same manner as in Example 2(3), except that 2-(2-benzyloxy-4-propoxyphenyl)-3-(2,2-dimethyl-5-hydroxy-2H-1-benzopyran-6-yl) propan-1-ol obtained in (2) was used instead of 2-(2-benzyloxy-4-methylphenyl)-3-(2,2-dimethyl-5-hydroxy-2H-1-benzopyran-6-yl) propan-1-ol.

$^1$H-NMR (CDCl$_3$): 7.30~7.45 (m, 5H), 7.045 (d, 1H, J=8.0 Hz), 6.834 (d, 1H, J=8.4 Hz), 6.664 (d, 1H, J=10.0 Hz), 6.575 (d, 1H, J=2.0 Hz), 6.498 (dd, 1H, J=8.4, 2.0 Hz), 6.380 (d, 1H, J=8.0 Hz), 5.562 (d, 1H, J=10.0 Hz), 5.097 (s, 2H), 4.376 (m, 1H), 4.0346 (t, 1H, J=10.0 Hz), 3.899 (t, 2H, J=6.4 Hz), 3.663 (m, 1H), 2.982 (dd, 1H, J=15.6, 10.8 Hz), 2.874 (dd, 1H, J=15.6, 4.4 Hz), 1.785 (m, 2H), 1.444 (s, 3H), 1.429 (s, 3H), 1.041 (t, 3H, J=7.2 Hz).

$^{13}$C-NMR (CDCl$_3$): 159.044, 157.236, 151.790, 149.823, 136.889, 128.784, 128.598, 127.855, 127.647, 127.124, 122.042, 116.967, 114.482, 109.821, 108.532, 105.286, 100.380, 75.523, 70.199, 70.036, 69.553, 31.287, 30.720, 27.773, 27.560, 22.549, 10.525.

(4) Preparation of 3-(2-hydroxy-4-propoxyphenyl)-8,8-dimethyl-2,3,4,8,9,10-hexahydropyrano [2,3-f] chromene 3-(2-hydroxy-4-propoxyphenyl)-8,8-dimethyl-2,3,4,8,9,10-hexahydropyrano [2,3-f] chromene (Compound 16) was obtained in the same manner as in Example 2(4), except that 3-(2-benzyloxy-4-propoxyphenyl)-8,8-dimethyl-2,3,4,8-tetrahydropyrano [2,3-f] chromene obtained in (3) was used instead of 3-(2-benzyloxy-4-methylphenyl)-8,8-dimethyl-2,3,4,8-tetrahydropyrano [2,3-f] chromene.

$^1$H-NMR (CDCl$_3$): 6.976 (d, 1H, J=8.4 Hz), 6.817 (d, 1H, J=8.0 Hz), 6.452 (dd, 1H, J=8.0, 2.0 Hz), 6.392 (d, 1H, J=8.4 Hz), 6.316 (d, 1H, J=2.0 Hz), 5.600 (s, 1H), 4.380 (d, 1H, J=10.0 Hz), 4.000 (t, 1H, J=10.0 Hz), 3.812 (t, 2H, J=6.4 Hz), 3.488 (m, 1H), 2.997 (dd, 1H, J=15.6, 11.2 Hz), 2.837 (dd, 1H, J=15.6, 4.4 Hz), 2.640 (m, 2H), 1.782 (t, 2H, J=6.8 Hz), 1.765 (m, 2H), 1.329 (s, 3H), 1.314 (s, 3H), 0.994 (t, 3H, J=7.2 Hz).

$^{13}$C-NMR (CDCl$_3$): 158.678, 154.412, 152.596, 152.054, 128.015, 127.483, 119.827, 113.016, 109.299, 109.226, 106.588, 102.460, 73.888, 70.014, 69.537, 32.287, 31.702, 30.552, 26.728, 26.349, 22.453, 17.096, 10.458.

Example 16: Synthesis of 3-(2-hydroxy-4-isopropoxyphenyl)-8,8-dimethyl-2,3,4,8,9,10-hexahydropyrano [2,3-f] chromene (Compound 17)

3-(2-hydroxy-4-isopropoxyphenyl)-8,8-dimethyl-2,3,4,8,9,10-hexahydropyrano [2,3-f] chromene (Compound 17) was obtained in the same manner as in Example 2, except that (methyl 2-benzyloxy-4-isopropoxyphenyl) acetate was used instead of (methyl 2-benzyloxy-4-methylphenyl) acetate.

$^1$H-NMR (CDCl$_3$): 7.000 (d, 1H, J=8.4 Hz), 6.845 (d, 1H, J=8.0 Hz), 6.472 (dd, 1H, J=8.0, 2.4 Hz), 6.404 (d, 1H, J=8.4 Hz), 6.344 (d, 1H, J=2.4 Hz), 5.333 (s, 1H), 4.450 (m, 1H, J=6.0 Hz), 4.409 (m, 1H, J=10.4, 3.2, 2.0 Hz), 4.026 (t, 1H, J=10.4 Hz), 3.498 (m, 1H), 3.026 (dd, 1H, J=15.2, 11.2 Hz), 2.871 (m, 1H, J=15.2, 4.8, 1.6 Hz), 2.669 (m, 2H), 1.789 (t, 2H, J=6.8 Hz), 1.378 (t, 2H, J=6.8 Hz), 1.349 (s, 3H), 1.331 (s, 3H), 1.324 (d, 6H, J=6.0 Hz).

$^{13}$C-NMR (CDCl$_3$): 157.519, 154.443, 152.755, 152.116, 128.071, 127.463, 119.886, 112.931, 109.311, 109.266, 107.931, 103.837, 73.778, 70.102, 70.044, 32.349, 31.818, 30.655, 26.787, 26.401, 22.044, 17.128.

Example 17: Synthesis of 3-(2-hydroxy-4-butoxyphenyl)-8,8-dimethyl-2,3,4,8,9,10-hexahydropyrano [2,3-f] chromene (Compound 18)

(1) Preparation of methyl 2-(2-benzyl oxy-4-butoxyphenyl)-3-(2,2-dimethyl-5-hydroxy-2H-1-benzopyran-6-yl) acrylate Methyl 2-(2-benzyloxy-4-butoxyphenyl)-3-(2,2-dimethyl-5-hydroxy-2H-1-benzopyran-6-yl) acrylate was obtained in the same manner as in Example 2(1), except that methyl (2-benzyloxy-4-butoxyphenyl) acetate prepared in Preparation Example 13 was used instead of (methyl 2-benzyloxy-4-methylphenyl) acetate.

$^1$H-NMR (CDCl$_3$): 7.836 (s, 1H), 7.24~7.36 (m, 5H), 6.928 (d, 1H, J=8.4 Hz), 6.698 (d, 1H, J=8.4 Hz), 6.577 (d, 1H, J=10.0 Hz), 6.546 (d, 1H, J=2.0 Hz), 6.407 (dd, 1H, J=8.4, 2.0 Hz), 6.188 (d, 1H, J=8.4 Hz), 5.726 (b, H), 5.523 (d, 1H, J=10.0 Hz), 5.010 (s, 2H), 3.918 (t, 2H, J=6.4 Hz), 3.683 (s, 3H), 1.752 (m, 2H), 1.468 (m, 2H), 1.383 (s, 6H), 0.986 (t, 3H, J=7.2 Hz).

$^{13}$C-NMR (CDCl$_3$): 169.062, 160.539, 157.338, 154.664, 150.278, 136.737, 135.556, 131.694, 130.196, 128.667, 128.450, 128.405, 127.968, 126.968, 117.138, 116.575, 115.049, 109.499, 109.022, 105.911, 100.487, 76.090, 70.061, 67.676, 52.223, 31.263, 28.050, 19.191, 13.802.

(2) Preparation of 2-(2-benzyloxy-4-butoxyphenyl)-3-(2,2-dimethyl-5-hydroxy-2H-1-benzopyran-6-yl) propan-1-ol 2-(2-benzyloxy-4-butoxyphenyl)-3-(2, 2-di methyl-5-hydroxy-2H-1-benzopyran-6-yl) propan-1-ol was obtained in the same manner as in Example 2(2), except that methyl 2-(2-benzyloxy-4-butoxyphenyl)-3-(2,2-dimethyl-5-hydroxy-2H-1-benzopyran-6-yl) acrylate obtained in (1) was used instead of methyl 2-(2-benzyloxy-4-methyl phenyl)-3-(2,2-dimethyl-5-hydroxy-2H-1-benzopyran-6-yl) acrylate.

$^1$H-NMR (CDCl$_3$): 7.401 (b, 1H), 7.33~7.42 (m, 5H), 7.128 (d, 1H, J=8.0 Hz), 6.723 (d, 1H, J=10.0 Hz), 6.682 (d, 1H, J=8.4 Hz), 6.588 (d, 1H, J=2.4 hz), 6.479 (dd, 1H, J=8.0, 2.4 Hz), 6.291 (d, 1H, J=8.4 Hz), 5.547 (d, 1H, J=10.0 Hz), 5.068 (s, 2H), 3.940 (t, 2H, J=6.8 Hz), 3.814 (m, 1H), 3.704 (m, 1H), 3.280 (m, 1H), 3.084 (dd, 1H, J=14.0, 10.4 Hz), 2.681 (dd, 1H, J=14.0, 4.0 Hz), 2.43 (b, 1H), 1.767 (2H, m), 1.489 (m, 2H), 1.415 (s, 3H), 1.396 (s, 3H), 0.977 (t, 3H).

$^{13}$C-NMR (CDCl$_3$): 159.068, 156.721, 152.360, 150.973, 136.220, 130.726, 128.799, 128.729, 128.596, 128.249, 127.611, 123.425, 118.039, 117.579, 110.259, 108.407, 105.271, 100.606, 75.473, 70.464, 67.782, 63.477, 42.119, 31.286, 30.521, 27.884, 27.566, 19.228, 13.838.

(3) Preparation of 3-(2-benzyloxy-4-butoxyphenyl)-8,8-dimethyl-2,3,4,8-tetrahydropyrano [2,3-f] chromene 3-(2-benzyloxy-4-butoxyphenyl)-8,8-dimethyl-2,3,4,8-tetrahydropyrano [2,3-f] chromene was obtained in the same manner as in Example 2(3), except that 2-(2-benzyloxy-4-butoxyphenyl)-3-(2, 2-di methyl-5-hydroxy-2H-1-benzopyran-6-yl) propan-1-ol obtained in (2) was used instead of 2-(2-benzyloxy-4-methylphenyl)-3-(2,2-dimethyl-5-hydroxy-2H-1-benzopyran-6-yl) propan-1-ol.

$^1$H-NMR (CDCl$_3$): 7.30~7.45 (m, 5H), 7.022 (d, 1H, J=8.0 Hz), 6.813 (d, 1H, J=8.4 Hz), 6.640 (d, 1H, J=10.0 Hz), 6.548 (d, 1H, J=2.0 Hz), 6.465 (dd, 1H, J=8.4, 2.0 Hz), 6.357 (d, 1H, J=8.0 Hz), 5.544 (d, 1H, J=10.0 Hz), 5.075 (s, 2H), 4.359 (m, 1H), 4.012 (t, 1H, J=10.0 Hz), 3.919 (t, 2H, J=6.4 Hz), 3.641 (m, 1H), 2.956 (dd, 1H, J=15.6, 10.8 Hz), 2.856 (dd, 1H, J=15.6, 4.4 Hz), 1.739 (m, 2H), 1.473 (m, 2H), 1.422 (s, 3H), 1.407 (s, 3H), 0.964 (t, 3H, J=7.2 Hz).

$^{13}$C-NMR (CDCl$_3$): 159.063, 157.233, 151.793, 149.826, 136.896, 128.782, 128.600, 127.856, 127.644, 127.126, 122.031, 116.970, 114.483, 109.823, 108.534, 105.279, 100.378, 75.521, 70.201, 70.038, 67.725, 31.291, 30.723, 27.774, 27.561, 19.231, 13.833.

(4) Preparation of 3-(2-hydroxy-4-butoxyphenyl)-8,8-dimethyl-2,3,4,8,9,10-hexahydropyrano [2,3-f] chromene 3-(2-hydroxy-4-butoxyphenyl)-8,8-dimethyl-2,3,4,8,9,10-hexahydropyrano [2,3-f] chromene (Compound 18) was obtained in the same manner as in Example 2(4), except that 3-(2-benzyloxy-4-butoxyphenyl)-8,8-dimethyl-2,3,4,8-tetrahydropyrano [2,3-f] chromene obtained in (3) was used instead of 3-(2-benzyloxy-4-methylphenyl)-8,8-dimethyl-2,3,4,8-tetrahydropyrano [2,3-f] chromene.

$^1$H-NMR (CDCl$_3$): 7.009 (d, 1H, J=8.4 Hz), 6.847 (d, 1H, J=8.0 Hz), 6.482 (dd, 1H, J=8.0, 2.0 Hz), 6.408 (d, 1H, J=8.4 Hz), 6.355 (d, 1H, J=2.0 Hz), 5.313 (s, 1H), 4.407 (m, 1H, J=10.0 Hz), 4.027 (t, 1H, J=10.0 Hz), 3.906 (t, 2H, J=6.4 Hz), 3.503 (m, 1H), 3.027 (dd, 1H, J=15.2 Hz), 2.874 (dd, 1H, J=15.6, 4.4 Hz), 2.662 (m, 2H), 1.70~1.90 (m, 4H), 1.482 (m, 2H), 1.351 (s, 3H), 1.337 (s, 3H), 0.977 (t, 3H, J=7.2 Hz).

$^{13}$C-NMR (CDCl$_3$): 158.793, 154.331, 152.721, 152.092, 128.047, 127.461, 119.777, 112.909, 109.299, 109.248, 106.628, 102.511, 73.786, 70.023, 67.738, 32.317, 31.756, 31.227, 30.626, 26.777, 26.390, 19.193, 17.117, 13.807.

Example 18: Synthesis of 3-(2-hydroxy-4-n-pentoxyphenyl)-8,8-dimethyl-2,3,4,8,9,10-hexahydropyrano [2,3-f] chromene (Compound 19)

3-(2-hydroxy-4-n-pentoxyphenyl)-8,8-dimethyl-2,3,4,8,9,10-hexahydropyrano [2,3-f] chromene (Compound 19) was obtained in the same manner as in Example 2, except that (methyl 2-benzyloxy-4-n-pentoxyphenyl) acetate was used instead of (methyl 2-benzyloxy-4-methylphenyl) acetate.

$^1$H-NMR (CDCl$_3$): 7.008 (d, 1H, J=8.0 Hz), 6.847 (d, 1H, J=8.0 Hz), 6.482 (dd, 1H, J=8.0, 2.4 Hz), 6.409 (d, 1H, J=8.0 Hz), 6.355 (d, 1H, J=2.4 Hz), 5.324 (s, 1H), 4.408 (m, 1H, J=10.4 Hz), 4.029 (t, 1H, J=10.4 Hz), 3.897 (t, 2H, J=6.4 Hz), 3.494 (m, 1H), 3.028 (dd, 1H, J=15.6, 11.2 Hz), 2.875 (m, 1H, J=15.6, 4.4 Hz), 2.663 (m, 2H), 1.71~1.88 (m, 4H), 1.35~1.50 (m, 4H), 1.353 (s, 3H), 1.338 (s, 3H), 0.941 (t, 3H, J=7.2 Hz).

$^{13}$C-NMR (CDCl$_3$): 158.726, 154.374, 152.646, 152.062, 128.017, 127.468, 119.767, 112.957, 109.290, 109.222, 106.546, 102.460, 73.833, 70.016, 68.022, 32.287, 31.706, 30.571, 28.862, 28.121, 26.750, 26.362, 22.403, 17.102, 13.997.

Example 19: Synthesis of 3-(2-hydroxy-4-(3-methylbutoxy)phenyl)-8,8-dimethyl-2,3,4,8,9,10-hexahydropyrano [2,3-f] chromene (Compound 20)

3-(2-hydroxy-4-(3-methylbutoxyl)phenyl)-8,8-dimethyl-2,3,4,8,9,10-hexahydropyrano [2,3-f] chromene (Compound 20) was obtained in the same manner as in Example 2, except that (methyl 2-benzyloxy-4-(3-methylbutoxy)phenyl) acetate was used instead of (methyl 2-benzyloxy-4-methylphenyl) acetate.

$^1$H-NMR (CDCl$_3$): 7.001 (d, 1H, J=8.4 Hz), 6.833 (d, 1H, J=8.4 Hz), 6.477 (dd, 1H, J=8.4, 2.4 Hz), 6.381 (d, 1H, J=8.4 Hz), 6.352 (d, 1H, J=2.4 Hz), 4.852 (s, 1H), 4.387 (m, 1H, J=10.4, 2.0, 1.2 Hz), 4.015 (t, 1H, J=10.4 Hz), 3.939 (t, 2H, J=6.4 Hz), 3.470 (m, 1H), 3.014 (dd, 1H, J=15.6, 11.2 Hz), 2.866 (m, 1H, J=15.6, 3.6, 1.6 Hz), 2.659 (m, 2H), 1.802 (m, 1H), 1.774 (t, 2H, J=6.4 Hz), 1.654 (q, 2H, J=6.4 Hz), 1.331 (s, 3H), 1.317 (s, 3H), 0.951 (d, 6H, J=6.4 Hz).

$^{13}$C-NMR (CDCl$_3$): 158.881, 154.197, 152.861, 152.137, 128.120, 127.459, 119.736, 112.789, 109.298, 109.284, 106.724, 102.561, 73.700, 70.031, 66.431, 37.940, 32.345, 31.805, 30.710, 26.839, 26.434, 25.031, 22.573, 17.150.

Example 20: Synthesis of 3-(2-hydroxy-4-(methoxymethoxy)phenyl)-8,8-dimethyl-2,3,4,8,9,10-hexahydropyrano [2,3-f] chromene (Compound 21)

3-(2-hydroxy-4-(methoxymethoxy)phenyl)-8,8-dimethyl-2,3,4,8,9,10-hexahydropyrano [2,3-f] chromene (Compound 21) was obtained in the same manner as in Example 2, except that (methyl 2-benzyloxy-4-(methoxymethoxy)phenyl) acetate was used instead of (methyl 2-benzyloxy-4-methylphenyl) acetate.

¹H-NMR (CDCl₃): 7.023 (d, 1H, J=8.4 Hz), 6.839 (d, 1H, J=8.4 Hz), 6.615 (dd, 1H, J=8.4, 2.4 Hz), 6.524 (d, 1H, J=2.4 Hz), 6.396 (d, 1H, J=8.4 Hz), 5.443 (s, 1H), 5.142 (s, 2H), 4.400 (m, 1H, J=10.4, 3.2, 2.4 Hz), 4.028 (t, 1H, J=10.4 Hz), 3.514 (m, 1H), 3.487 (s, 3H), 3.020 (dd, 1H, J=15.6, 11.2 Hz), 2.892 (m, 1H, J=15.6, 5.2, 1.6 Hz), 2.653 (m, 2H), 1.783 (t, 2H, J=6.8 Hz), 1.342 (s, 3H), 1.327 (s, 3H).

¹³C-NMR (CDCl₃): 156.730, 154.424, 152.790, 152.106, 128.178, 127.448, 121.402, 112.808, 109.314, 109.295, 108.608, 103.952, 94.398, 73.752, 69.932, 55.957, 32.337, 31.833, 30.573, 26.783, 26.405, 17.123.

Example 21: Synthesis of 3-(2-hydroxy-4-(2-methoxyethoxy)phenyl)-8,8-dimethyl-2,3,4,8,9,10-hexahydropyrano [2,3-f] chromene (Compound 22)

3-(2-hydroxy-4-(2-methoxyethoxy)phenyl)-8,8-dimethyl-2,3,4,8,9,10-hexahydropyrano [2,3-f] chromene (Compound 22) was obtained in the same manner as in Example 2, except that (methyl 2-benzyloxy-4-(2-methoxyethoxy)phenyl) acetate was used instead of (methyl 2-benzyloxy-4-methylphenyl) acetate.

¹H-NMR (CDCl₃): 6.976 (d, 1H, J=8.4 Hz), 6.833 (d, 1H, J=8.4 Hz), 6.489 (d, 1H, J=2.4 Hz), 6.433 (dd, 1H, J=8.4, 2.4 Hz), 6.386 (d, 1H, J=8.4 Hz), 6.170 (s, 1H), 4.388 (m, 1H, J=10.4, 2.4 Hz), 4.083 (t, 2H, J=4.4 Hz), 3.997 (t, 1H, J=10.4 Hz), 3.784 (t, 2H, J=4.4 Hz), 3.500 (m, 1H), 3.475 (s, 3H), 3.006 (dd, 1H, J=15.6, 11.2 Hz), 2.853 (m, 1H, J=15.6, 3.6 Hz), 2.650 (t, 2H), 1.777 (t, 2H, J=6.8 Hz), 1.336 (s, 3H), 1.322 (s, 3H).

¹³C-NMR (CDCl₃): 158.296, 154.797, 152.783, 152.137, 127.862, 127.448, 120.507, 112.917, 109.274, 109.231, 105.465, 103.206, 73.683, 71.131, 66.834, 59.012, 32.346, 31.791, 30.559, 26.802, 26.410, 17.130.

Example 22: Synthesis of 3-(2-hydroxy-4-methoxyphenyl)-8,8-diethyl-2,3,4,8,9,10-hexahydropyrano [2,3-f] chromene (Compound 23)

(1) Preparation of methyl 2-(2-benzyloxy-4-methoxylphenyl)-3-(2,2-diethyl-5-hydroxy-2H-1-benzopyran-6-yl) acrylate Methyl 2-(2-benzyloxy-4-methoxyphenyl)-3-(2,2-diethyl-5-hydroxy-2H-1-benzopyran-6-yl) acrylate was obtained in the same manner as in Example 2, except that methyl (2-benzyloxy-4-methoxylphenyl) acetate prepared in Preparation Example 10 was used instead of (methyl 2-benzyloxy-4-methylphenyl) acetate, and 6-formyl-2,2-diethyl-2H-chromen-5-yl benzoate prepared in Preparation Example 14 was used instead of 6-formyl-2,2-dimethyl-2H-chromen-5-yl benzoate.

¹H-NMR (CDCl₃): 7.857 (s, 1H), 7.24~7.36 (m, 5H), 6.973 (d, 1H, J=8.4 Hz), 6.677 (d, 1H, J=10.0 Hz), 6.675 (d, 1H, J=8.4 Hz), 6.550 (d, 1H, J=2.4 Hz), 6.441 (dd, 1H, J=8.4, 2.4 Hz), 6.172 (d, 1H, J=8.4 Hz), 5.620 (s, H), 5.412 (d, 1H, J=10.0 Hz), 5.022 (s, 2H), 3.783 (s, 3H), 3.700 (s, 3H), 1.699 (m, 2H), 1.602 (m, 2H), 0.901 (t, 6H).

¹³C-NMR (CDCl₃): 168.950, 160.945, 157.335, 155.775, 150.135, 136.737, 135.601, 131.781, 130.240, 128.438, 128.128, 127.719, 126.973, 126.210, 117.719, 117.451, 114.573, 109.176, 108.622, 105.334, 100.176, 81.856, 70.123, 55.273, 52.218, 32.165, 7.907.

(2) Preparation of 2-(2-benzyloxy-4-methoxyphenyl)-3-(2,2-diethyl-5-hydroxy-2H-1-benzopyran-6-yl) propan-1-ol 2-(2-benzyloxy-4-methoxyphenyl)-3-(2,2-diethyl-5-hydroxy-2H-1-benzopyran-6-yl) propan-1-ol was obtained in the same manner as in Example 13(2), except that methyl 2-(2-benzyloxy-4-methoxyphenyl)-3-(2,2-diethyl-5-hydroxy-2H-1-benzopyran-6-yl) acrylate obtained in (1) was used instead of methyl 2-(2-benzyloxy-4-methoxyphenyl)-3-(2,2-dimethyl-5-hydroxy-2H-1-benzopyran-6-yl) acrylate.

¹H-NMR (CDCl₃): 7.547 (s, 1H), 7.33~7.42 (m, 5H), 7.181 (d, 1H, J=8.0 Hz), 6.829 (d, 1H, J=10.0 Hz), 6.680 (d, 1H, J=8.0 Hz), 6.599 (d, 1H, J=2.4 hz), 6.508 (dd, 1H, J=8.0, 2.4 Hz), 6.295 (d, 1H, J=8.0 Hz), 5.452 (d, 1H, J=10.0 Hz), 5.086 (s, 2H), 3.817 (m, 1H), 3.800 (s, 3H), 3.741 (m, 1H), 3.311 (m, 1H), 3.083 (dd, 1H, J=14.0, 10.4 Hz), 2.696 (dd, 1H, J=14.0, 4.0 Hz), 2.427 (b, 1H), 1.721 (m, 2H), 1.666 (m, 2H), 0.953 (t, 3H), 0.938 (t, 3H).

¹³C-NMR (CDCl₃): 159.490, 156.750, 153.281, 150.879, 136.250, 130.632, 128.794, 128.736, 128.381, 128.248, 127.598, 123.780, 118.861, 117.559, 109.991, 107.937, 104.604, 100.237, 81.040, 70.494, 63.501, 55.350, 42.006, 31.828, 31.773, 30.589, 8.051, 7.920.

(3) Preparation of 3-(2-benzyloxy-4-methoxyphenyl)-8,8-diethyl-2,3,4,8-tetrahydropyrano [2,3-f] chromene 3-(2-benzyloxy-4-methoxyphenyl)-8,8-diethyl-2,3,4,8-tetrahydropyrano [2,3-f] chromene was obtained in the same manner as in Example 13(3), except that 2-(2-benzyloxy-4-methoxyphenyl)-3-(2,2-diethyl-5-hydroxy-2H-1-benzopyran-6-yl) propan-1-ol obtained in (2) was used instead of 2-(2-benzyloxy-4-methoxyphenyl)-3-(2,2-dimethyl-5-hydroxy-2H-1-benzopyran-6-yl) propan-1-ol.

¹H-NMR (CDCl₃): 7.28~7.45 (m, 5H), 7.095 (d, 1H, J=8.0 Hz), 6.846 (d, 1H, J=8.0 Hz), 6.789 (d, 1H, J=10.0 Hz), 6.598 (d, 1H, J=2.0 Hz), 6.531 (dd, 1H, J=8.0, 2.0 Hz), 6.400 (d, 1H, J=8.0 Hz), 5.482 (d, 1H, J=10.0 Hz), 5.134 (s, 1H), 5.087 (s, 2H), 4.412 (m, 1H), 4.061 (t, 1H, J=10.0 Hz), 3.817 (s, 3H), 3.702 (m, 1H), 3.002 (dd, 1H, J=15.6, 10.8 Hz), 2.899 (dd, 1H, J=15.6, 4.4 Hz), 1.65~1.83 (m, 4H), 0.96~1.02 (m, 6H).

¹³C-NMR (CDCl₃): 159.490, 157.254, 152.699, 149.752, 136.848, 129.098, 128.615, 127.877, 127.684, 127.134, 126.304, 122.359, 118.237, 113.980, 109.504, 108.073, 104.606, 100.012, 81.135, 70.175, 70.077, 55.300, 31.834, 31.825, 31.334, 30.742, 8.029, 7.965.

(4) Preparation of 3-(2-hydroxy-4-methoxyphenyl)-8,8-diethyl-2,3,4,8,9,10-hexahydropyrano [2,3-f] chromene 3-(2-hydroxy-4-methoxyphenyl)-8,8-diethyl-2,3,4,8,9,10-hexahydropyrano [2,3-f] chromene (Compound 23) was obtained in the same manner as in Example 13(4), except that 3-(2-benzyloxy-4-methoxyphenyl)-8,8-diethyl-2,3,4,8-tetrahydropyrano [2,3-f] chromene obtained in (3) was used instead of 3-(2-benzyloxy-4-methoxylphenyl)-8,8-dimethyl-2,3,4,8-tetrahydropyrano [2,3-f] chromene.

¹H-NMR (CDCl₃): 7.027 (d, 1H, J=8.4 Hz), 6.843 (d, 1H, J=8.4 Hz), 6.493 (dd, 1H, J=8.4, 2.4 Hz), 6.422 (d, 1H, J=8.4 Hz), 6.357 (d, 1H, J=2.4 Hz), 5.184 (s, 1H), 4.398 (m, 1H, J=10.4, 2.0, 1.2 Hz), 4.026 (t, 1H, J=10.4 Hz), 3.766 (s, 3H), 3.498 (m, 1H), 3.022 (dd, 1H, J=15.6, 11.2 Hz), 2.896 (m, 1H, J=15.6, 6.8, 2.0 Hz), 2.619 (m, 2H), 1.787 (t, 2H, J=6.8 Hz), 1.55~1.75 (m, 4H), 0.88~0.95 (m, 6H).

¹³C-NMR (CDCl₃): 159.248, 154.383, 152.918, 152.031, 128.137, 127.390, 120.145, 112.642, 109.810, 109.416, 105.987, 102.114, 77.969, 70.004, 55.290, 31.826, 30.665, 28.123, 27.794, 27.458, 16.489, 7.592.

Experimental Example 1: Experiment of PTP1B Inhibition

With respect to PTP1B, the degrees of inhibition ($IC_{50}$ The half maximal inhibitory concentration) of glabridin, and compounds of Preparation Example 2 (Compound 1), Example 2 (Compound 3), Example 3 (Compound 4), Example 4 (Compound 5), Example 13 (Compound 14), Example 14 (Compound 15), Example 15 (Compound 16), Example 17 (Compound 18), Example 18 (Compound 19) and Example 20 (Compound 21) were compared to each other. For this purpose, the degree of inhibition activity for PTP1B was investigated by using 2 mM p-nitrophenyl phosphate (p-NPP) as a substrate to measure the dephosphorylation degree. First, PTP1B diluted with distilled water was reacted with 2 mM p-nitrophenyl phosphate {p-NPP, 0.1 M NaCl, 1 mM EDTA, 50 mM citrate pH 6.0, and 1 mM dithiothreitol (DTT)} and Compound 1 at various concentrations at 30° C. for 30 minutes, and then the reaction was terminated with a 1 N-sodium hydroxide (NaOH) solution. The absorbance of the samples thus prepared was measured to confirm the inhibition degree ($IC_{50}$: The half maximal inhibitory concentration) for PTP1B activity according to the concentration of Compound 1. Even for glabridin, Compound 3, Compound 4, Compound 5, Compound 14, Compound 15, Compound 16, Compound 18, Compound 19, and Compound 21, the same measurement was performed. The results are shown in the following Table 1 and FIG. 1.

TABLE 1

| Experimental group | $IC_{50} = \mu M$ |
| --- | --- |
| Glabridin | 48 |
| Compound 1 | 46 |
| Compound 3 | 7.0 |
| Compound 4 | 2.9 |
| Compound 5 | 2.8 |
| Compound 14 | 6.5 |
| Compound 15 | 8.6 |
| Compound 16 | 1.9 |
| Compound 18 | 3.4 |
| Compound 19 | 1.2 |
| Compound 21 | 2.3 |

As shown in Table 1 and FIG. 1, it may be confirmed that the compounds according to the present invention inhibited PTP1B 5 to 10 times better than glabridin.

Experimental Example 2: Experiment of Anti-Obesity Effect for DIO Mice

Five-week-old female C57BL/6 mice (Narabio Co., Ltd.) were purchased and fed with only high-fat diet for at least 10 weeks to produce diet induced obesity (DIC) mice. Samples were exactly taken from Preparation Example 1 (glabridin) and the compounds of Examples of the present invention (Compounds 1 to 5, 7, 9, 11, 14 to 16, 21, and 23) according to the administration dose and put into Falcon tubes, 3 ml of a 0.5% methyl cellulose aqueous solution was added thereto and a vortex mixer was used to primarily mix the ingredients in a soft manner, and then a homogenizer (30,000 rpm, Ultra-Turrax® T10 Basic, IKA) was used to treat the sample for 3 minutes while 1.5 ml of a 0.5% methyl cellulose aqueous solution was added thereto. The sample thus prepared was administered through oral gavage using a disposable plastic syringe once daily for 28 days (4 weeks). The body weight was measured twice a week while the DIO mice were bred in this manner. Based on the data thus calculated, the anti-obesity effect (%) was calculated according to the equation defined as follows.

Anti-Obesity Effect={(Body weight of control group)−(Body weight of experimental group)}/ (Body weight of control group)×100

The results obtained as above are shown in the following Table 2.

TABLE 2

| Compound No. | Anti-obesity effect (%) | Administration period and dose |
| --- | --- | --- |
| Glabridin | 2 | 4 weeks, 150 mg/kg |
| Compound 1 | 8 | 4 weeks, 150 mg/kg |
| Compound 2 | 8 | 4 weeks, 200 mg/kg |
| Compound 3 | 19 | 4 weeks, 200 mg/kg |
| Compound 4 | 18 | 4 weeks, 150 mg/kg |
| Compound 5 | 19 | 4 weeks, 150 mg/kg |
| Compound 7 | 14 | 4 weeks, 150 mg/kg |
| Compound 9 | 10 | 4 weeks, 150 mg/kg |
| Compound 11 | 8 | 4 weeks, 150 mg/kg |
| Compound 14 | 12 | 4 weeks, 150 mg/kg |
| Compound 15 | 14 | 4 weeks, 150 mg/kg |
| Compound 16 | 7 | 4 weeks, 150 mg/kg |
| Compound 21 | 16 | 4 weeks, 150 mg/kg |
| Compound 23 | 11 | 4 weeks, 200 mg/kg |

As shown in Table 2, it may be seen that the pyranochromenylphenol derivatives according to the present invention are by far better in anti-obesity activity than glabridin.

After the experiment was performed for 28 days (4 weeks) as described above, blood was simultaneously taken while the experimental animal was finally sacrificed, and each of the organs (liver, heart, kidney, pancreas, fat tissues and the like) was removed to measure the weight and observe peculiar matters.

TABLE 3

| Experimental group | Dose (mg/kg) | BMI | Liver (g) | Fat (g) | AST (U/L) | ALT (U/L) | LDL (mg/dL) | FFA (μEq/L) |
| --- | --- | --- | --- | --- | --- | --- | --- | --- |
| Glabridin | 150 | 4.2 | 1.23 | 2.70 | 90 | 41 | 10 | 1520 |
|  | {150} | {4.2} | {1.48} | {1.92} | {170} | {89} | {17} | {1913} |
| Compound 1 | 150 | 3.8 | 1.24 | 2.07 | 93 | 34 | 11 | 1400 |
| Compound 3 | {200} | {3.5} | {1.53} | {1.62} | {152} | {73} | {22} | {2390} |
| Compound 4 | (150) | (2.9) | (1.25) | (1.20) | (209) | (58) | (18) | (2380) |
| Compound 5 | (150) | (3.0) | (1.15) | (1.04) | (131) | (50) | (12) | (2310) |
| Compound 14 | 150 | 3.9 | 1.19 | 2.23 | 131 | 51 | 13 | 2160 |
| Compound 15 | 150 | 3.6 | 1.28 | 2.02 | 143 | 52 | 10 | 1760 |

TABLE 3-continued

| Experimental group | Dose (mg/kg) | BMI | Liver (g) | Fat (g) | AST (U/L) | ALT (U/L) | LDL (mg/dL) | FFA (µEq/L) |
|---|---|---|---|---|---|---|---|---|
| Compound 21 | 150 | 3.6 | 1.11 | 2.13 | 104 | 46 | 12 | 1520 |
| Control group Dio-mice | — | 4.4 {4.4} (3.6) | 1.30 {2.01} (1.19) | 2.67 {1.96} (2.41) | 212 {268} (126) | 94 {213} (80) | 29 {29} (21) | 2840 {2130} (4010) |
| Control group Lean mice | — | 3.1 {2.7} (2.7) | 1.19 {1.04} (0.95) | 0.77 {0.72} (0.53) | 76 {111} (81) | 32 {58} (29) | 11 {11} (9.3) | 2040 {1930} (2970) |

Dose: Administration dose
BMI: Body Mass Index
Liver: Weight of liver
Fat: Weight of fat removed around the epididymis and the kidney
AST: Aspartate aminotransferase
ALT: Alanine aminotransferase
LDL: Low density lipoprotein
FFA: Free fatty acid In Table 3, { }, ( ) and the like were used in order to differentiate experiments which had been performed at different periods. Experiments without the parenthesis were those simultaneously performed under the same conditions.

As shown in Table 3, it may be clearly seen that during the administration of the pyranochromenylphenol derivative of the present invention, a decrease in body weight of the DIO mice are closely associated with a decrease in weight of the fat tissue, and it may be confirmed that biochemical indices have been improved toward a more preferable direction while the BMI of the DIO mice was decreasing.

Experimental Example 3: Experiment of Glucose Uptake in $C_2C_{12}$ Cells

In terms of capacity of glucose uptake in $C_2C_{12}$ cells, the compound (Compound 15) of Example 14 of the present invention was compared with the existing Rosiglytazone and Metformin which were used or are currently used as a therapeutic agent for diabetes. The $C_2C_{12}$ cell was cultured in a Dulbecco's modified eagle medium (DMEM) supplemented with 10% fetal bovine serum (FBS), penicillin (120 unit/mL), and streptomycin (75 µg/mL), the medium used for differentiation was a DMEM medium supplemented with 1% horse serum, and the $C_2C_{12}$ cell was cultured in the DMEM medium for 4 days. The cell thus cultured was treated with Compound 15 in a low-glucose, serum-free medium supplemented with 2-[N-(7-nitrobenz-2-oxa-1,3-diazol-4-yl)amino]-2-deoxy-d-glucose (2-NBDG) for 24 hours to measure the glucose absorbance at an excitation wavelength of 485 nm and an emission wavelength of 535 nm using a fluorescent detector. The same experiment was performed on Rosiglytazone and Metformin. The experimental results are shown in the following Table 4.

TABLE 4

| Compound | Treatment concentration | 2-NBDG uptake (Fold Induction) |
|---|---|---|
| Control group | — | 1.00 |
| Rosiglytazone | 50 µM | 1.94 ± 0.15 |
| Metformin | 20 µM | 1.89 ± 0.03 |
| Compound 15 | 20 µM | 2.07 ± 0.13 |

As shown in Table 4, it may be confirmed that Compound 15 has a capacity of promoting glucose uptake better than that of the existing therapeutic agent for diabetes.

Experimental Example 4: Experiment of Anti-Diabetic Effects for db/db-Mice 5-week-old male C57BLKS/J-db/db mice (Central Lab. Animal Inc.) were purchased and acclimatized for 2 weeks, and then used in this experiment. Samples were exactly taken from the compounds prepared in Examples 4 and 15 of the present invention (Compounds 5 and 16) according to the administration dose and put into Falcon tubes, a 0.5% methyl cellulose aqueous solution stored refrigerated was placed at room temperature to allow the excipients to be warmed at room temperature, 16 ml of each of the excipients was added to a 50 ml Falcon tube, and a vortex mixer was used to primarily mix the ingredients in a soft manner, and then a suspension was obtained and homogenized by treating the sample for 3 minutes using a homogenizer (30,000 rpm, CPT-1600E, Kinemtica, Switzerland), and then ultrasonically treated for 30 minutes. The sample thus prepared was administered through oral gavage using a disposable plastic syringe equipped with a sonde once daily for 42 days (6 weeks).

The glycosylated hemoglobin (HbA1c) was measured while the db/db mice were bred. The gyclosylated hemoglobin was measured at 2 days prior to group separation, 4 weeks after administration, and 6 weeks after administration, and was measured by fasting the mice for 4 hours on the measurement date, collecting blood from the caudal vein before each material was administered, and using a device for measuring glycosylated hemoglobin (SD A1cCare, SD Biosensor, Inc., Korea). The results thus measured are shown in the following Table 5.

TABLE 5

| Compound | HbA1c (%) Before administration | 4 weeks | 6 weeks | Administration period and dose |
|---|---|---|---|---|
| Control group | 4.7 | 9.2 | 9.0 | — |
| Compound 5 | 4.7 | 5.3 | 5.7 | 6 weeks, 300 mg/kg |
| Compound 16 | 4.7 | 6.7 | 6.2 | 6 weeks, 300 mg/kg |

As shown in Table 5, it may be confirmed that the pyranochromenylphenol derivatives according to the present invention controlled blood glucose level to a nearly normal range (normal range: HbA1c 6.0 or less).

The mouse to which Compound 16 had been administered for 6 weeks in this experiment was finally sacrificed and autopsied to collect a liver, the liver was excised and each stained with hematoxylin and eosin (H&E) and perilipin antibody, the stained tissue was observed using a microscope, and the results are shown in FIGS. 2 to 5. The microscope photographs (FIGS. 2a, 3a, 4a and 5a) of the case in which Compound 16 had been administered were shown, and the photographs (FIGS. 2b, 3b, 4b and 5b) of a control group to which no drug was administered.

Figure 2A:
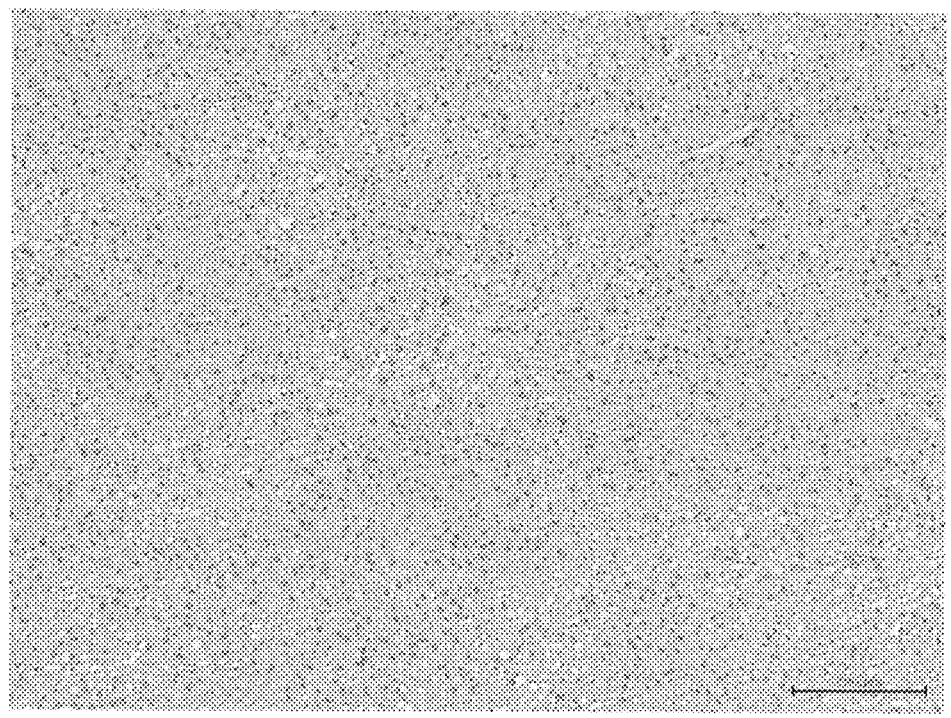
FIG. 2a is a microscope photograph (100 times magnification) of a liver tissue stained with hematoxylin and eosin (H&E), which was collected from a mouse to which Compound 16 of the present invention had been administered for 6 weeks, and which was finally sacrificed and autopsied.
Figure 2B:
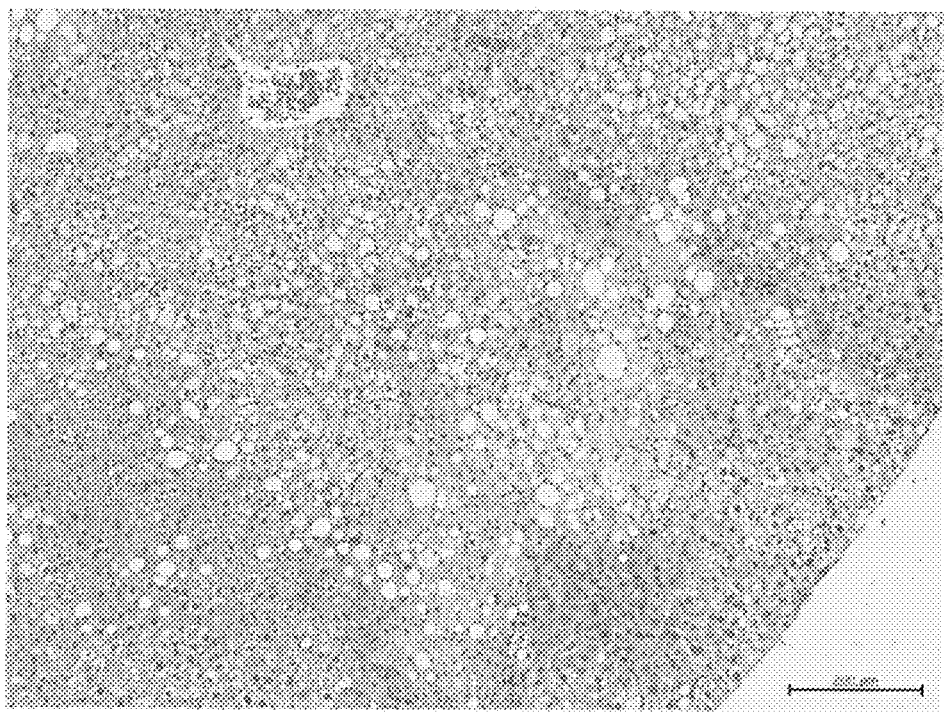
FIG. 2b is a microscope photograph of a control group to which Compound 16 was not administered.
Figure 3A:
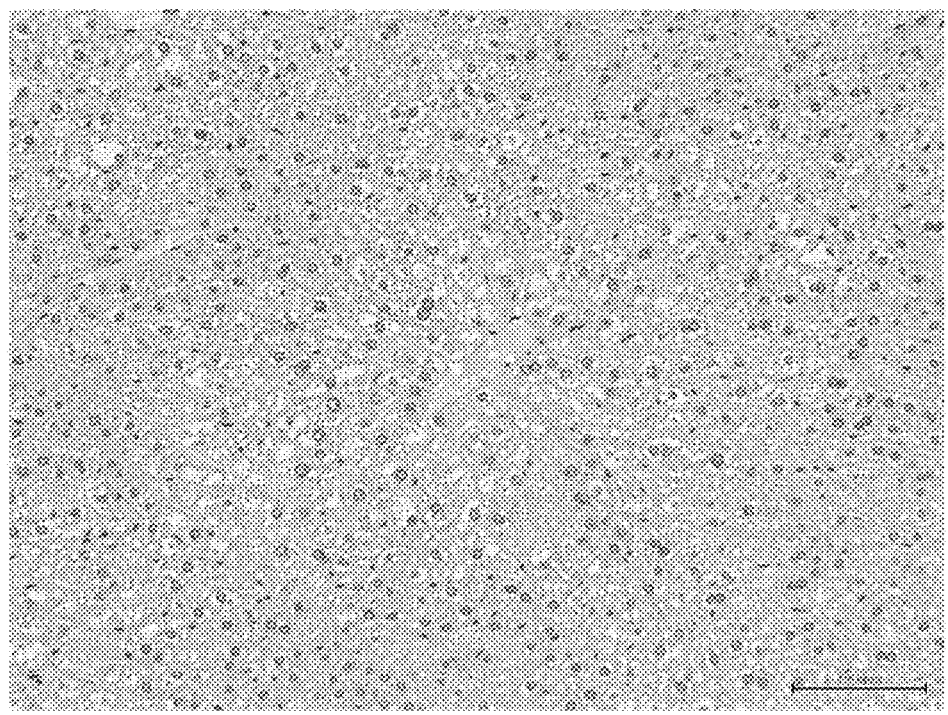
FIG. 3a is a microscope photograph (200 times magnification) of a liver tissue stained with hematoxylin and eosin (H&E), which was collected from a mouse to which Compound 16 of the present invention had been administered for 6 weeks, and which was finally sacrificed and autopsied.
Figure 3B:
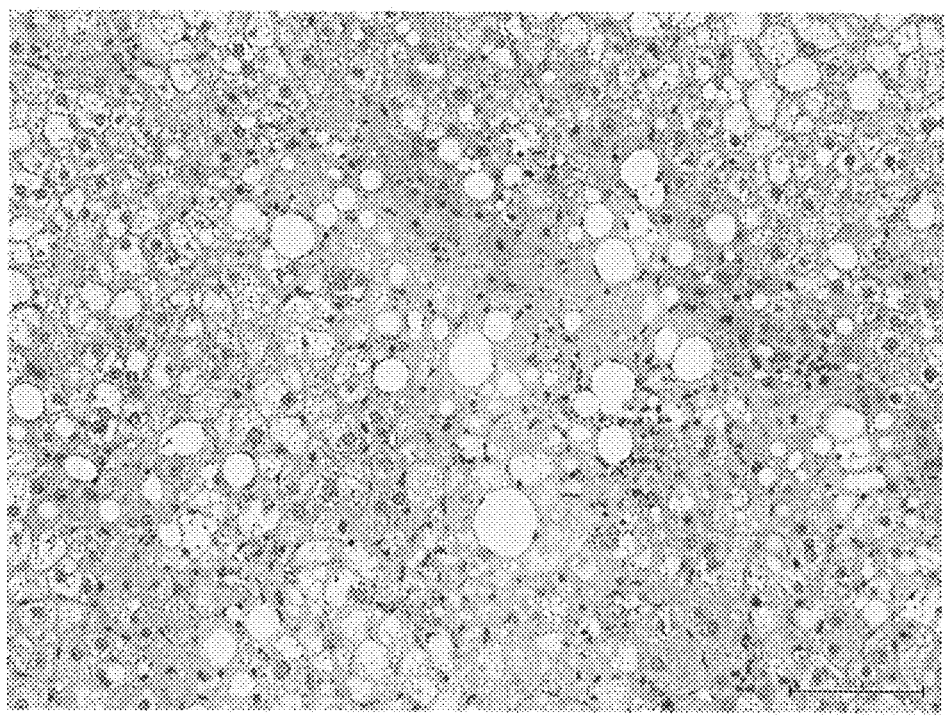
FIG. 3b is a microscope photograph of a control group to which Compound 16 was not administered.
Figure 4A:
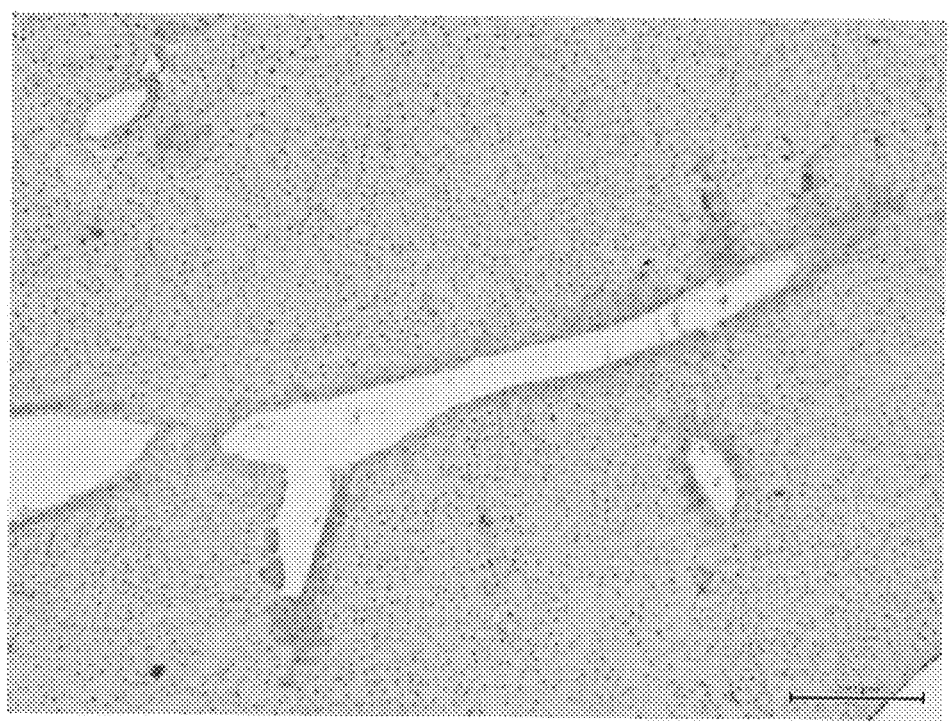
FIG. 4a is a microscope photograph (100 times magnification) of a liver tissue stained with perilipin antibody, which was collected from a mouse to which Compound 16 of the present invention had been administered for 6 weeks, and which was finally sacrificed and autopsied.
Figure 4B:
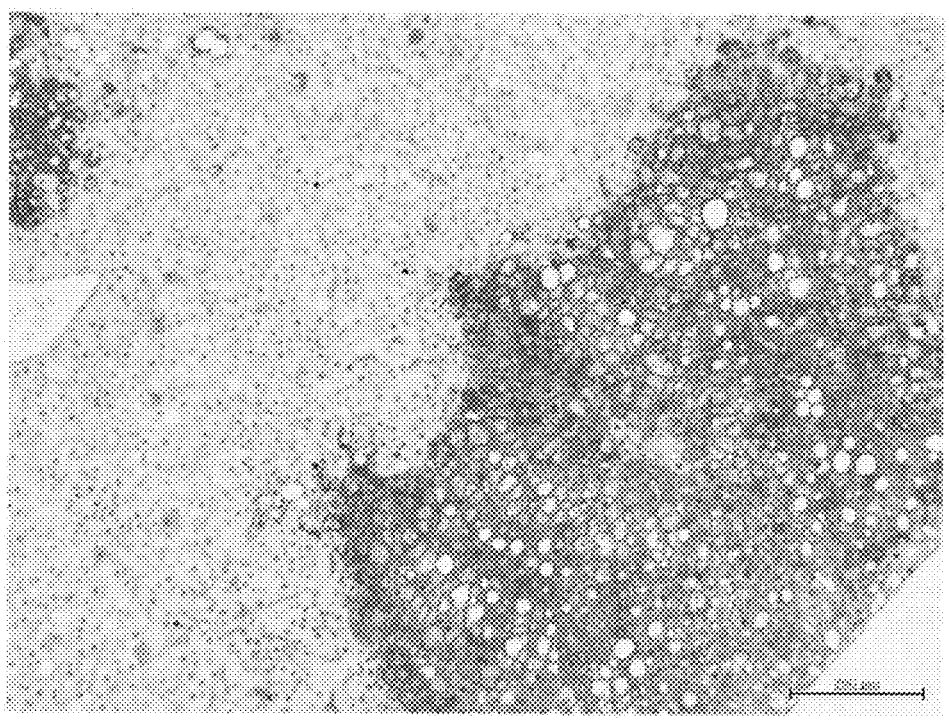
FIG. 4b is a microscope photograph of a control group to which Compound 16 was not administered.
Figure 5A:
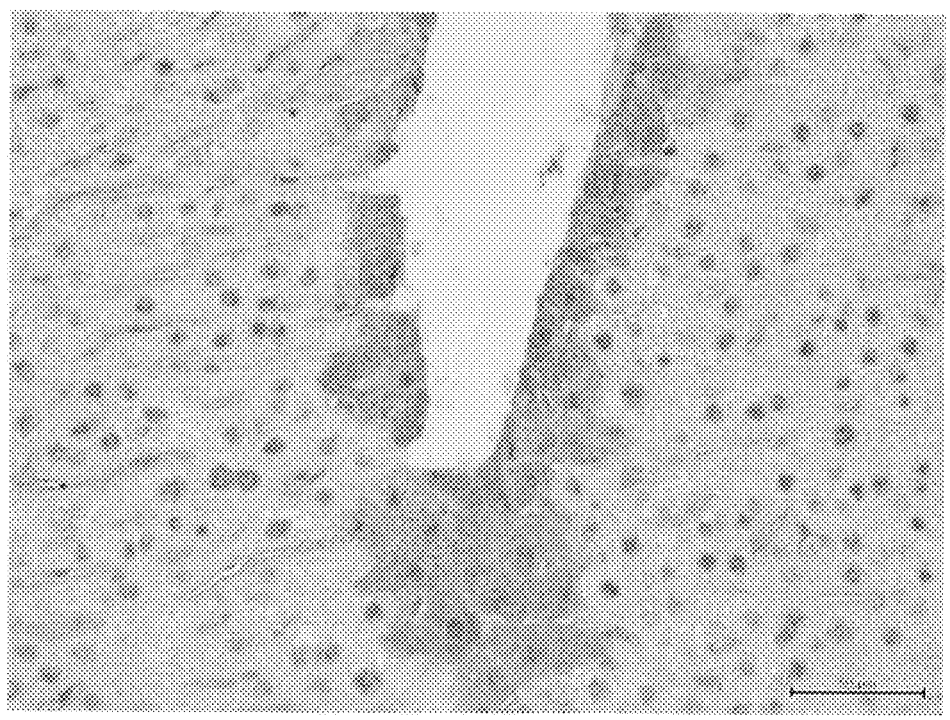
FIG. 5a is a microscope photograph (200 times magnification) of a liver tissue stained with perilipin antibody, which was collected from a mouse to which Compound 16 of the present invention had been administered for 6 weeks, and which was finally sacrificed and autopsied.
Figure 5B:
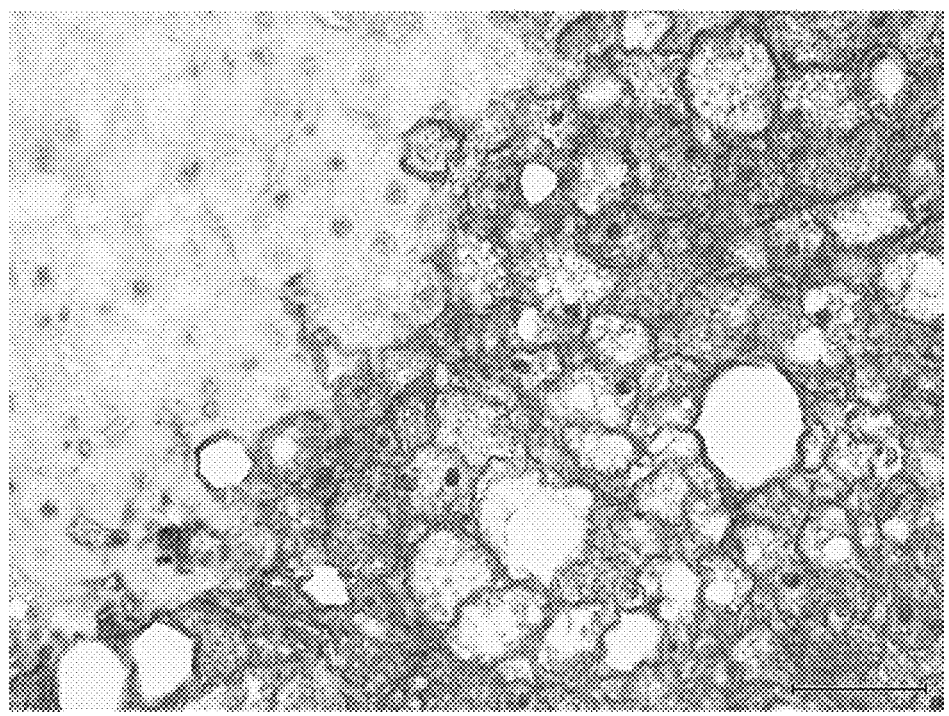
FIG. 5b is a microscope photograph of a control group to which Compound 16 was not administered.

FIG. 2a is a microscope photograph (100 times magnification) of a liver tissue stained with hematoxylin and eosin (H&E), which was collected from a mouse to which Compound 16 of the present invention had been administered for 6 weeks, and which was finally sacrificed and autopsied. FIG. 2b is a microscope photograph of a control group to which Compound 16 was not administered. FIG. 3a is a microscope photograph (200 times magnification) of a liver tissue stained with hematoxylin and eosin (H&E), which was collected from a mouse to which Compound 16 of the present invention had been administered for 6 weeks, and which was finally sacrificed and autopsied. FIG. 3b is a microscope photograph of a control group to which Compound 16 was not administered. FIG. 4a is a microscope photograph (100 times magnification) of a liver tissue stained with perilipin antibody, which was collected from a mouse to which Compound 16 of the present invention had been administered for 6 weeks, and which was finally sacrificed and autopsied. FIG. 4b is a microscope photograph of a control to which Compound 16 was not administered. FIG. 5a is a microscope photograph (200 times magnification) of a liver tissue stained with perilipin antibody, which was collected from a mouse to which Compound 16 of the present invention had been administered for 6 weeks, and which was finally sacrificed and autopsied.

As illustrated in FIGS. 2 to 5, unlike liver tissues from a control group in which many large adipocytes are present and many dead cells are found, liver tissues from mice to which Compound 16 had been administered had small and compact adipocytes, so that the mice are generally healthy.

Experimental Example 5: BV2 Cell NO Assay Experiment (Experiment of Confirming Anti-Inflammatory Efficacy)

BV2 microglia cells were cultured at a concentration of $1 \times 10^4$ cells/well in a 96 well plate for 24 hours, and subjected to pre-treatment with a compound at Concentration 3 (in the case of glabridin, at a concentration of 5 uM, 10 um, and 20 uM, and in the case of Compound 4, Compound 5, Compound 15, Compound 16, and Compound 18, at a concentration of 2.5 uM, 5 uM and 10 uM) which does not suppress the cells from proliferating for 3 hours. After the pretreatment, 0.5 mg/ml of the MTT (Sigma, M2128) reagent was further added thereto. After the cells were cultured in a 5% $CO_2$ incubator, the supernatant was discarded, 150 µl of DMSO was added and was shaken for 30 minutes, and an ELISA micro plate reader (Bio Rad Laboratories Inc., California, USA, Model 680) was used to measure the absorbance at a wavelength of 540 nm. All the experimental values were calculated as an average value of three repeated experimental values of the cell protection rate for the control group, and an experiment of suppressing the NO production for each compound was carried out at a concentration in which no cytotoxicity was shown.

Figure 6:
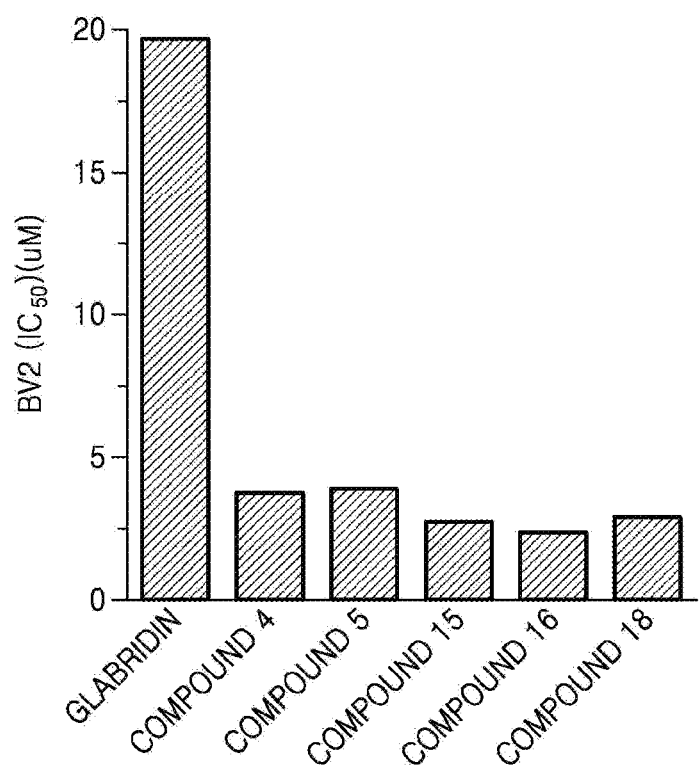
FIG. 6 is a graph showing the results of an experiment of confirming the anti-inflammatory efficacy of the pyranochromenylphenol derivative according to the present invention.

BV2 microglia cells were cultured at a level of $5 \times 10^5$ cells/well in a 24 well plate for 24 hours, the medium was removed after 24 hours, the cells were subjected to pre-treatment with the compound at Concentration 3 (in the case of glabridin, at a concentration of 5 uM, 10 um, and 20 uM, and in the case of Compound 4, Compound 5, Compound 15, Compound 16, and Compound 18, at a concentration of 2.5 uM, 5 uM and 10 uM) which does not suppress the cells from proliferating for 3 hours, and then treated with LPS (1 µg/ml), and after 24 hours, the amount of NO secreted from the cells to the medium was reacted using Griess reagent (0.1% (w/v) N-(1-naphathyl)-ethylenediamine and 1% (w/v) sulfanilamide in 5% (v/v) phosphoric acid). After the reaction, an ELISA micro plate reader (Bio Rad Laboratories Inc., California, USA, Model 680) was used to measure the absorbance at a wavelength of 540 nm. The suppression rate was calculated as a difference in amount of NO produced between the control group and the experimental group, and as shown in the following Table 6 and FIG. 6, Compounds 4, 5, 15, 16, 18, and the like of the present invention were excellent in the effect of suppressing the production of NO, and the effect is also about 5 times to about 9 times better than that of glabridin.

TABLE 6

| Compound | BV2 ($IC_{50}$) (µM) |
|---|---|
| Glabridin | 19.6 |
| Compound 4 | 3.7 |
| Compound 5 | 3.8 |
| Compound 15 | 2.7 |
| Compound 16 | 2.3 |
| Compound 18 | 2.8 |

Experimental Example 6: RAW265.7 Macrophage NO Assay Experiment (Experiment of Confirming Anti-Inflammatory Efficacy)

RAW264.7 macrophages were cultured at a concentration of $1 \times 10^4$ cells/well in a 96 well plate for 24 hours, and subjected to pre-treatment with a compound at three concentrations (in the case of glabridin, at a concentration of 10 uM, 20 uM, and 40 uM, and in the case of Compound 4, Compound 5, Compound 15, Compound 16, and Compound 18, at a concentration of 5 uM, 10 uM and 20 uM) which does not suppress cells from proliferating for 3 hours. After the pretreatment, the MTT (Sigma, M2128) reagent at a concentration of 0.5 mg/ml was further added thereto. After the cells were cultured in a 5% $CO_2$ incubator for 4 hours, the supernatant was discarded, 150 µl of DMSO was added and was shaken for 30 minutes, and an ELISA micro plate reader (Bio Rad Laboratories Inc., California, USA, Model 680) was used to measure the absorbance at a wavelength of 540 nm. All the experimental values were calculated as an average value of three repeated experimental values of the cell protection rate for the control group, and an experiment of suppressing the NO production for each compound was carried out at a concentration in which no cytotoxicity was shown.

RAW264.7 macrophages were cultured at a level of $5 \times 10^5$ cells/well in a 24 well plate for 24 hours, the medium was removed after 24 hours, the cells were subjected to pre-treatment with the compound at three concentrations (in the case of glabridin, at a concentration of 10 uM, 20 uM, and 40 uM, and in the case of Compound 4, Compound 5, Compound 15, Compound 16, and Compound 18, at a concentration of 5 uM, 10 uM and 20 uM) which does not suppress the cells from proliferating for 3 hours, and then treated with LPS (1 µg/ml), and after 24 hours, the amount of NO secreted from the cells to the medium was reacted using Griess reagent (0.1% (w/v) N-(1-naphathyl)-ethylene-diamine and 1% (w/v) sulfanilamide in 5% (v/v) phosphoric acid). After the reaction, an ELISA micro plate reader (Bio Rad Laboratories Inc., California, USA, Model 680) was used to measure the absorbance at a wavelength of 540 nm. The suppression rate was calculated as a difference in amount of NO produced between the control group and the experimental group, and as shown in the following Table 7, Compounds 4, 5, 15, 16, 18, and the like of the present invention were excellent in the effect of suppressing the production of NO.

TABLE 7

| Compound | RAW264.7 ($IC_{50}$) (μM) |
|---|---|
| Glabridin | 9.3 |
| Compound 4 | 8.6 |
| Compound 5 | 5.2 |
| Compound 15 | 6.8 |
| Compound 16 | 4.4 |
| Compound 18 | 5.6 |

Experimental Example 7: Experiment of Comparing Chemical Stability

The relative chemical stability of glabridin of Preparation Example 1, Example 3 (Compound 4), Example 4 (Compound 5) and Example 14 (Compound 15) were compared with each other. That is, 50 mg of each of glabridin, Compound 4, Compound 5, and Compound 15 was exactly weighed, dissolved in 50 ml of 1% HCl in MeOH and 10 ml of 1% NaOH in MeOH, and the concentrations of the compounds were examined by HPLC at each time level of 0, 8 hrs, 12 hrs, 24 hrs, 48 hrs, and 72 hrs. At this time, the concentrations of the compounds remaining in 1% HCl in MeOH and 1% NaOH in MeOH were determined using an internal standard (Compound 14 of Example 13). That is, 10 mg of Compound 14 was exactly weighed and dissolved in 100 ml of acetonitrile, 9 ml of this solution was mixed with 1 ml of the sample aliquoted at each time level, the mixture was analyzed by HPLC, and the concentrations of the compounds in the internal standard and in the above samples were determined by comparing the initial values.

Figure 7:
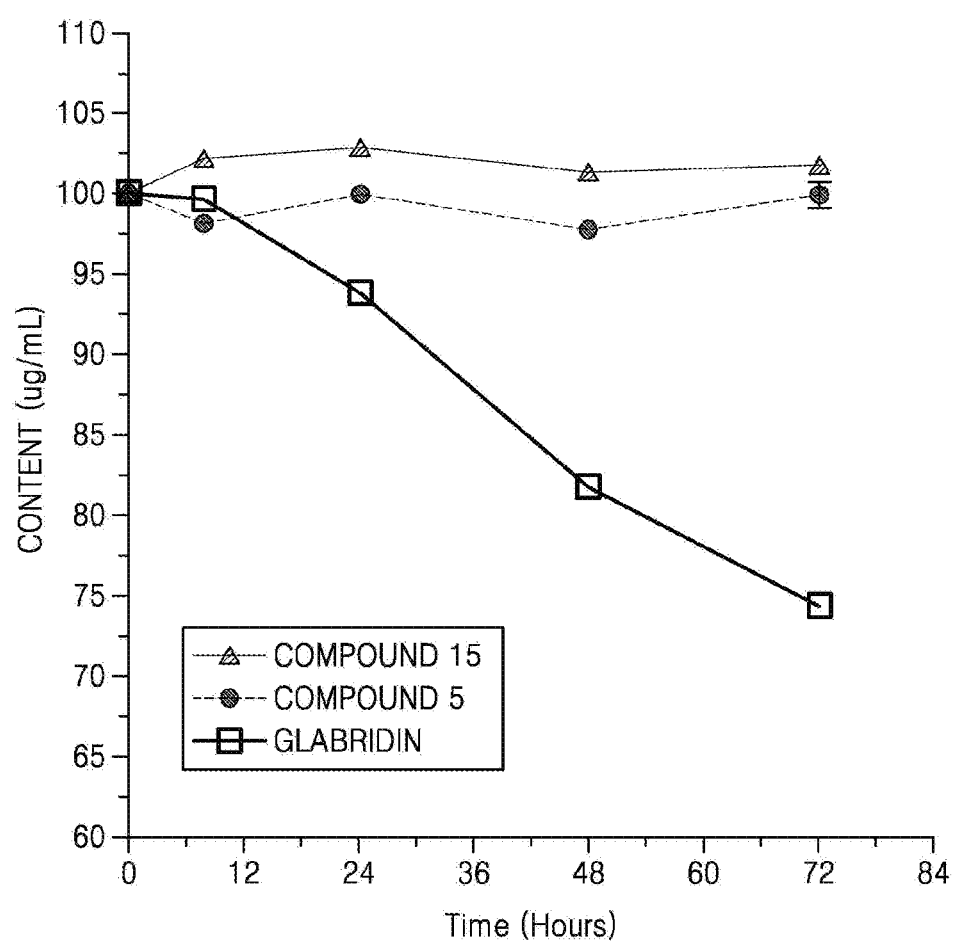
FIG. 7 is a graph showing stability of the pyranochromenylphenol derivative according to the present invention in an acidic solution.
Figure 8:
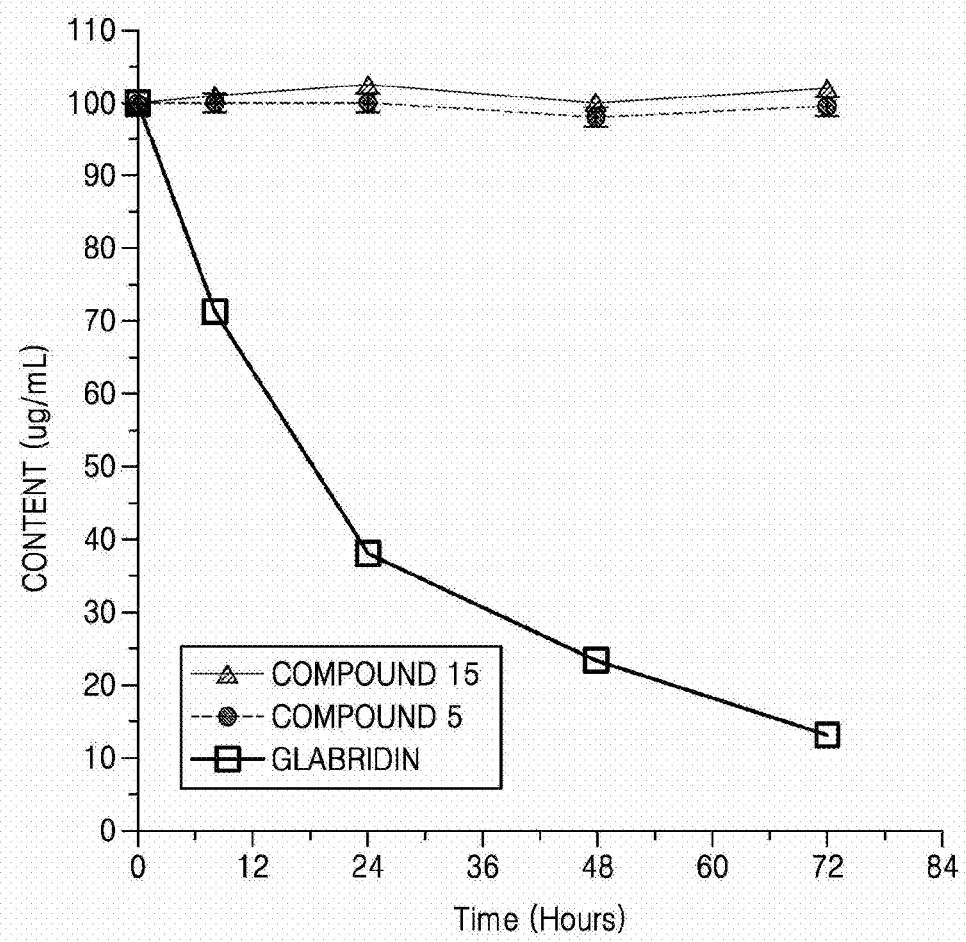
FIG. 8 is a graph showing stability of the pyranochromenylphenol derivative according to the present invention in an alkaline solution.

The concentrations of the compounds remaining in 1% HCl in MeOH and 1% NaOH in MeOH at each time level are in the following Table 8 and FIG. 7 and the following Table 9 and FIG. 8, respectively.

The numerical values exceeding 100% in the following Tables 8 and 9 show those measured at a concentration is slightly higher than the initial measurement value, and this is due to the fact that an average value of the measured values was simply shown without considering a statistical error generated during the measurement. Since the measured value of about 95% or more is deemed to have practically no change in concentration, it may be seen that the compounds of the present invention are excellent in chemical stability.

TABLE 8

| 1% HCl in MeOH | 0 | 8 h | 24 h | 48 h | 72 h |
|---|---|---|---|---|---|
| Glabridin | 100% | 99% | 94% | 82% | 74% |
| Compound 4 | 100% | 99% | 101% | 101% | 100% |
| Compound 5 | 100% | 102% | 102% | 101% | 101% |
| Compound 15 | 100% | 98% | 100% | 98% | 100% |

TABLE 9

| 1% NaOH in MeOH | 0 | 8 h | 24 h | 48 h | 72 h |
|---|---|---|---|---|---|
| Glabridin | 100% | 71% | 38% | 23% | 13% |
| Compound 4 | 100% | 101% | 101% | 99% | 100% |
| Compound 5 | 100% | 101% | 102% | 100% | 102% |
| Compound 15 | 100% | 100% | 100% | 98% | 100% |

As shown in Tables 8 and 9, it may be confirmed that unlike glabridin, Compound 4, Compound 5 and Compound 15 according to the present invention were very stable until 3 days (72 hours) even under the conditions of 1% HCl in MeOH and 1% NaOH in MeOH.

What is claimed is:

1. A compound of the following Formula (I), a pharmaceutically acceptable salt thereof:

[Formula I]

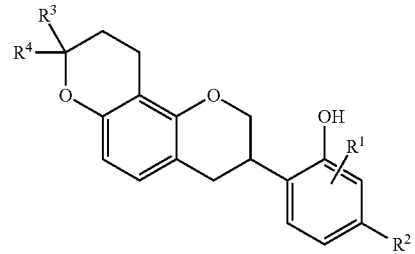

(I)

in the formula,
R¹ is a hydrogen atom, methyl, or a halogen atom;
R² is a hydrogen atom; a straight or branched $C_1$-$C_6$ alkyl group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; a halogen atom; a straight or branched $C_2$-$C_6$ alkoxy group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; $C_1$ alkoxy group substituted with a straight or branched $C_1$-$C_5$ alkyl group, a halogen atom, a straight or branched $C_1$-$C_5$ alkoxy group, or a straight or branched $C_1$-$C_3$ thioalkyl group; or a straight or branched $C_1$-$C_4$ thioalkyl group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; and
R³ and R⁴ are each independently a hydrogen atom, or a $C_1$-$C_2$ alkyl group.

2. The compound of Formula (I), or the pharmaceutically acceptable salt thereof of claim 1, wherein R¹ is a hydrogen atom, and R² is a hydrogen atom; a straight or branched $C_1$-$C_6$ alkyl group; a straight or branched $C_2$-$C_5$ alkoxy group; or a straight or branched $C_1$-$C_3$ thioalkyl group.

3. The compound of Formula (I), or the pharmaceutically acceptable salt thereof of claim 2, wherein R¹ is a hydrogen atom, and R² is methyl, ethyl, n-propyl, n-butyl, ethoxy, n-propoxy, n-butoxy or methoxymethoxy.

4. The compound of Formula (I), or the pharmaceutically acceptable salt thereof of claim 1, wherein the compound of Formula (I) is any one of the following compounds:

Compound 2
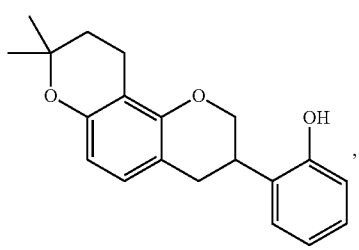
Compound 8
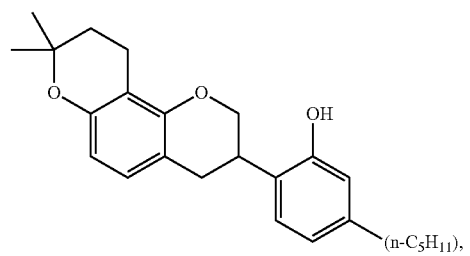
Compound 3
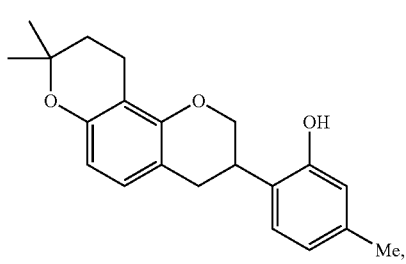
Compound 9
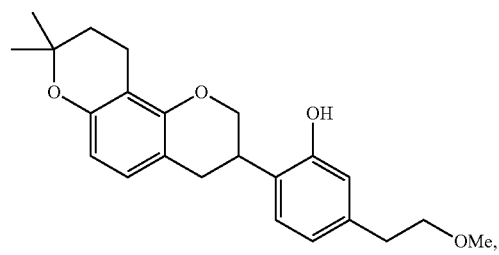
Compound 4
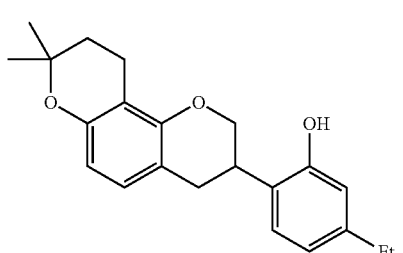
Compound 10
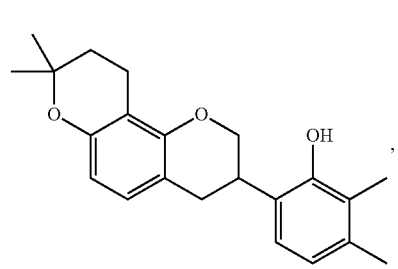
Compound 5
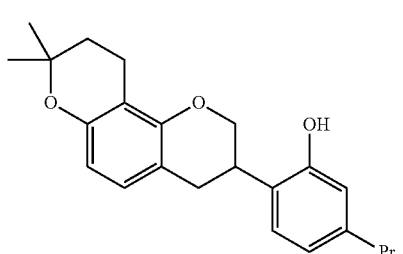
Compound 11
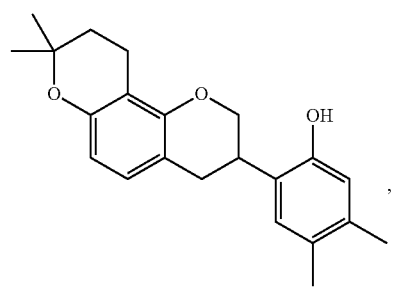
Compound 6
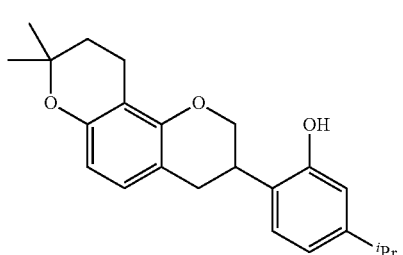
Compound 12
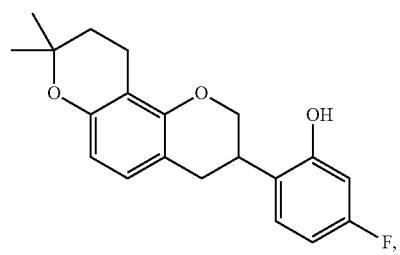
Compound 7
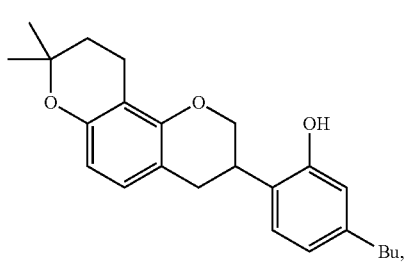
Compound 13
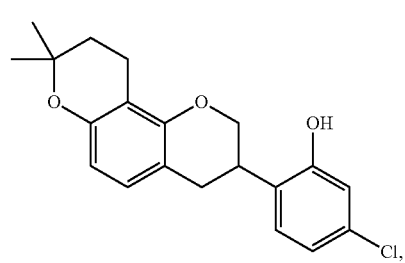

-continued

Compound 15
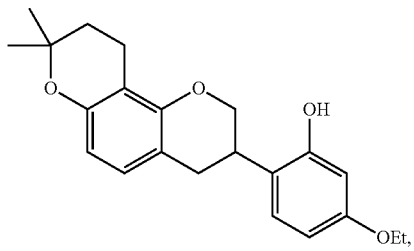
Compound 16
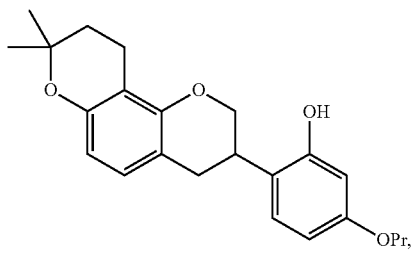
Compound 17
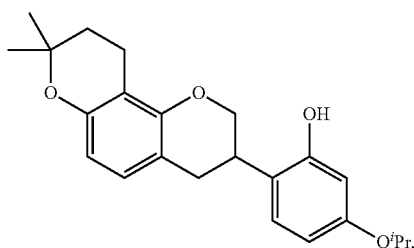
Compound 18
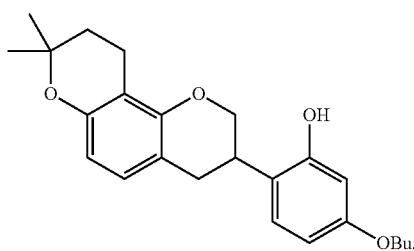
Compound 19
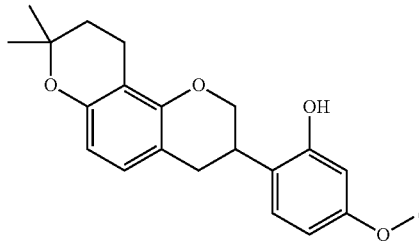
Compound 20
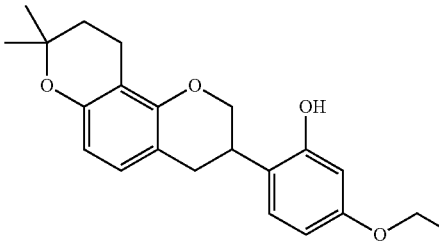, -continued Compound 21
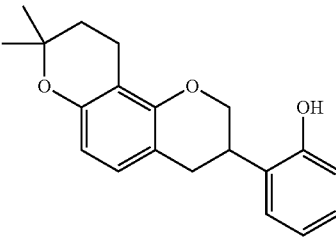
Compound 22
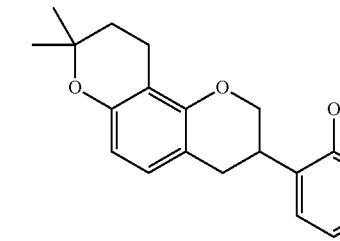

5. A method of treating a metabolic syndrome in a subject, comprising administering to the subject a therapeutically effective amount of a compound of the following Formula (I'), or a pharmaceutically acceptable salt thereof:

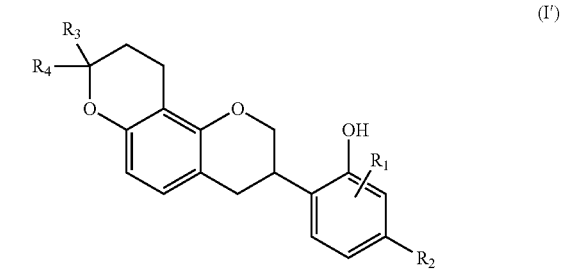

(I')

in the formula,
$R^1$ is a hydrogen atom, methyl, methoxy, or a halogen atom;
$R^2$ is a hydrogen atom; a hydroxy group; a straight or branched $C_1$-$C_6$ alkyl group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; a halogen atom; a straight or branched $C_1$-$C_6$ alkoxy group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; or a straight or branched $C_1$-$C_4$ thioalkyl group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; and
$R^3$ and $R^4$ are each independently a hydrogen atom, or a $C_1$-$C_2$ alkyl group.

6. The method of claim 5, wherein in Formula (I'), $R^1$ is a hydrogen atom, and $R^2$ is a hydrogen atom; a hydroxy group; a straight or branched $C_1$-$C_6$ alkyl group; a straight or branched $C_1$-$C_5$ alkoxy group; or a straight or branched $C_1$-$C_3$ thioalkyl group.

7. The method of claim 5, wherein in Formula (I'), R¹ is a hydrogen atom, and R² is methyl, ethyl, n-propyl, n-butyl, ethoxy, n-propoxy, n-butoxy or methoxymethoxy.
8. The method of claim 5, wherein the compound of Formula (I') is one or more of the following compounds:
Compound 1
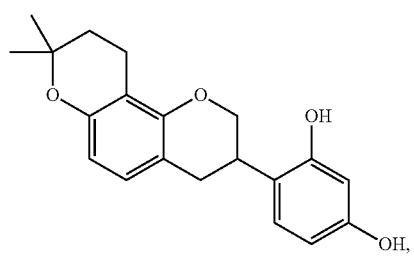
Compound 2
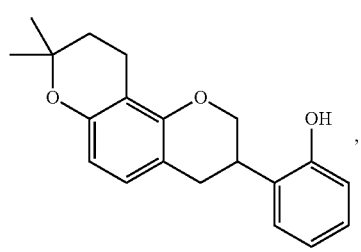
Compound 3
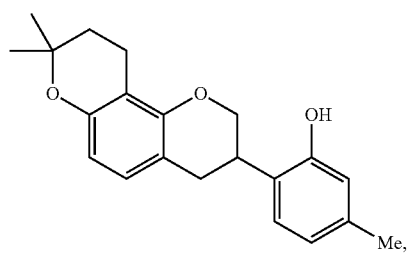
Compound 4
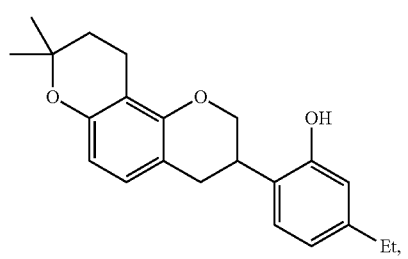
Compound 5
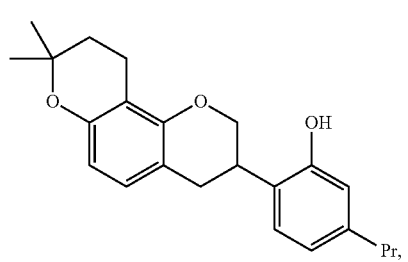
-continued
Compound 6
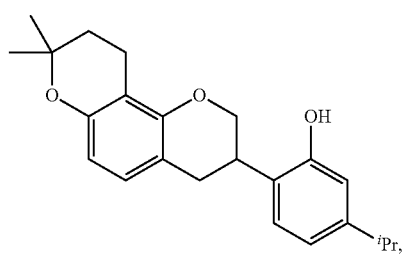
Compound 7
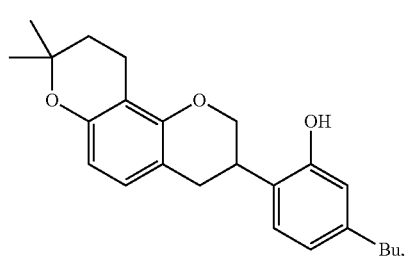
Compound 8
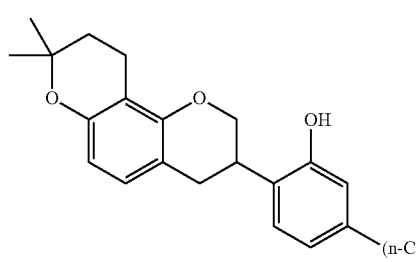
Compound 9
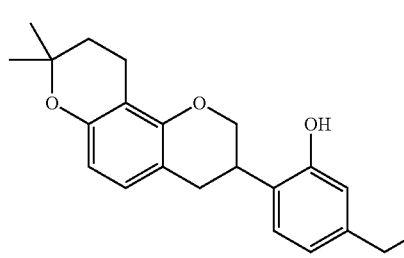
Compound 10
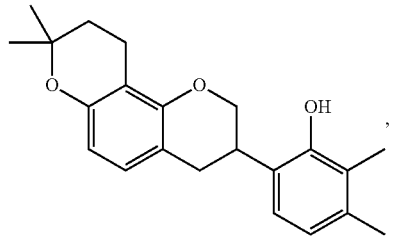
Compound 11
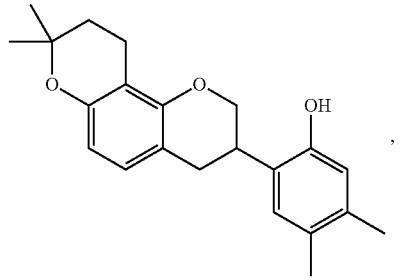

Compound 12
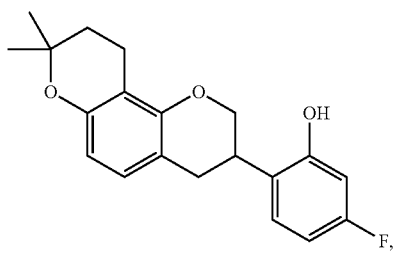
Compound 13
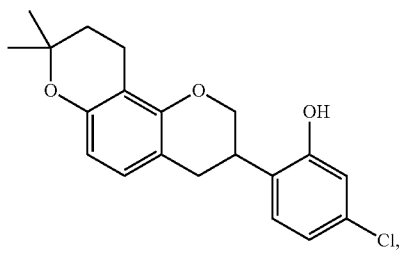
Compound 14
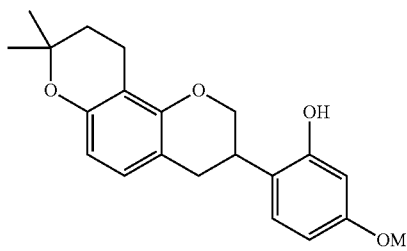
Compound 15
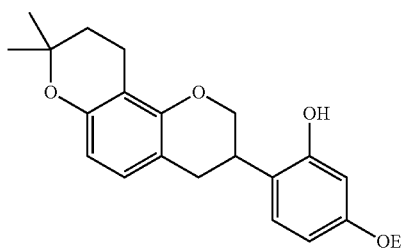
Compound 16
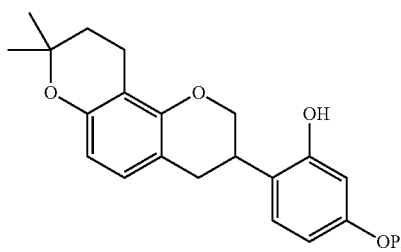
Compound 17
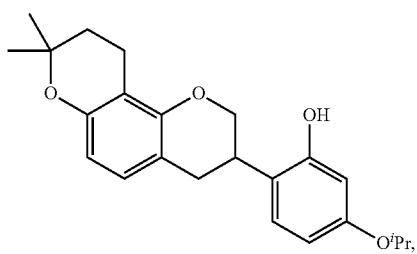
Compound 18
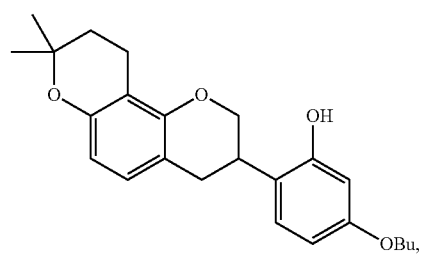
Compound 19
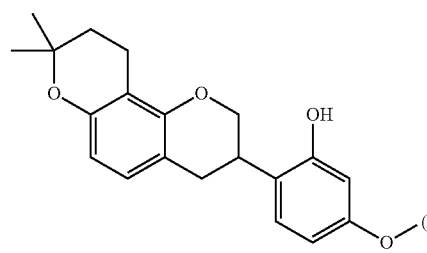
Compound 20
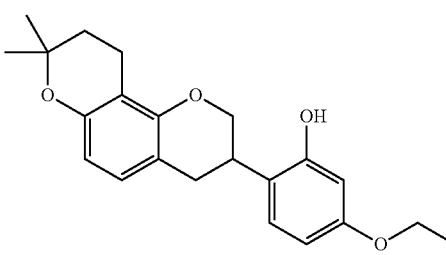
Compound 21
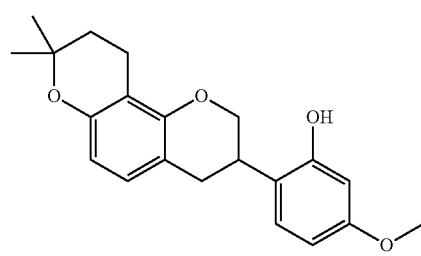
Compound 22
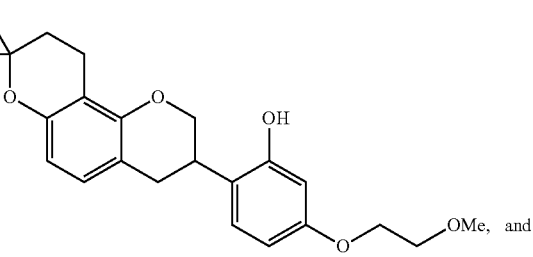

Compound 23

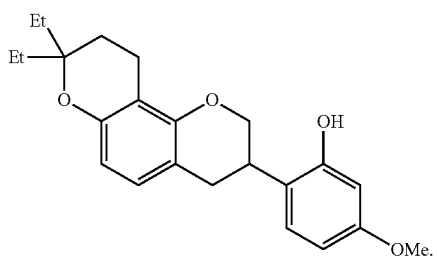

9. The method of claim 5, wherein the metabolic syndrome is one or more of obesity, diabetes, hyperlipidemia, and fatty liver.

10. The method of claim 9, wherein the diabetes is type 2 diabetes mellitus.

11. The method of claim 5, wherein the metabolic syndrome is a complex disease of type 2 diabetes mellitus and obesity.

12. A method of treating an inflammatory disease in a subject, wherein the inflammatory disease is rheumatoid arthritis, degenerative arthritis, asthma, atopy, or myocardial infarction, comprising administering to the subject a therapeutically effective amount of a compound of the following Formula (I'), for a pharmaceutically acceptable salt thereof:

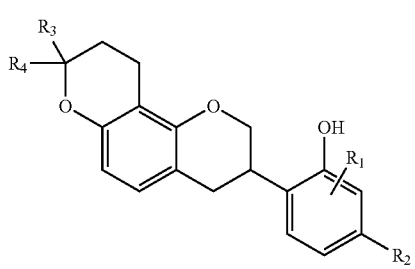

(I')

in the formula,
R$^1$ is a hydrogen atom, methyl, methoxy, or a halogen atom;
R$^2$ is a hydrogen atom; a hydroxy group; a straight or branched C$_1$-C$_6$ alkyl group unsubstituted or substituted with a straight or branched C$_1$-C$_5$ alkyl group, a halogen atom, a straight or branched C$_1$-C$_5$ alkoxy group, or a straight or branched C$_1$-C$_3$ thioalkyl group; a halogen atom; a straight or branched C$_1$-C$_6$ alkoxy group unsubstituted or substituted with a straight or branched C$_1$-C$_5$ alkyl group, a halogen atom, a straight or branched C$_1$-C$_5$ alkoxy group, or a straight or branched C$_1$-C$_3$ thioalkyl group; or a straight or branched C$_1$-C$_4$ thioalkyl group unsubstituted or substituted with a straight or branched C$_1$-C$_5$ alkyl group, a halogen atom, a straight or branched C$_1$-C$_5$ alkoxy group, or a straight or branched C$_1$-C$_3$ thioalkyl group; and
R$^3$ and R$^4$ are each independently a hydrogen atom, or a C$_1$-C$_2$ alkyl group.

13. The method of claim 12, wherein in Formula (I'), R$^1$ is a hydrogen atom, and R$^2$ is a hydrogen atom; a hydroxy group; a straight or branched C$_1$-C$_6$ alkyl group; a straight or branched C$_1$-C$_5$ alkoxy group; or a straight or branched C$_1$-C$_3$ thioalkyl group.

14. The method of claim 12, wherein in Formula (I'), R$^1$ is a hydrogen atom, and R$^2$ methyl, ethyl, n-propyl, n-butyl, ethoxy, n-propoxy, n-butoxy or methoxymethoxy.

15. The method of claim 12, wherein the compound of Formula (I') is one or more of the following compounds:

Compound 1

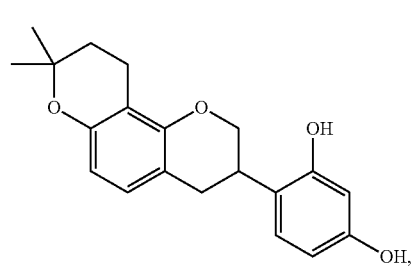

Compound 2

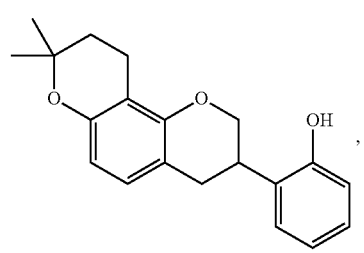

Compound 3

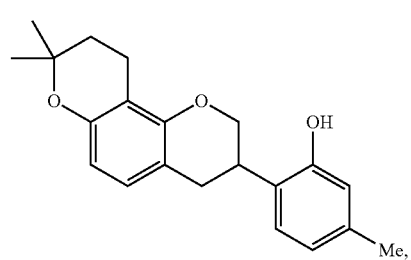

Compound 4

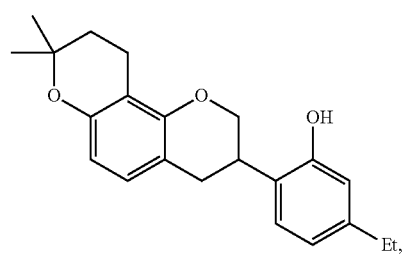

Compound 5

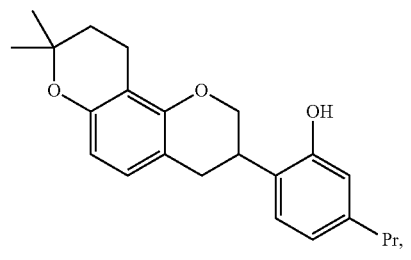

-continued
Compound 6
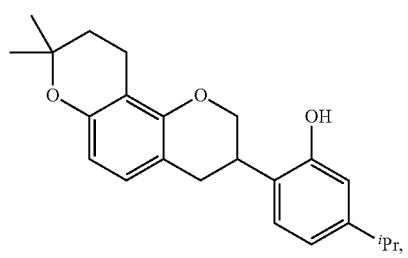
iPr,
Compound 7
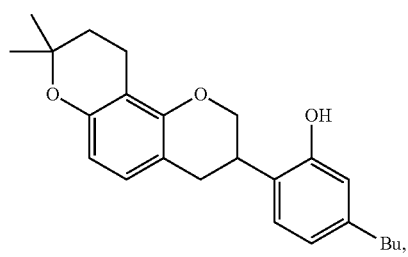
Bu,
Compound 8
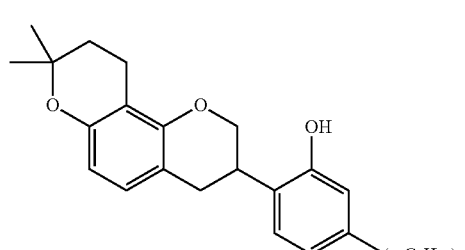
(n-C₅H₁₁),
Compound 9
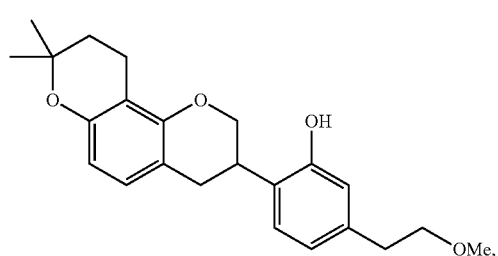
OMe,
Compound 10
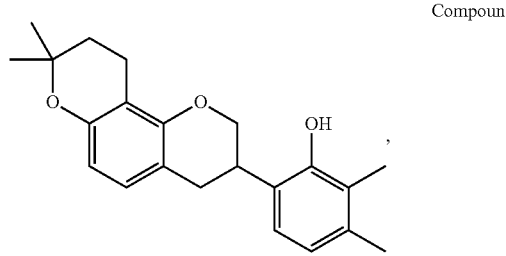
Compound 11
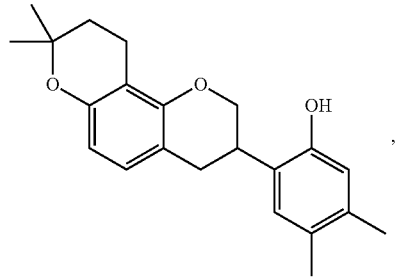
Compound 12
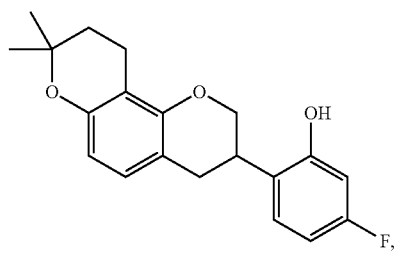
F,
Compound 13
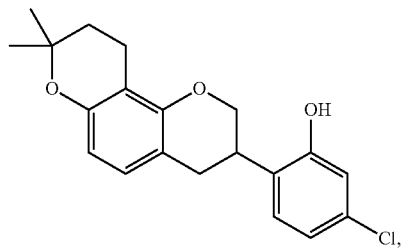
Cl,
Compound 14
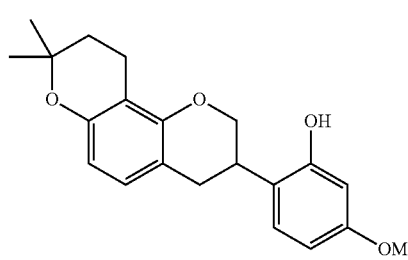
OMe,
Compound 15
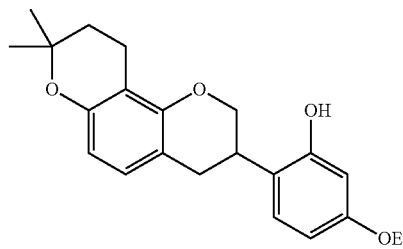
OEt,
Compound 16
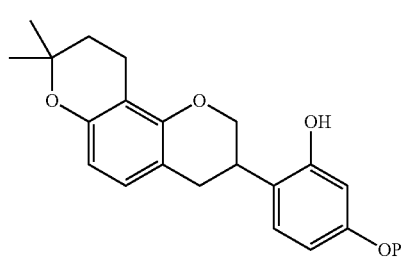
OPr,
Compound 17
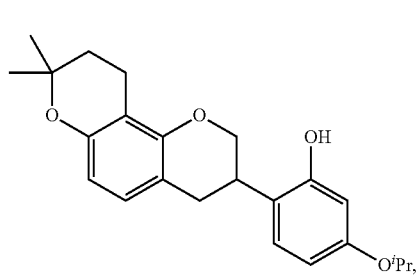
OiPr, Compound 18

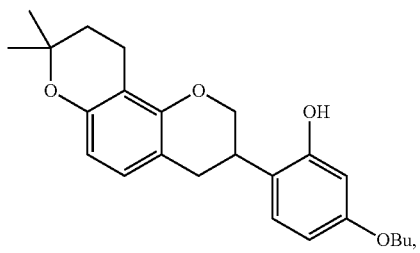

Compound 19

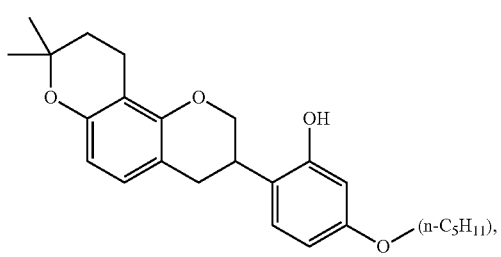

Compound 20

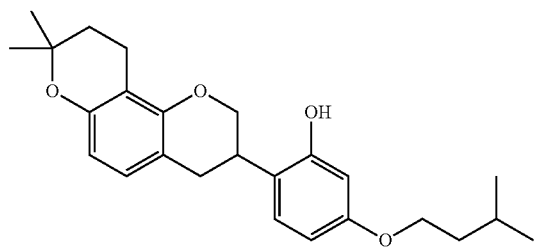

Compound 21

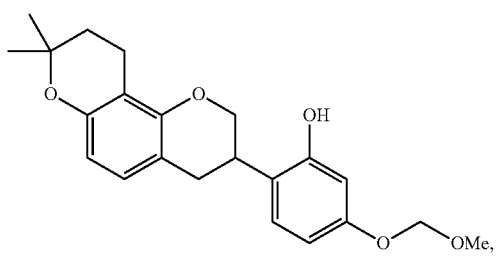

Compound 22

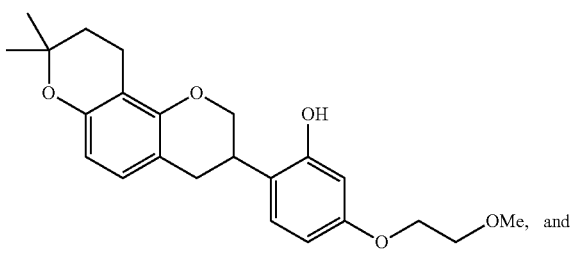

Compound 23

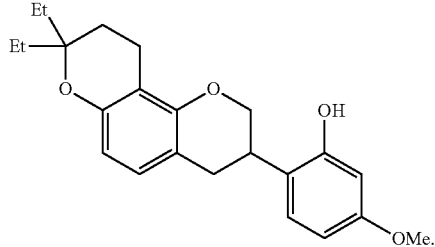

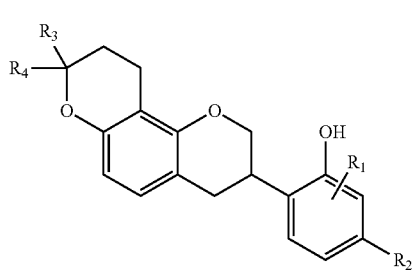

16. A pharmaceutical composition comprising a compound of the following Formula (I'), or a pharmaceutically acceptable salt thereof:

(I')

in the formula, $R^1$ is a hydrogen atom, methyl, or a halogen atom;

$R^2$ is a hydrogen atom; a straight or branched $C_1$-$C_6$ alkyl group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; a halogen atom; a straight or branched $C_2$-$C_6$ alkoxy group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; $C_1$ alkoxy group substituted with a straight or branched $C_1$-$C_5$ alkyl group, a halogen atom, a straight or branched $C_1$-$C_5$ alkoxy group, or a straight or branched $C_1$-$C_3$ thioalkyl group; or a straight or branched $C_1$-$C_4$ thioalkyl group unsubstituted or substituted with a straight or branched $C_1$-$C_5$ alkyl group, a halogen atom, a straight or branched $C_1$-$C_5$ alkoxy group, or a straight or branched $C_1$-$C_3$ thioalkyl group; and $R^3$ and $R^4$ are each independently a hydrogen atom, or a $C_1$-$C_2$ alkyl group.

17. The pharmaceutical composition of claim 16, wherein in Formula (I'), $R^1$ is a hydrogen atom, and $R^2$ is methyl, ethyl, n-propyl, n-butyl, ethoxy, n-propoxy, n-butoxy or methoxymethoxy.

18. The pharmaceutical composition of claim 16, wherein in Formula (I'), $R^1$ is a hydrogen atom, and $R^2$ is a hydrogen atom; a straight or branched $C_1$-$C_6$ alkyl group; a straight or branched $C_2$-$C_5$ alkoxy group; or a straight or branched $C_1$-$C_3$ thioalkyl group.

19. The pharmaceutical composition of claim 16, wherein the compound of Formula (I') is one or more of the following compounds:

Compound 2
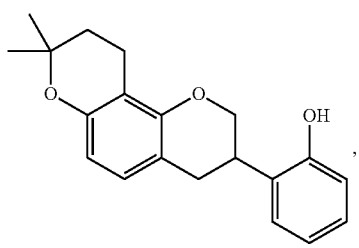
Compound 3
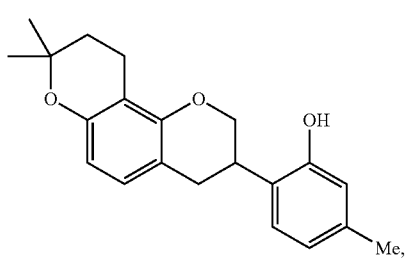
Compound 4
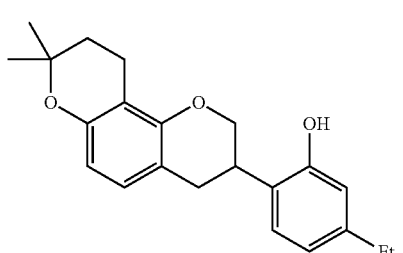
Compound 5
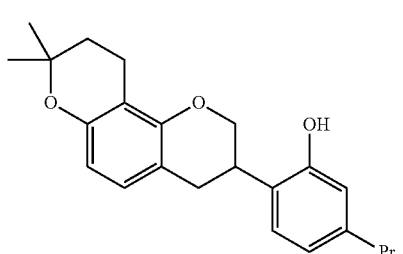
Compound 6
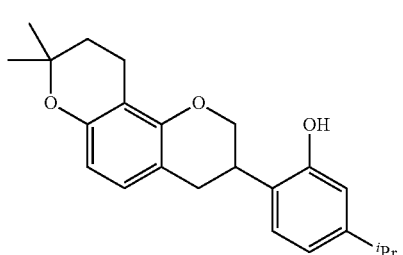
Compound 7
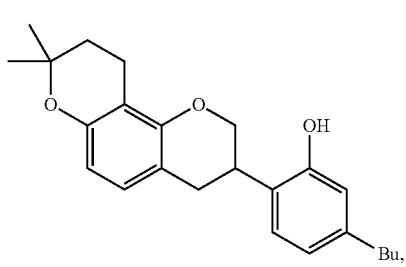
Compound 8
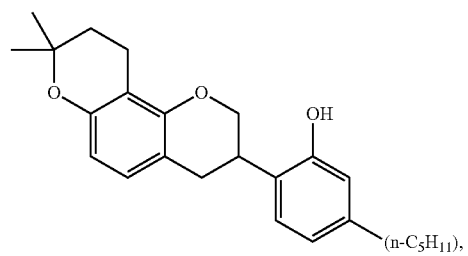
Compound 9
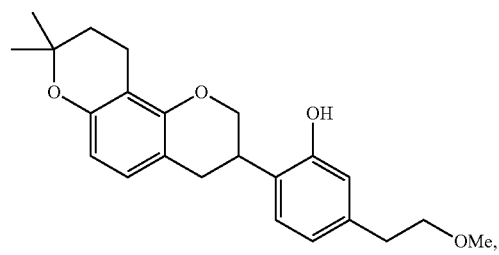
Compound 10
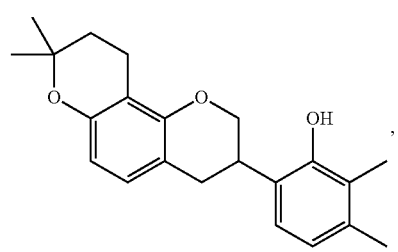
Compound 11
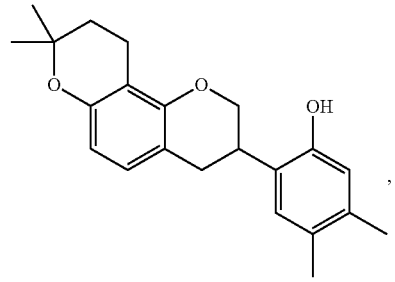
Compound 12
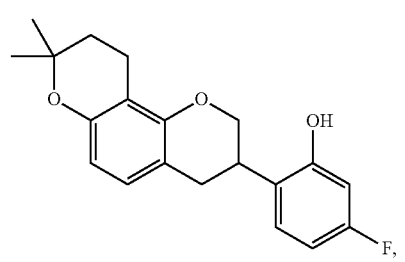
Compound 13

Compound 15
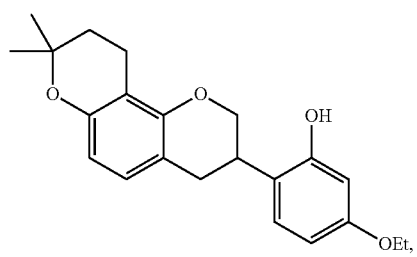
Compound 16
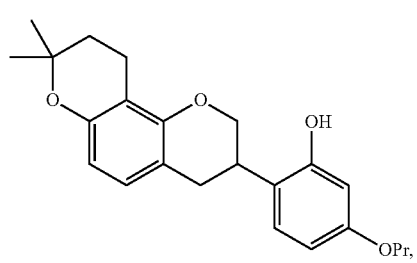
Compound 17
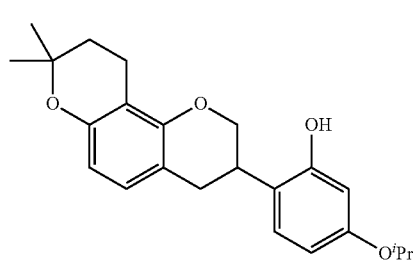
Compound 18
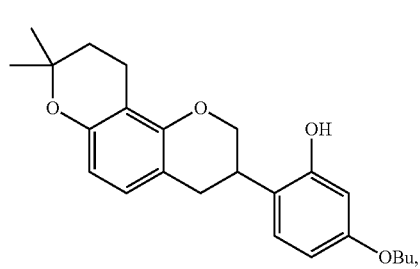
Compound 19
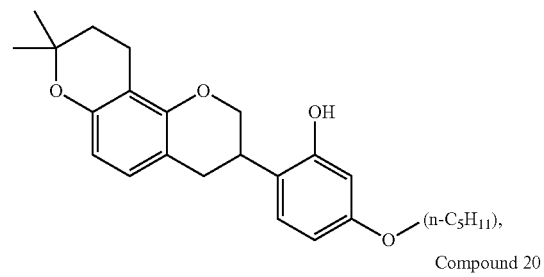
Compound 20
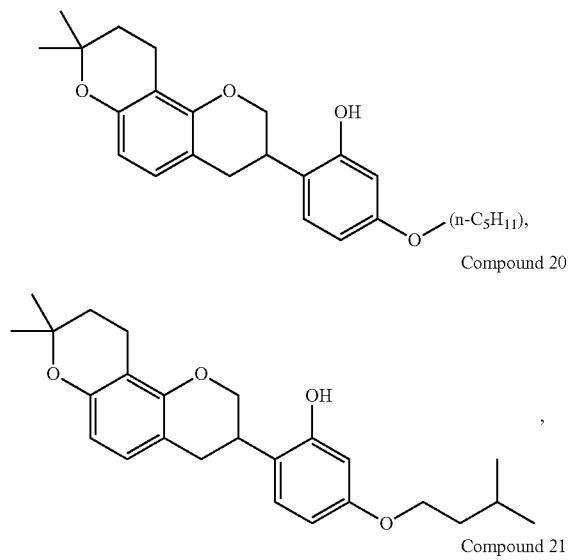
Compound 21
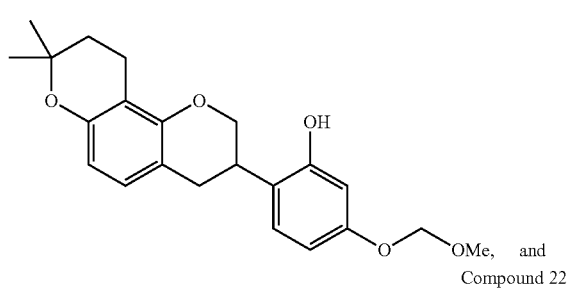
Compound 22
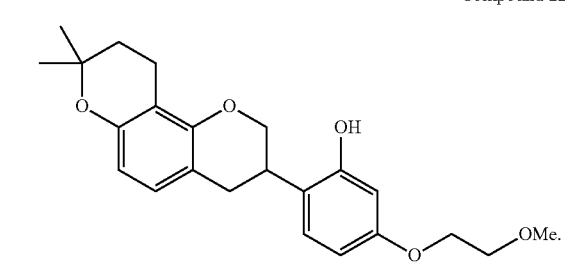
* * * * *